US 8,979,829 B2

(12) United States Patent
Tomasello et al.

(10) Patent No.: US 8,979,829 B2
(45) Date of Patent: Mar. 17, 2015

(54) INTERSTITIAL LASER THERAPY KITS

(75) Inventors: Anthony J. Tomasello, Libertyville, IL (US); William Graveman, Tonganoxi, KS (US); Kambiz Dowlatshahi, Chicago, IL (US); Henry R. Appelbaum, Chicago, IL (US)

(73) Assignee: Novian Health, Inc., Chicago, IL (US)

( * ) Notice: Subject to any disclaimer, the term of this patent is extended or adjusted under 35 U.S.C. 154(b) by 1798 days.

(21) Appl. No.: 12/025,157

(22) Filed: Feb. 4, 2008

(65) Prior Publication Data
US 2008/0185314 A1    Aug. 7, 2008

Related U.S. Application Data

(63) Continuation-in-part of application No. 11/957,040, filed on Dec. 14, 2007, now Pat. No. 8,092,507.

(60) Provisional application No. 60/888,225, filed on Feb. 5, 2007, provisional application No. 60/888,223, filed on Feb. 5, 2007.

(51) Int. Cl.
*A61B 18/18*    (2006.01)
*A61N 5/06*    (2006.01)
(Continued)

(52) U.S. Cl.
CPC .............. *A61N 5/0601* (2013.01); *A61B 18/24* (2013.01); *A61B 19/201* (2013.01); *A61B 2017/00101* (2013.01); *A61B 2018/2005* (2013.01)
USPC ................................. 606/10; 11/16

(58) Field of Classification Search
CPC .................. A61B 18/24; A61B 19/201; A61B 2017/00101; A61B 2018/2005; A61N 5/0601
USPC .......................................................... 606/13
See application file for complete search history.

(56) References Cited

U.S. PATENT DOCUMENTS

| 1,968,997 A | 8/1934 | Drucker |
| 4,222,375 A | 9/1980 | Martinez |

(Continued)

FOREIGN PATENT DOCUMENTS

| DE | 2826383 | 12/1979 |
| JP | 2001148280 | 9/1989 |

(Continued)

OTHER PUBLICATIONS

Written Opinion of the International Searching Authority for International Application No. PCT/US08/50358 dated Nov. 7, 2008.

(Continued)

*Primary Examiner* — Gary Jackson
*Assistant Examiner* — Boniface N Nganga
(74) *Attorney, Agent, or Firm* — Neal, Gerber and Eisenberg LLP

(57) ABSTRACT

Interstitial laser therapy kits are disclosed. The items contained in the kit are useable to perform a single interstitial laser treatment. The kit includes a laser probe cannula, a stylet, a thermal probe, two probe holders, and a removable optical fiber, sterilized and contained in a non-resealable first plastic bag. The first plastic bag has at least one unique kit identifier printed on it. The kit also includes a saline syringe, a hemostasis valve, and a saline tube, contained in a non-resealable second plastic bag. The interstitial laser therapy kit is combined with an appropriate interstitial laser therapy apparatus to perform a single interstitial laser treatment, and after any of the items in a kit has been used, each of the items is discarded. An interstitial laser therapy control system enables the operator to ensure that the kit is used discarded after it has been used.

41 Claims, 23 Drawing Sheets

(51) Int. Cl.
*A61B 18/24* (2006.01)
*A61B 19/00* (2006.01)
*A61B 17/00* (2006.01)
*A61B 18/20* (2006.01)

(56) References Cited

U.S. PATENT DOCUMENTS

| | | | |
|---|---|---|---|
| 4,402,311 A | 9/1983 | Hattori | |
| 4,407,282 A | 10/1983 | Swartz | |
| 4,501,363 A * | 2/1985 | Isbey, Jr. | 206/570 |
| 4,559,942 A | 12/1985 | Eisenberg | |
| 4,616,656 A | 10/1986 | Nicholson et al. | |
| 4,662,368 A | 5/1987 | Hussein et al. | |
| 4,665,927 A | 5/1987 | Daily | |
| 4,681,122 A | 7/1987 | Winters et al. | |
| 4,773,413 A | 9/1988 | Hussein et al. | |
| 4,774,948 A | 10/1988 | Markham | |
| 4,776,334 A | 10/1988 | Prionas | |
| 4,819,630 A | 4/1989 | Dehart | |
| 4,883,062 A | 11/1989 | Nicholson | |
| 4,890,898 A | 1/1990 | Bentley et al. | |
| 4,920,978 A | 5/1990 | Colvin | |
| 4,931,059 A | 6/1990 | Markham | |
| 4,932,934 A | 6/1990 | Dougherty | |
| 4,946,440 A * | 8/1990 | Hall | 604/164.09 |
| 4,950,267 A | 8/1990 | Ishihara et al. | |
| 4,957,481 A | 9/1990 | Gatenby | |
| 4,959,063 A | 9/1990 | Kojima | |
| 4,961,422 A | 10/1990 | Marchosky et al. | |
| 4,967,765 A | 11/1990 | Turner et al. | |
| 5,019,075 A | 5/1991 | Spears et al. | |
| 5,050,597 A | 9/1991 | Daikuzono | |
| 5,059,197 A | 10/1991 | Urie et al. | |
| 5,061,265 A | 10/1991 | Abela et al. | |
| 5,078,142 A | 1/1992 | Siczek et al. | |
| 5,125,925 A | 6/1992 | Lundahl | |
| 5,127,916 A | 7/1992 | Spencer et al. | |
| 5,129,896 A | 7/1992 | Hasson | |
| 5,158,084 A | 10/1992 | Ghiatus | |
| 5,169,396 A | 12/1992 | Dowlatshahi et al. | |
| 5,178,148 A | 1/1993 | Lacoste et al. | |
| 5,178,164 A | 1/1993 | Allen | |
| 5,195,526 A | 3/1993 | Michelson | |
| 5,196,396 A * | 3/1993 | Lieber | 505/460 |
| 5,222,953 A | 6/1993 | Dowlatshahi | |
| 5,234,426 A | 8/1993 | Rank et al. | |
| 5,240,011 A | 8/1993 | Assa | |
| 5,242,437 A | 9/1993 | Everett et al. | |
| 5,312,392 A | 5/1994 | Hofstetter et al. | |
| 5,323,779 A | 6/1994 | Hardy et al. | |
| 5,330,517 A | 7/1994 | Mordon et al. | |
| 5,386,447 A | 1/1995 | Siczek | |
| 5,396,897 A | 3/1995 | Jain et al. | |
| RE34,936 E | 5/1995 | Campbell et al. | |
| 5,415,169 A | 5/1995 | Siczek et al. | |
| 5,484,400 A | 1/1996 | Edwards et al. | |
| 5,520,182 A | 5/1996 | Leighton et al. | |
| 5,569,240 A * | 10/1996 | Dowlatshahi et al. | 606/15 |
| 5,615,430 A | 4/1997 | Nambu et al. | |
| 5,620,479 A | 4/1997 | Diederich | |
| 5,636,255 A | 6/1997 | Ellis | |
| 5,673,696 A * | 10/1997 | Bidwell et al. | 600/437 |
| 5,735,264 A | 4/1998 | Siczek et al. | |
| 5,813,985 A | 9/1998 | Carroll | |
| 5,853,366 A | 12/1998 | Dowlatshahi | |
| 5,954,711 A * | 9/1999 | Ozaki et al. | 606/10 |
| 5,983,424 A | 11/1999 | Naslund | |
| 6,023,637 A | 2/2000 | Liu et al. | |
| 6,058,322 A | 5/2000 | Nishikawa et al. | |
| 6,094,760 A | 8/2000 | Nonaka et al. | |
| 6,241,725 B1 | 6/2001 | Cosman | |
| 6,341,893 B1 | 1/2002 | Matsumoto et al. | |
| 6,391,028 B1 * | 5/2002 | Fanton et al. | 606/45 |
| 6,451,015 B1 | 9/2002 | Rittman et al. | |
| 6,456,684 B1 | 9/2002 | Mun et al. | |
| 6,542,767 B1 | 4/2003 | McNichols et al. | |
| 6,551,302 B1 | 4/2003 | Rosinko et al. | |
| 6,562,028 B2 * | 5/2003 | Nield et al. | 606/15 |
| 6,569,176 B2 | 5/2003 | Jesseph | |
| 6,603,988 B2 | 8/2003 | Dowlatshahi | |
| 6,671,535 B1 | 12/2003 | McNichols et al. | |
| 6,701,175 B2 | 3/2004 | Dowlatshahi | |
| 6,755,849 B1 | 6/2004 | Gowda et al. | |
| 6,865,412 B2 | 3/2005 | Dowlatshahi | |
| 6,896,141 B2 * | 5/2005 | McMichael et al. | 206/571 |
| 6,928,672 B2 | 8/2005 | Pastyr et al. | |
| 7,041,109 B2 | 5/2006 | Dowlatshahi | |
| 7,074,233 B1 | 7/2006 | Gowda et al. | |
| 7,171,253 B2 | 1/2007 | Dowlatshahi | |
| 7,270,656 B2 | 9/2007 | Gowda et al. | |
| 7,274,847 B2 | 9/2007 | Gowda et al. | |
| 8,092,507 B2 | 1/2012 | Tomasello et al. | |
| 2002/0026127 A1 | 2/2002 | Balbierz et al. | |
| 2002/0151778 A1 * | 10/2002 | Dowlatshahi | 600/407 |
| 2003/0023236 A1 | 1/2003 | Gowda et al. | |
| 2003/0035868 A1 | 2/2003 | Coulter et al. | |
| 2003/0060813 A1 | 3/2003 | Loeb | |
| 2003/0191461 A1 * | 10/2003 | Scheller et al. | 606/15 |
| 2003/0226392 A1 * | 12/2003 | Naumiec et al. | 73/1.71 |
| 2004/0215101 A1 * | 10/2004 | Rioux et al. | 600/562 |
| 2004/0243095 A1 * | 12/2004 | Nimkar et al. | 604/500 |
| 2005/0113641 A1 | 5/2005 | Bala | |
| 2006/0095096 A1 | 5/2006 | DeBenedictis et al. | |
| 2006/0104593 A1 | 5/2006 | Gowda et al. | |
| 2006/0145856 A1 * | 7/2006 | Tethrake et al. | 340/572.1 |
| 2006/0217693 A1 | 9/2006 | Gowda et al. | |
| 2006/0241727 A1 | 10/2006 | Dowlatshahi | |
| 2007/0100229 A1 | 5/2007 | Dowlatshahi | |
| 2007/0219544 A1 | 9/2007 | Gowda et al. | |
| 2008/0015560 A1 | 1/2008 | Gowda et al. | |
| 2008/0114340 A1 | 5/2008 | Fox et al. | |
| 2009/0306638 A1 * | 12/2009 | Hillely et al. | 606/21 |

FOREIGN PATENT DOCUMENTS

| | | |
|---|---|---|
| JP | 2000237205 | 5/2000 |
| WO | WO 8704611 | 8/1987 |
| WO | 93/15664 | 8/1993 |
| WO | WO 0013603 | 3/2000 |
| WO | WO 0059394 | 10/2000 |
| WO | 03/011160 | 2/2003 |
| WO | 2005/046753 | 5/2005 |
| WO | 2006/055554 | 5/2006 |

OTHER PUBLICATIONS

International Preliminary Report on Patentability for PCT/US2008/052911 dated Aug. 11, 2009.

Kelsey. "Revolutionizing Breast Treatment with Interstitial Laser Therapy." May 2003. 1-22.

Kelsey. "Revolutionizing Breast Treatment with Interstitial Laser Therapy." Feb. 2005. 1-18.

Dowlatshahi, Kambiz, MD., et al. "Laser Therapy of Breast Cancer with 3-Year Follow-up." *The Breast Journal*, vol. 10, No. 3, 2004. 240-243.

Dowlatshahi, Kambiz, MD., "Interstitial Laser Treatment of Small Breast Cancers," *Lasers in Medicine, Surgery, and Dentistry*. 2003. 677-689.

Dowlatshahi, Kambiz, MD., "Laser Therapy of Small Breast Cancers." Presented at the Third Annual Meeting of the American Society of Breast Surgeons, Apr. 24-28, 2002. 152-166.

Dowlatshahi, Kambiz, MD., "Shift in the Surgical Treatment of Non-Palpable Breast Cancer: Tactile to Visual." *Rush University Medical Center*. Breast Cancer Online <http://www.bco.org>, Oct. 9, 2005, 1-10.

Dowlatshahi, Kambiz, MD., et al. "Stereotactically Guided Laser Therapy of Occult Breast Tumors," published by ARCH SURG in Nov. 2000.

(56) References Cited

OTHER PUBLICATIONS

Mammography Biopsy Chair Brochure written by Hausted, published in 1993.
Mammomat 3000 Nova Brochure written by Siemens, published prior to 2000.
Multifunctional Mammography—High Patient Throughput, Favorable Economics Brochure written by Siemens, published in 1999.
Sonoline Antares—A New Dimension in Ultrasound Brochure written by Siemens, published prior to 2002.
Supplementary European Search Report for EP 08 72 8923 dated May 4, 2010.

\* cited by examiner

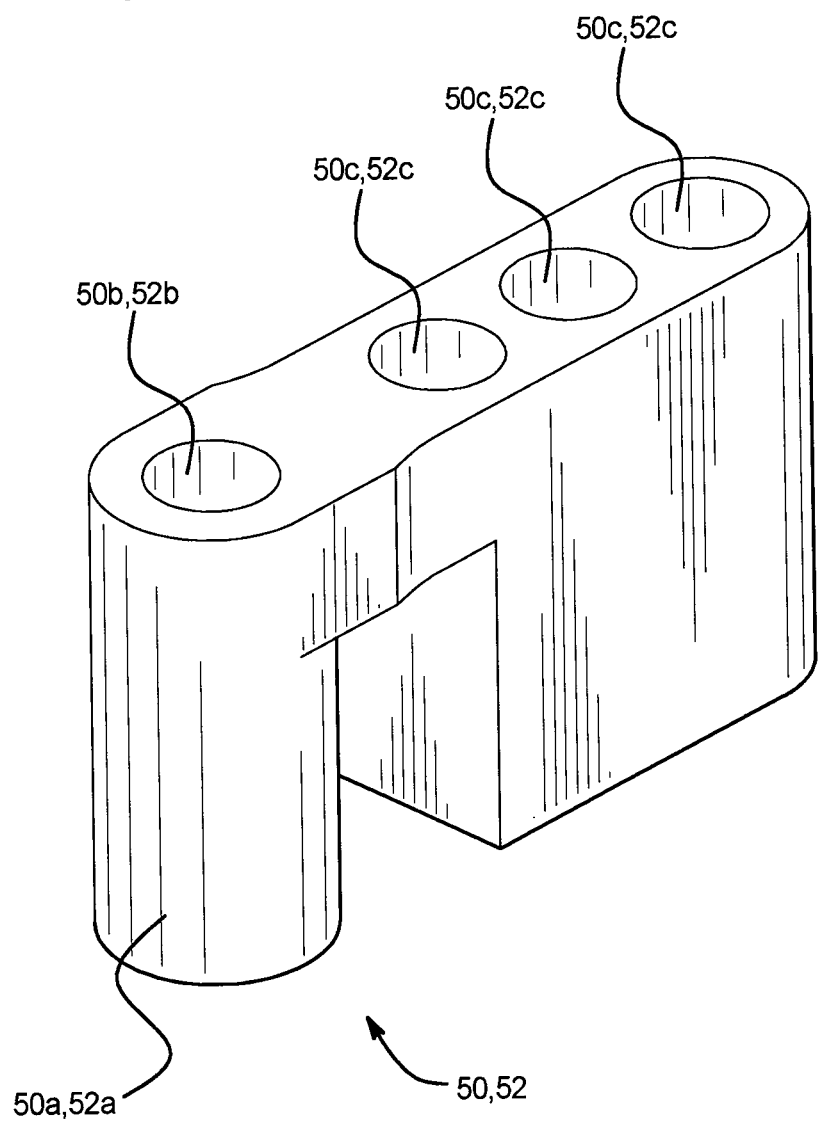

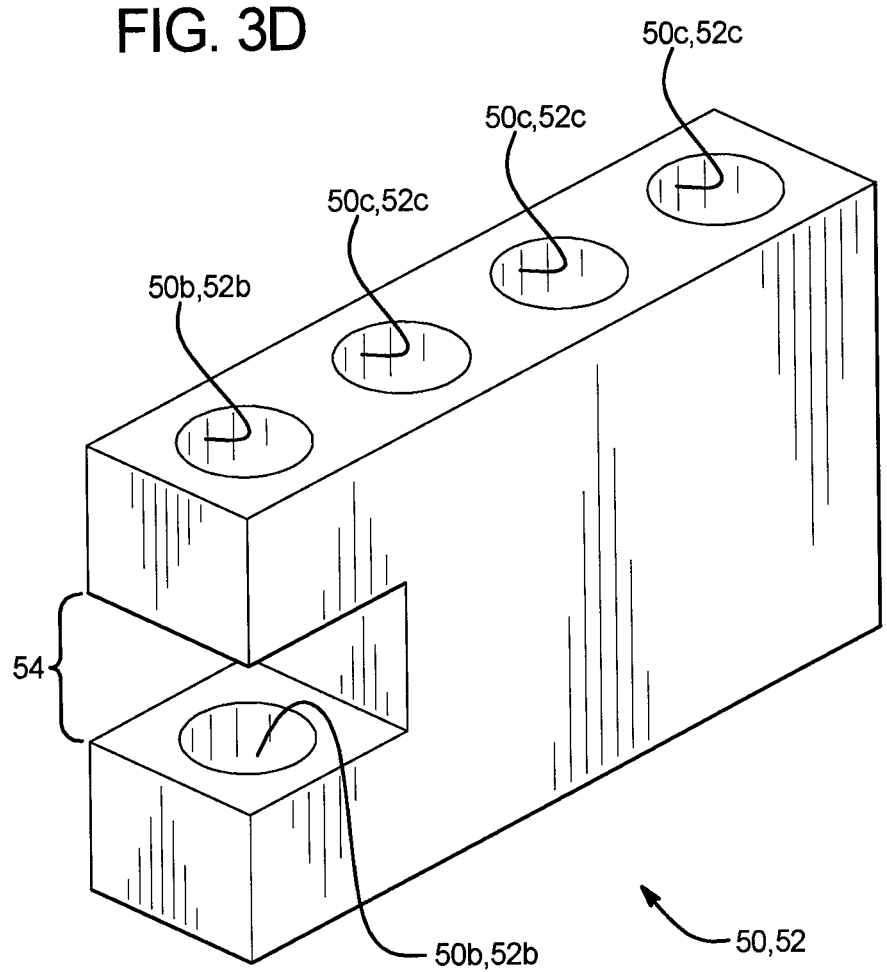

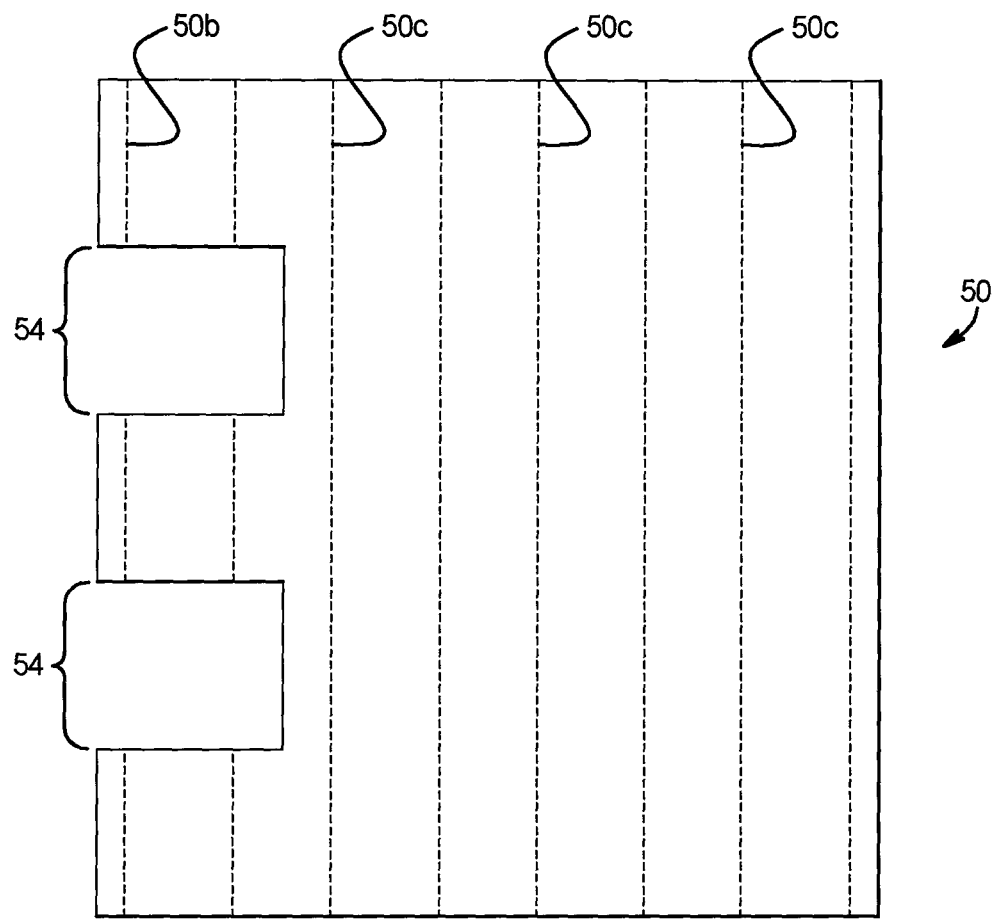

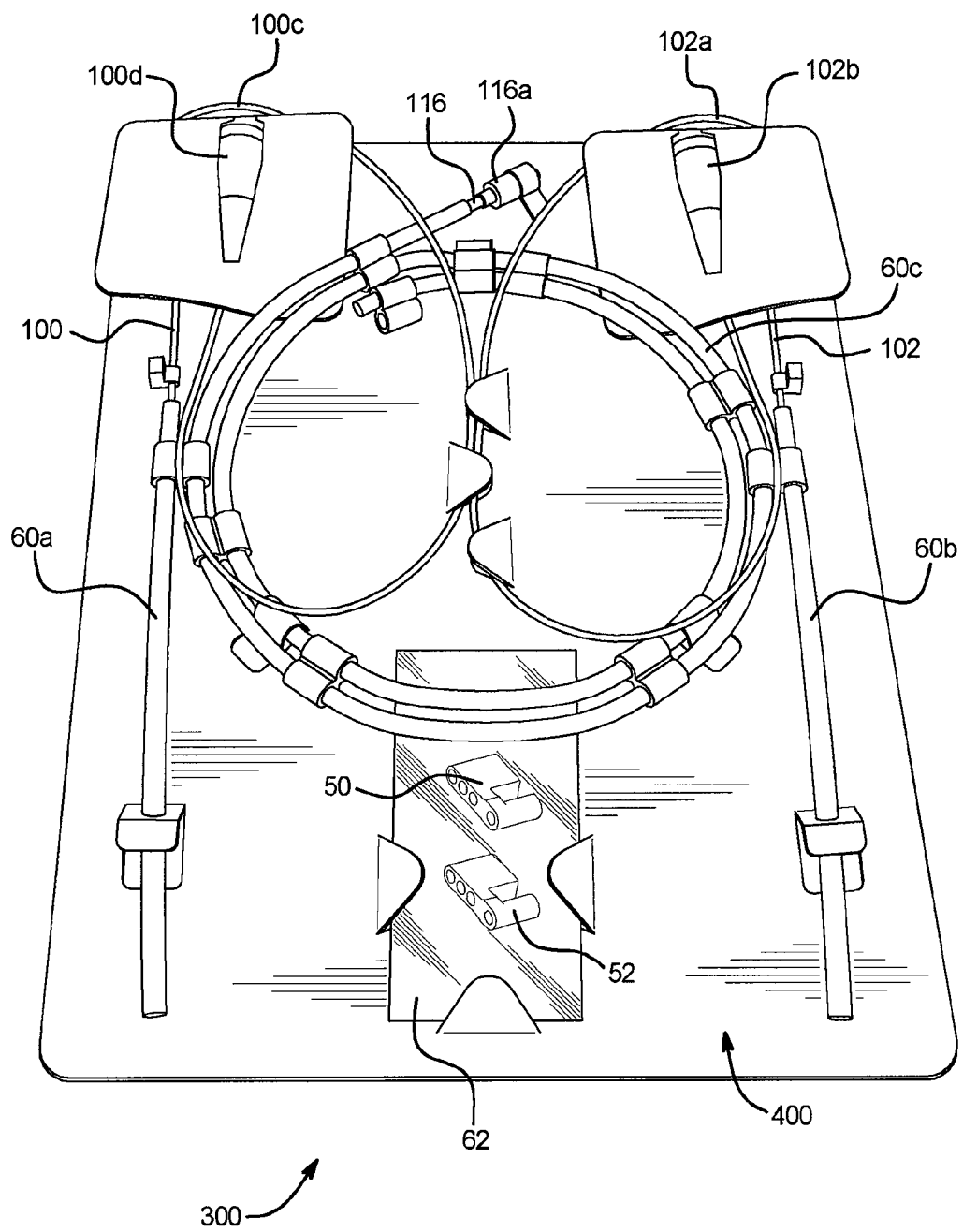

INTERSTITIAL LASER THERAPY KITS

PRIORITY CLAIM

This application is a continuation-in-part of and claims the benefit of U.S. patent application Ser. No. 11/957,040, filed Dec. 14, 2007, is a non-provisional application of, claims priority to and the benefit of U.S. Provisional Patent Application No. 60/888,225, filed Feb. 5, 2007, and is also a non-provisional application of, claims priority to and the benefit of U.S. Provisional Patent Application No. 60/888,223, filed Feb. 5, 2007, the entire contents of which are incorporated herein by reference.

COPYRIGHT NOTICE

A portion of the disclosure of this patent document contains or may contain material which is subject to copyright protection. The copyright owner has no objection to the photocopy reproduction by anyone of the patent document or the patent disclosure in exactly the form it appears in the Patent and Trademark Office patent file or records, but otherwise reserves all copyright rights whatsoever.

DESCRIPTION

The present disclosure relates in general to one or more interstitial laser therapy kits, and in particular to kits containing sterilized single-use components which enable performance of a single interstitial laser treatment.

BACKGROUND

Percutaneous in situ or on-site laser therapy treatment of tissue such as tumors and in particular malignant breast tumors can be more readily performed today because tissue abnormalities such as tumors are being detected at earlier stages. Tissue abnormalities such as breast cancer and other cancers or tumors detected early in development can be effectively treated or destroyed using an ablative agent such as laser energy without conventional surgery.

Interstitial laser treatments of tissue (such as tumors) including malignant tumors (such as breast, liver, brain, and neck tumors), have been in development for more than a decade. For example, U.S. Pat. No. 5,169,396, U.S. Pat. No. 5,222,953, U.S. Pat. No. 5,569,240, U.S. Pat. No. 5,853,366, U.S. Pat. No. 6,603,988, U.S. Pat. No. 6,701,175, U.S. Pat. No. 6,865,412, U.S. Pat. No. 7,041,109, and U.S. Pat. No. 7,171,253 disclose various apparatus and methods for performing interstitial laser treatments of tumors. Certain of these patents disclose laser probes and thermal probes for conducting interstitial laser treatments. Certain of these patents disclose other apparatus for conducting interstitial laser treatments. There is a need for further devices for facilitating interstitial laser therapy.

SUMMARY

Various embodiments of the kit(s) of the present disclosure enable an operator to perform an interstitial laser treatment by using the kit(s) in conjunction with an interstitial laser therapy apparatus. The interstitial laser therapy apparatus is reusable—that is, the apparatus can be used to perform multiple interstitial laser treatments without replacing individual components of the apparatus. In one embodiment, the kit of the present disclosure can be used only once—that is, the items contained in the kit are single-use or are only provided for a single use. It should be appreciated that each of the items in the kit is configured to be attached or to co-act with one or more of the components of the interstitial laser therapy apparatus to enable an operator to perform an interstitial laser treatment. The interstitial laser therapy apparatus and kit(s) enable an operator to treat tissue of interest such as a tumor. It should be appreciated that for purposes of brevity of this application, the tissue of interest to be treated will sometimes be referred to as the "treated tissue" and sometimes be referred to as the "tumor"; however, it should be appreciated that the present disclosure is not limited to the treatment of tumors. It should be appreciated that in different embodiments, the interstitial laser therapy control system is used to monitor interstitial laser energy delivered to tissue other than tumors.

In one embodiment, the interstitial laser therapy apparatus, which enables an operator to apply ablative laser energy to a tumor, includes various electrical or electro-mechanical components. More specifically, the interstitial laser therapy apparatus in one embodiment includes a laser source, a computer including one or more input devices and one or more display devices, an apparatus for converting thermistor resistance readings into temperatures, an infusion pump, an umbilical apparatus including an umbilical cord and a connector box with at least two connectors, and a power source. In various embodiments, the apparatus (including these components) is positioned in one or more housings such as a wheeled cart or a rack configured to be located in a treatment room.

An operator performing an interstitial laser treatment uses an imaging device in conjunction with the interstitial laser therapy apparatus. The imaging device in one embodiment is a conventional rotatable or positionable digital mammography unit. The mammography unit includes a suitable stereotactic unit with connectors for attaching two aligned extendable probe holder attachments. In one embodiment, the extendable probe holder attachments are positioned with respect to the tumor such that probes held by the probe holder attachments can be inserted into the tumor and the tissue adjacent to the tumor and held in place during treatment, as discussed below.

The kit of the present disclosure includes single-use items configured to be used with the interstitial laser therapy apparatus to perform a single interstitial laser treatment. In one embodiment, the interstitial laser therapy kit includes (i) a laser probe, (ii) a thermal probe, (iii) an optical fiber, (iv) at least one probe holder, and (v) a unique kit identifier. In different embodiments, the interstitial laser therapy kit includes (i) a laser probe, (ii) a thermal probe, (iii) an optical fiber, (iv) at least one probe holder, (v) a unique kit identifier, (vi) a hemostasis valve, (vii) a saline tube, and (viii) a syringe.

In one embodiment, the laser probe of the interstitial laser therapy kit includes a cannula, a stylet, and a single thermistor for measuring tissue temperature; the thermal probe includes one or more thermistors for measuring the temperature of tissue adjacent to the tumor; and the optical fiber is configured to be inserted in the laser probe and connected to the connector box. The laser probe and the thermal probe each include at least one thermistor wire with a connector for connecting the thermistor wires to the connector box. The optical fiber is configured so that one end is connectable to a connector on the connector box.

In one embodiment, the interstitial laser therapy kit includes two probe holders each including a plurality of channels. The probe holders are rotatably positioned adjacent to or attachable to the ends of the probe holder attachments of the imaging device, and are configured to enable an operator to position the laser probe and the thermal probe at a known distance from one another and at a desired position in the tumor or in the tissue adjacent to the tumor. It should be appreciated that in different embodiments, the kit includes a single probe holder configured to enable the operator to position the laser probe and the thermal probe with respect to the tumor.

In one embodiment, the hemostasis valve is a y-shaped valve configured such that one port is connectable to the laser probe after the stylet has been removed, one port is connectable to the saline tube, and one port enables the optical fiber to be inserted in the hemostasis valve and into the laser probe.

In one embodiment, the saline tube is configured such that one end is connectable to the hemostasis valve and the other end is connectable to the syringe. In different embodiments, the saline tube is constructed of an appropriate polymer suitable for transferring saline solution into a patient's body. In certain embodiments, the saline tube and the hemostasis valve are constructed of the same material.

The kits of the above embodiments also include a container in which all the respective items are positioned. In one embodiment, the container is a non-resealable plastic bag. In different embodiments, at least one kit identifier including a serial number, a control number, a lot number, and/or other identifying numbers are printed on the non-resealable plastic bag. In different embodiments, the kit identifier(s) are included in the non-resealable plastic bag. Since at least one of the items in the kit is inserted percutaneously into the tumor or the tissue adjacent to the tumor, the items in the kit are sterilized prior to use. In one embodiment, the items contained within the plastic bag are sterilized prior to receipt by the operator.

In different embodiments, additional sterile items are provided in the kit to enable the operator to perform an interstitial laser treatment. In one embodiment, the kit includes various medical materials and dressing implements, such as topical anesthetics, oral medication including pain killers, bandages, towels, gauze and other items that can be (but are not always) necessary for performance of an interstitial laser treatment.

In different embodiments, the items described above are positioned in more than one container such as a plastic bag. In one embodiment, the probes, probe holders, and optical fiber are included in a first kit and the remaining items, including the hemostasis valve, the syringe, the and the saline tube are included in a second kit. In one such embodiment, the first kit includes the kit identifier(s) such as serial numbers, control numbers, and/or lot numbers to enable the interstitial laser therapy apparatus to track the operator's use of the items in the first kit to ensure they are only used to perform one interstitial laser treatment. In one embodiment, the kit identifier is printed on the container in which the items are positioned. In different embodiments, the kit identifier is positioned inside the container in which the items are positioned. In one embodiment, the second kit does not include kit identifiers, as the interstitial laser therapy apparatus does not track the second kit to ensure it is only used once. In different embodiments, additional anesthetics, dressing materials, syringes, and/or other items to perform an interstitial laser treatment are also included in the second kit.

In some embodiments the kits disclosed herein include support structure on which the items in the kit are mounted. In one embodiment, the support structure is a cardboard backing. In different embodiments, the kits disclosed also include one or more sheaths made from plastic or other suitable material for encasing the laser probe, the thermal probe, and the optical fiber. Moreover, in some embodiments the probe holders may be positioned on the support structure, but may be included in a plastic bag or other case to prevent the probe holders from becoming loose in the container.

It should be appreciated that in different embodiments, the items in the interstitial laser therapy kits are not disposable after a single use. In these embodiments, the operator returns the items in the kit to the provider of the kit to enable the items in the kit to be re-sterilized and re-processed. In certain of these embodiments, the provider re-sterilizes the items, re-packages them in a container such as a non-resealable plastic bag, and provides a new unique kit identifier. It should be appreciated that regardless of whether the kits are recyclable and/or reusable, the operator should not perform a second interstitial laser treatment with interstitial laser therapy kit items that have already been used without ensuring that the kits are properly sterilized and processed.

To perform an interstitial laser treatment, the operator in one embodiment obtains an unopened and unused kit that includes the following sterile items: one laser probe, one thermal probe, two probe holders, one optical fiber, and one kit identifier. The operator also verifies that the various components included in the interstitial laser therapy apparatus are available and functioning properly. The operator opens the container and removes the item in the kit, ensuring the sterility is maintained throughout the interstitial laser treatment. Each probe holder included in the disclosed kit is configured to be rotatably inserted into a respective one of the probe holder attachments of the imaging device. The operator inserts each probe holder into one of the probe holder attachments. The probe holders are configured to accept the laser probe in the respective probe channels. The probe holders are further configured to accept the thermal probe in one of a plurality of probe channels such that the probe holders enable a thermal probe to be positioned with respect to the laser probe. The operator inserts the laser probe and the thermal probe into the respective channels in the probe holders. The operator also connects the laser probe and the thermal probe thermistor wires using the appropriate sockets in the connector box. The operator also verifies that the kit is valid by inputting the kit identifier into the computer of the interstitial laser therapy apparatus.

In different embodiments, the operator obtains and opens a second kit including a sterilized hemostasis valve, saline tube, and syringe. The operator tightens the hemostasis valve on the laser probe and tightens a patient end of the saline tube on the hemostasis valve. The operator also tightens the syringe end of the saline tube on the syringe to enable the saline contained in the syringe to be introduced from the saline tube into the laser probe by way of the hemostasis valve. The operator inserts one end of the optical fiber into the appropriate port of the hemostasis valve and further inserts the optical fiber into the laser probe. The operator connects the other end of the optical fiber to the optical fiber connector on the connector box to enable laser energy to be transmitted through the umbilical assembly and applied to the tumor.

It should thus be appreciated that combining the interstitial laser therapy apparatus with the items included in the interstitial laser kit enables the operator to perform an interstitial laser treatment.

It is therefore an advantage of the present disclosure to provide kits including sterile, single-use items configured to be used with an interstitial laser therapy apparatus and positioned in one or more non-resealable containers for performing an interstitial laser treatment including instructions for disposing of the items after the container in which those items are positioned has been opened.

Additional features and advantages of the present invention are described in, and will be apparent from, the following Detailed Description of Exemplary Embodiments and the figures.

DESCRIPTION OF THE DRAWINGS

FIG. 3C is a perspective view of one embodiment of the probe holder included in the interstitial laser therapy kit disclosed herein.

FIG. 3D is a perspective view of another embodiment of the probe holder included in the interstitial laser therapy kit disclosed herein.

FIG. 3H is a perspective view of another embodiment of the probe holder included in the interstitial laser therapy kit disclosed herein.

FIG. 4 is a perspective view of one embodiment of the interstitial laser therapy kit disclosed, including a support structure on which the disposable items of the interstitial laser therapy kit are mounted.

DETAILED DESCRIPTION OF EXEMPLARY EMBODIMENTS

Interstitial Laser Therapy Apparatus

Figure 1:
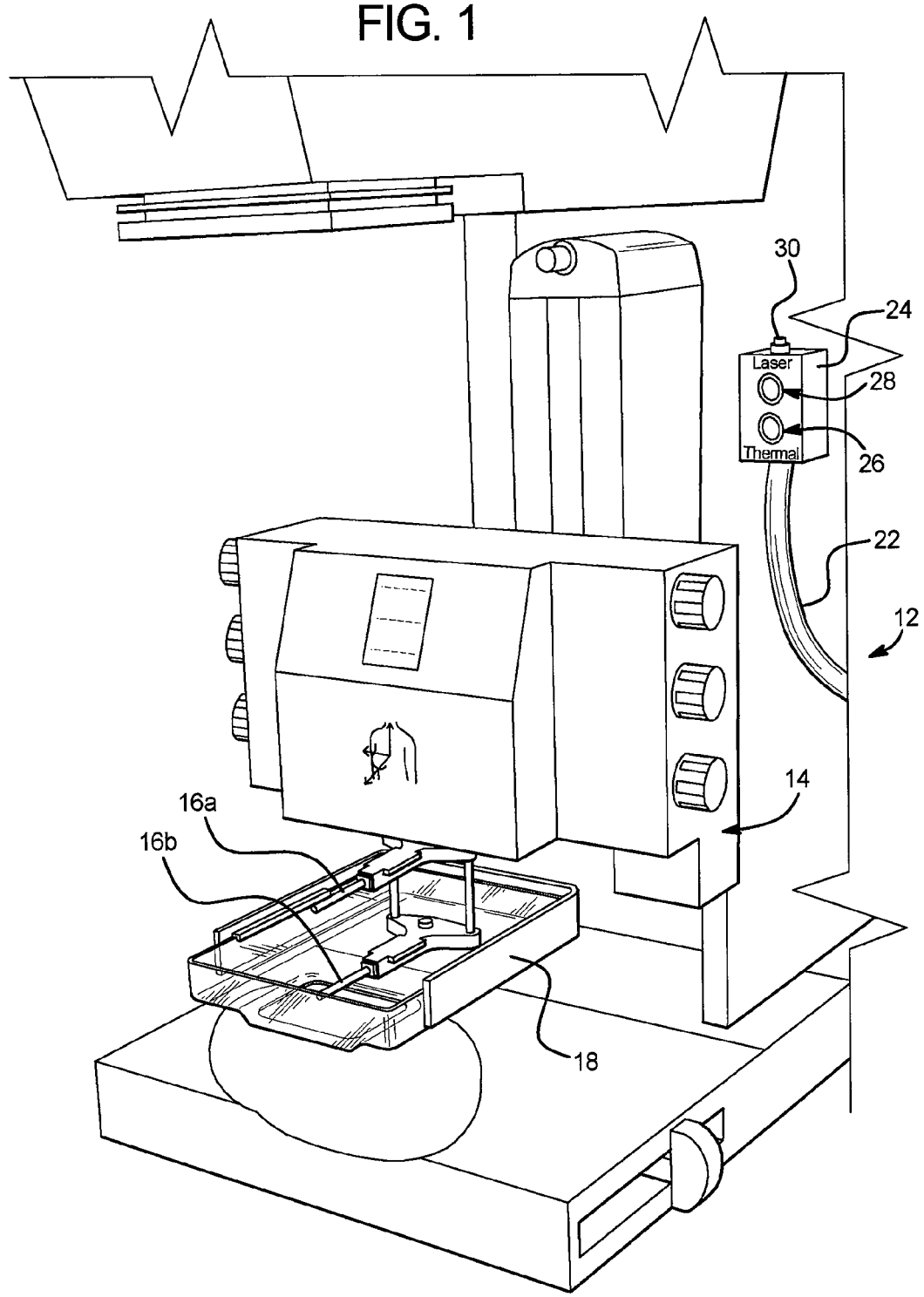
FIG. 1 is a fragmentary perspective view of a mammography unit, a stereotactic device, and an umbilical assembly of an interstitial laser therapy apparatus.

Referring now to the drawings, and particularly to FIG. 1, one embodiment of a platform for the disclosed interstitial laser therapy apparatus and the interstitial laser therapy kit is shown. As illustrated in FIG. 1, an imaging device or unit such as a conventional rotatable or positionable digital mammography device or unit 12 provides a platform for the interstitial laser therapy apparatus. The mammography unit 12 includes a suitable stereotactic device or unit 14. It should be appreciated that the imaging device or unit may be any suitable device or unit including but not limited to x-ray, ultrasound, or magnetic resource imaging devices. It should also be appreciated that the stereotactic device or unit 14 may be any suitable device or unit. The illustrated stereotactic device 14 includes conventional aligned extendable probe holder attachments 16a and 16b, suitably attached at the bottom of the stereotactic device 14. The illustrated stereotactic device 14 includes a compression plate 18 suitably attached at the bottom of the stereotactic device 14 below the upper and lower probe holder attachments 16a and 16b. For ease of illustration, FIG. 1 shows a saline bag instead of a body part (such as a breast) containing the tumor which would be treated using the interstitial laser therapy apparatus.

It should also be appreciated that a conventional treatment bed or platform (not shown) may be positioned relative to the imaging unit 12 to enable interstitial laser therapy to be performed while a patient is lying on the treatment platform. The use of the treatment bed or platform with the imaging unit 12 enables interstitial laser therapy to be performed and, if necessary, adjunctive therapy to be performed in the same treatment room without transferring the patient to a new bed or platform.

FIG. 1 also illustrates an umbilical cable 22 and a connector box 24 (referred to together as the umbilical assembly) of the interstitial laser therapy apparatus. In one embodiment, the umbilical cable 22 is formed of two separate cables enshrouded in protective conduit. The two cables in this embodiment are a thermistor wires cable and an optical fiber. In various embodiments, the umbilical cable 22 includes a replaceable umbilical optical fiber (not shown) which is configured to be removable from the umbilical cable 22 and replaceable in the event the umbilical optical fiber is damaged or otherwise rendered unusable. In different embodiments, the optical fiber in the umbilical cable 22 is not configured to be removable from the umbilical cable 22. The umbilical cable is attachable to the connector box 24, and as illustrated in FIG. 1 the umbilical cable 22 is attached to the connector box 24 prior to performing an interstitial laser treatment.

In the illustrated embodiment, the connector box 24 has three connectors 26, 28, and 30. In this embodiment, connector 26 is a connector including a socket for a plug on a wire attached to one or more thermistors of a thermal probe, connector 28 is a socket for a plug on a wire attached to one or more thermistors of a laser probe, and optical connector 30 is a connector for attaching an optical fiber. In one embodiment, the optical connector 30 includes a screw-on metallic cap that covers the optical connector 30 whenever the interstitial laser therapy apparatus is not in use to prevent the accidental emission of laser energy. In different embodiments, the screw-on cap protects the optical fiber, as any amount of dust, dirt, or scratching damages the optical fiber beyond use. In different embodiments, the connectors 26 and 28 are configured to enable the thermistors of the laser probe 100 and the thermal probe 102 to transmit electrical signals to the umbilical cable 22, and the connector 30 enables the laser energy to be transmitted from the umbilical cable 22 to the optical fiber 116.

The conduit enshrouding the umbilical cable 22 includes a connector (not shown) that attaches to an umbilical bracket (not shown) on a housing containing the electrical and optical components of the interstitial laser therapy apparatus. Thus, the umbilical assembly provides electrical and optical connections between the components of the interstitial laser therapy apparatus and the platform for performing interstitial laser therapy. The umbilical assembly is reusable, and enables the electrical and optical components to be placed a desired distance away from the platform for the interstitial laser therapy apparatus and still send and receive the necessary electrical and optical signals as discussed below.

Figure 2:
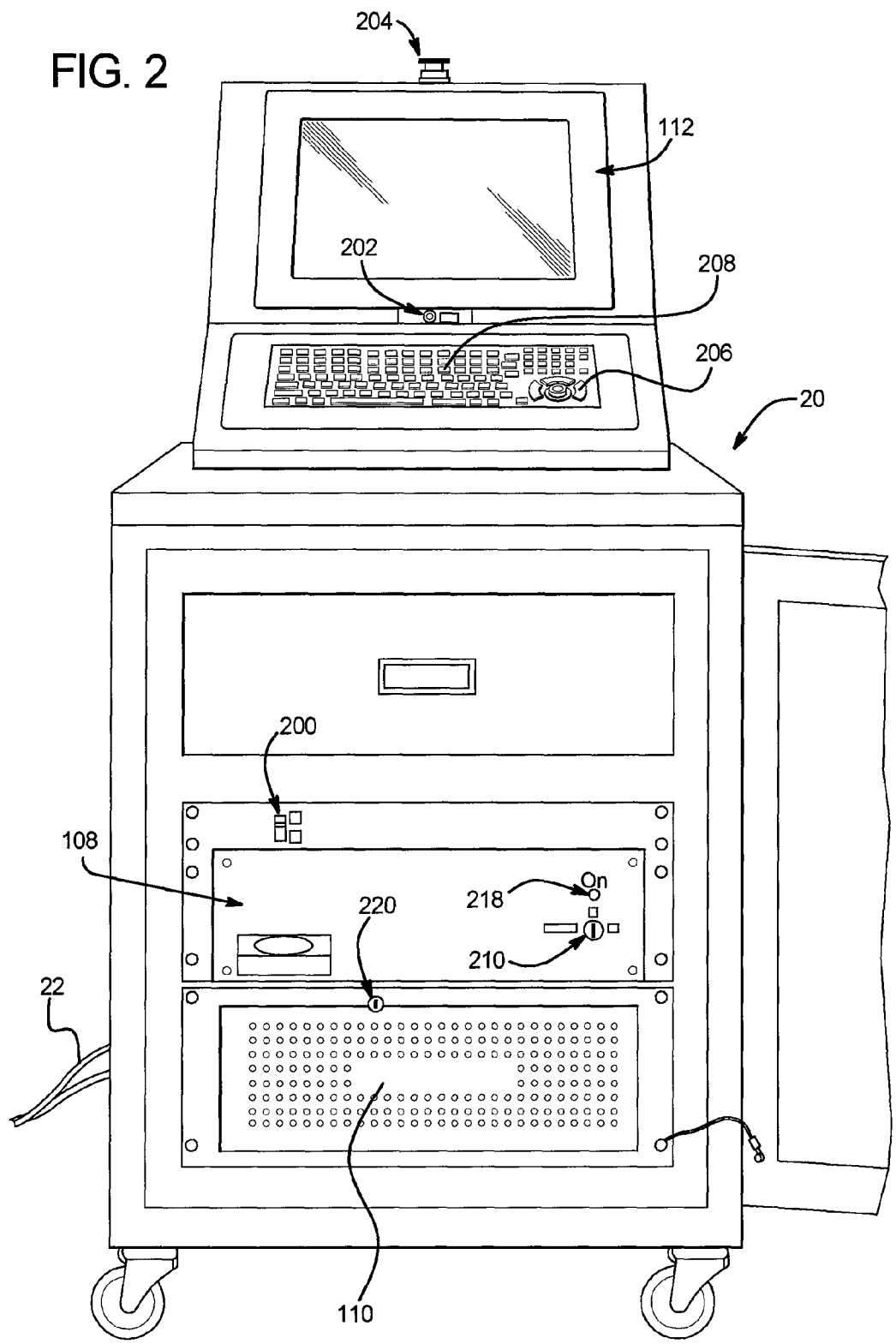
FIG. 2 is a fragmentary perspective view of one embodiment of the interstitial laser therapy apparatus disclosed herein, illustrating the electrical components of the interstitial laser therapy apparatus accessible to the operator and a wheeled cart for housing the electrical components.

Referring now to FIG. 2, the interstitial laser therapy apparatus disclosed in one embodiment includes various electrical components housed in a cart 20. In other embodiments, the components of the interstitial laser therapy apparatus are housed in shelves, cabinets, or other appropriate housing structures. It should be appreciated that the components need not be separate physical components. In one embodiment, the below-described components are housed in a single enclosure, thus forming a single component with all the necessary input and output ports contained on the single enclosure.

In one example embodiment, the wheeled cart 20 of the interstitial laser therapy apparatus houses the following electrical or electro-mechanical components:
 (a) thermistor controller and associated hardware (not shown);
 (b) diode laser source 108 capable of producing 1-8 watts with nominal wavelength of 805 nanometers;
 (c) computer 110 running WINDOWS XP™ operating system with Service Pack 2 or better, including microprocessor (not shown), memory device (not shown), monitor 112, keyboard 208, and mouse 206;
 (d) power distribution unit (not shown) with operator-accessible master power switch 200;
 (e) uninterruptible power supply (UPS) (not shown); and
 (f) isolation transformer (not shown).

In one embodiment, the thermistor controller and associated hardware receives a signal from the thermistors positioned within the tumor being treated or in tissue adjacent to the treated tissue. In different embodiments, the thermistor controller, the computer 110, the keyboard 208, the mouse 206, and the display 112 comprise a control system for controlling application of interstitial laser energy and monitoring an interstitial laser treatment. The thermistor controller converts data received from one or more thermistors (which typically indicates a resistance in the thermistor that varies as the temperature of the thermistor changes) into one or more numbers indicating the temperature detected by the thermistor. The thermistor controller sends the converted temperature data to the computer 110 for processing, as discussed below. In different embodiments, the thermistor controller is configured to receive readings from multiple thermistors simultaneously. In one embodiment, the thermistor controller is configured to receive resistance data from six thermistors and convert the resistance data to temperature data. In this embodiment, the thermistor controller sends data to the microprocessor as a set of thermistor temperature data. That is, the thermistor controller communicates the temperature data to the microprocessor as sets of data about the thermistors in the probes. In different embodiments, the thermistor temperature data set includes one or more thermistor temperatures and an indication that one or more thermistors is not functioning properly. Thus, the data contained in the thermistor temperature data set enables the microprocessor to determine the temperatures detected by the thermistors as well as whether the thermistors are functioning properly.

In one embodiment, the laser source 108 includes a compact, computer-controlled diode laser source which is coupled to an optical fiber delivery system. The laser source 108 in one embodiment is a diode laser source that delivers 805 nm light radiation. In one embodiment, the laser 108 is classified as a Class IV medical laser as described in 21 C.F.R. §1040.10(b)(11) by the U.S. Center for Devices and Radiological Health (CDRH). Therefore, the apparatus disclosed includes a laser source 108 with software-limited power of 8 watts continuous wave (CW). Further, the apparatus in one embodiment includes a protective case which prevents unintended human exposure to laser radiation above Class I limits, a safety shutter that prevents laser energy from exiting the instrument except during operation, and appropriate warning labels. In one embodiment, the shutter covers the optical emission point of the laser energy such that when the shutter is closed, laser energy cannot be emitted even if the laser source 108 is powered on. In this embodiment, when the shutter is opened, the laser source 108 emits laser energy. In different embodiments, the laser source 108 is configured to send one or more signals to a microprocessor to communicate the status of the laser source. In one embodiment, the laser source sends messages indicating whether it is emitting laser energy and whether the shutter is open or closed. In different embodiments, the laser source also sends a signal indicating the amount of energy being emitted. The laser source 108 in different embodiments is also configured to respond to one or more signals sent by a microprocessor, such as heartbeat signals, signals requesting the laser source 108 to close the shutter, or signals requesting that the laser source 108 change the amount of laser energy being emitted. It should be appreciated that in different embodiments, laser sources that are not diode laser sources with the above specifications can be used to perform interstitial laser treatment. For example, a YAG laser source may be used to provide interstitial laser energy. For convenience, the any suitable laser source for performing interstitial laser therapy will be referred to throughout this application as a "laser source."

In one embodiment, the apparatus disclosed includes software installed on at least one memory device in and executed by a microprocessor of the computer 110 that is configured to receive information from the thermistor controller indicating the temperature detected by each thermistor monitored by the thermistor controller. The software in this embodiment is configured to cause the microprocessor to prevent the laser source 108 from generating laser energy (i.e., it does not send the laser source 108 the necessary signal to begin generating laser energy) until all thermistors monitored by the thermistor controller detect a resistance indicating a temperature at or near body temperature (e.g. approximately 35° C.). If the thermistor controller does not communicate with the computer 110 that each of the thermistors detects a temperature near body temperature, the microprocessor is configured not to send the appropriate signal to the laser source 108 to begin generating laser energy.

The computer 110 also includes software configured to generate and display a Graphical User Interface (GUI) on monitor 112 to enable an operator to manage patients, monitor interstitial laser treatments, and manually control the amount of laser energy applied to the tumor using the mouse 206 and keyboard 208. The software installed on the computer 110 is also included in the interstitial laser therapy control system, and is configured to monitor the temperatures detected at one or more thermistors based on the signals received from the thermistor controller and to instruct the laser source 108 to apply the appropriate amount of laser energy to perform interstitial laser treatment.

In one embodiment, the cart 20 houses a UPS that is configured to provides battery backup to the laser source 108, the computer 110, and the thermistor controller in case the power in the hospital or other facility in which the treatment is being performed goes out. Therefore, neither a power failure in the hospital or other facility in which the cart 20 is located, nor accidentally unplugging the cart 20 from a wall socket causes power to immediately cease to the various components contained in the cart 20.

The interstitial laser therapy apparatus also includes three electro-mechanical switches or buttons configured to enable direct control of the laser source 108, and which also make up the control system. The first electro-mechanical switch in one embodiment is an on/off key switch 210 on the front of the laser case. The second electro-mechanical switch is a yellow shutter switch 202 in the middle of the console that is configured to turn the laser beam off by engaging the internal laser shutter of the laser source 108 when actuated. The third electro-mechanical switch is a red emergency stop switch 204 that is configured to cut off power to the laser source 108 by preventing electricity from flowing to the laser source 108 when actuated. In one embodiment, each switch is labeled to indicate the function performed by actuating the switch.

In different embodiments, the components included in the cart 20 are labeled where appropriate to indicate the functionality of the component and/or any dangerous conditions or warnings associated with the component.

Table 1 below indicates the physical and technical specifications of one embodiment of the cart 20 and the various components housed in the cart that comprise the interstitial laser therapy apparatus.

TABLE 1

| Laser Specifications | |
|---|---|
| Laser Type | Diode Laser |
| Laser Class | Class 4 |
| Max Power Output | 8 W |
| Wavelength | 805 nm ± 15 nm |
| Mode of Operation | Continuous wave |
| Optical Output | Multimode |
| Calibration | Internal, automatic, ±20% |
| Electrical Specifications | |
| Power Source | 120 V~12 A 60 Hz |
| Nominal Voltage | 120-240 V AC |
| Nominal Frequency | 50-60 Hz |
| Nominal Current | 12 A max |
| Electrical shock protection | Metal case-grounded |
| Class I Equipment | Protective grounding including hospital grade plug and outlet |
| Patient Connection | Type BF patient-connected laser and thermal probe 102s. |
| Dimensions, etc. | |
| Height | 51 in |
| Depth | 32 in |
| Width | 24 in |
| Weight (est.) | 250 lbs (with cart 20) |
| Power cord length | 12 ft |
| Ordinary Protection | Not protected against ingress of moisture. |
| Operating Environment | 10°-40° C., 0-80% RH, decreasing linearly to 50% RH at 40° C. |
| Altitude | Sea level to 2,000 meters. |
| Probe Type | Disposable, single use probes |

In the embodiment of the cart 20 illustrated in FIG. 2, the master power switch 200, laser source 108, and computer 110 are visible. In this embodiment, the master power switch 200 is configured to control the flow of electricity to all the components housed in the cart 20. Activation of the master power switch 200 enables an operator to cut off power to the components in the cart 20 despite an included UPS, thus cutting off power to the interstitial laser therapy apparatus. The laser source 108 includes a laser power key switch 210 which is configured to be actuated by turning a key. By requiring a key to enable the laser source 108, the apparatus is configured to enable the operator to maintain a great deal of control over when and whether the laser is activated. In an embodiment, when the laser source 108 is "on" (i.e., power is being supplied to the laser source 108), the laser "on" light 218 is illuminated. Similarly, when the computer 110 is "on," a computer "on" light (not shown) is illuminated. In the illustrated embodiment, the cart 20 is configured to prevent the operator from accessing the computer 110 by including a key lock 220 that ensures that the cover of the computer 110 remains closed. In this embodiment, the key lock 220 ensures that no unauthorized hardware modifications are made to the computer 110.

Interstitial Laser Therapy Kit

Figure 3:
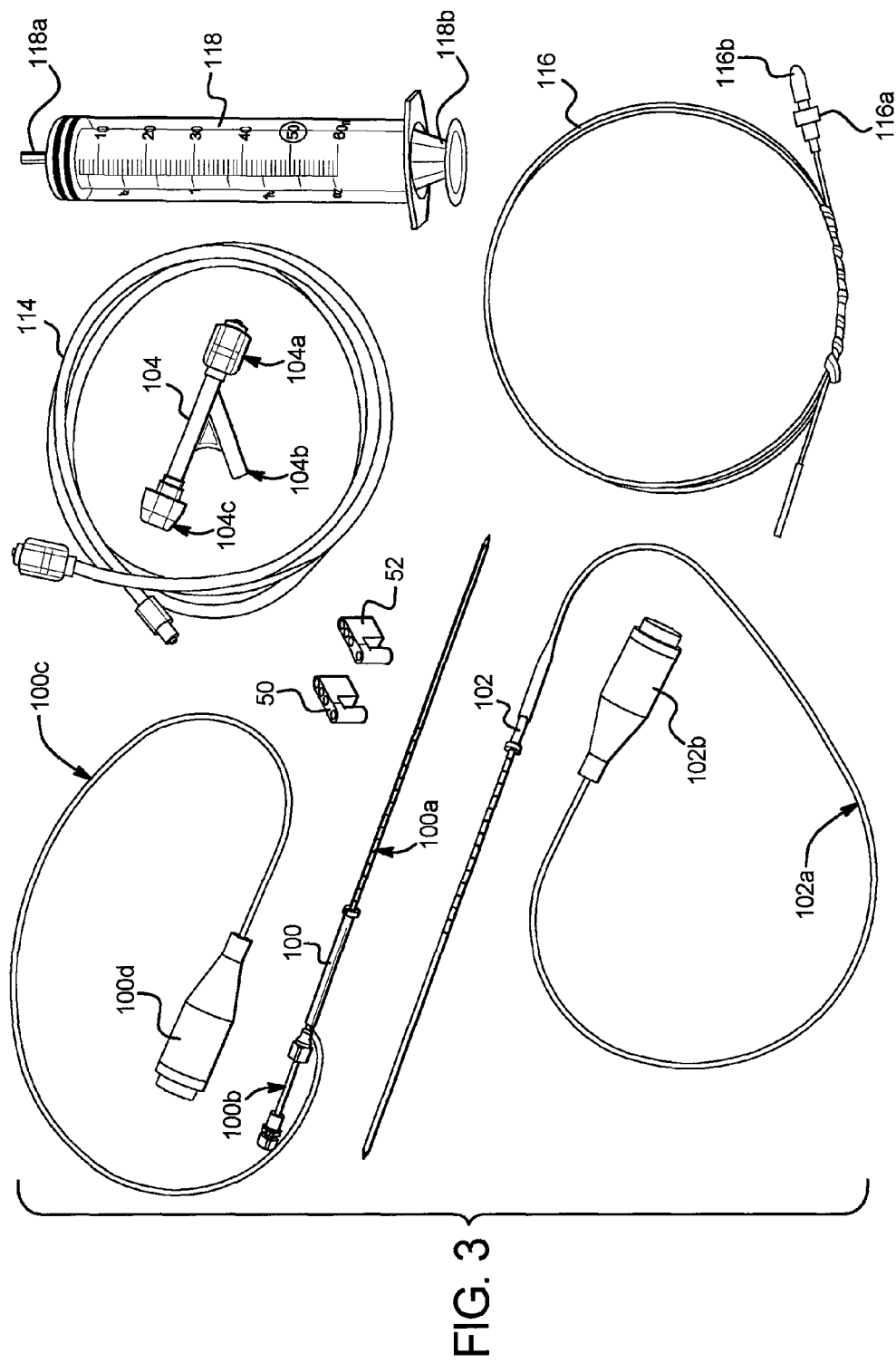
FIG. 3 is a perspective view of the disposable items which in one embodiment are coupled with the components of the interstitial laser therapy apparatus disclosed to perform interstitial laser therapy.

Referring now to FIG. 3, an example of the disposable items which are configured to be coupled with the interstitial laser therapy apparatus to perform interstitial laser energy treatments is illustrated. The disposable items include the following:
  (i) one laser probe 100;
  (ii) one thermal probe 102;
  (iii) one optical fiber 116;
  (iv) two probe holders 50 and 52
  (v) one 60 cc saline syringe 118;
  (vi) one saline tube 114;
  (vii) one hemostasis valve 104 to which the laser probe 100, the optical fiber 116, and the saline tube 114 connect; and
  (viii) one container (not shown), in which the above items are positioned.

Figure 3A:
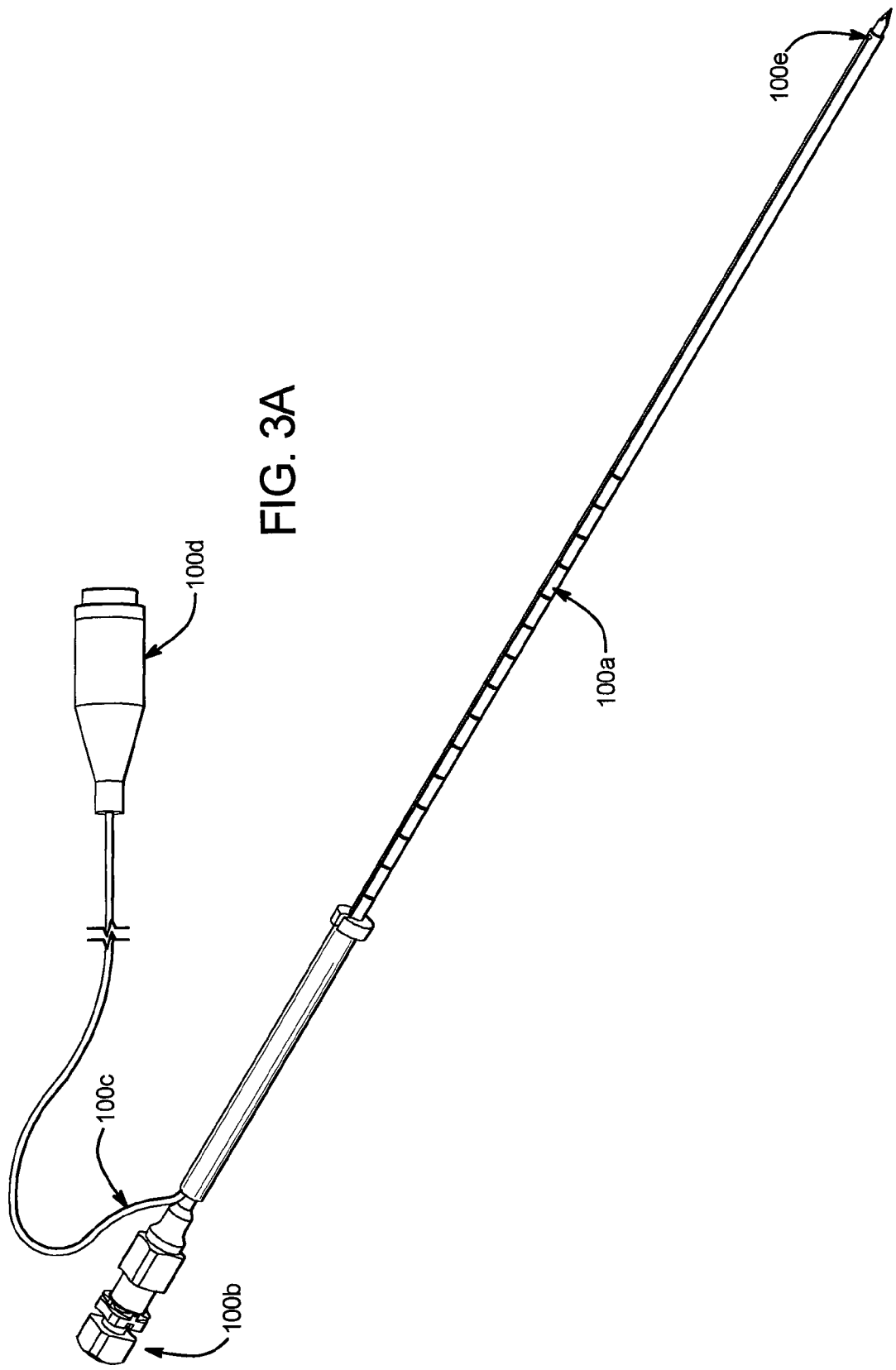
FIG. 3A is a perspective view of one embodiment of the laser probe included in the interstitial laser therapy kit disclosed herein.

Referring to FIGS. 3 and 3A, in different embodiments, the laser probe 100 is constructed from hollow 14 gauge 304 stainless steel and includes a cannula 100a and a stylet 100b. In some such embodiments, the cannula 100a is a trocar, which enables an operator to pierce a patient's skin using the tip of the cannula. The laser probe also includes a thermistor $T_L$ 100e located on the tip of the laser probe 100, mounted externally to the cannula 100a. It should be appreciated that in different embodiments, the laser probe 100 does not include a thermistor $T_L$, or includes a thermistor $T_L$ 100e which is not mounted externally to the cannula 100a. In various embodiments in which the laser probe 100 includes a thermistor $T_L$, the laser probe 100 includes a laser probe wire 100c that connects the thermistor to the laser probe connector 100d. The probe is configured to be insertable through at least one laser probe channel in each probe holder 50 and 52. Moreover, the hollow cannula 100a is configured so that when the stylet 100b is removed from the cannula 100a, the optical fiber 116 and a quantity of saline solution are insertable in the cannula 100a. The laser probe thermistor wire 100c is configured to communicate a signal indicating the resistance detected by the laser probe thermistor to the thermistor controller contained in cart 20. Laser probe connector 100d is configured to be insertable in laser probe connector socket 28 on connector box 24 to connect the laser probe thermistor wire 100c to the thermistor controller. It should be appreciated that in different embodiments, the laser probe includes a cannula without a trocar which is configured to receive the stylet. In these embodiments, the operator makes an incision with a scalpel or other appropriate cutting tool such that the laser probe 100 is insertable in the tumor mass. Alternatively, if the operator performs a biopsy prior to inserting the laser probe 100 as discussed below, a cannula without a stylet (not shown) is insertable in the cavity left by the biopsy. In still other embodiments, the laser probe 100 does not include the stylet 100b. In such embodiments, the operator performs a biopsy prior to inserting the laser probe 100 as discussed below; thus, the stylet is not necessary to pierce the skin and enable the laser probe 100 to be inserted.

Figure 3B:
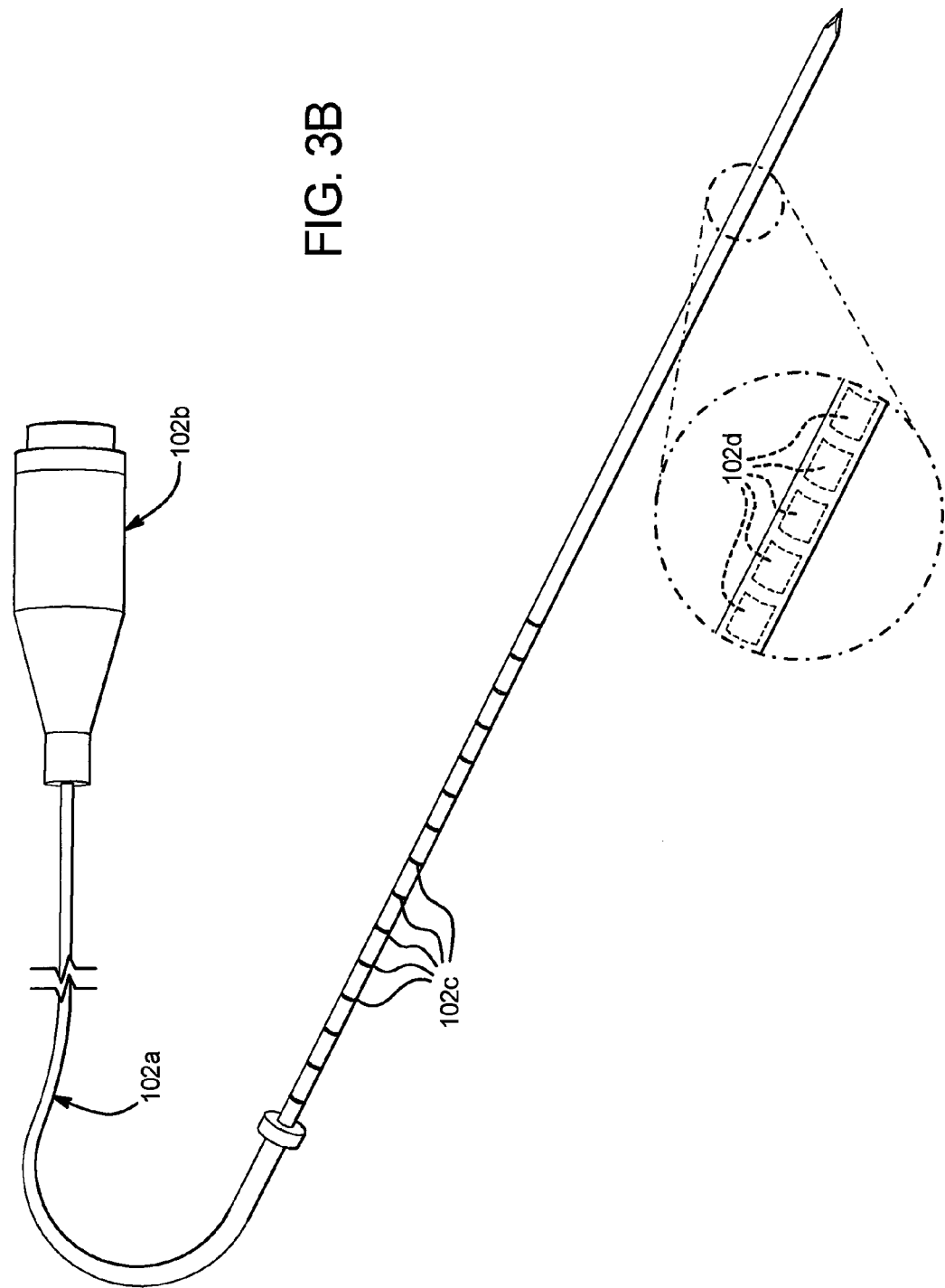
FIG. 3B is a perspective view of one embodiment of the thermal probe included in the interstitial laser therapy kit disclosed herein.

In one embodiment, illustrated in FIGS. 3 and 3B, the thermal probe 102 is constructed of solid 14 gauge 304 stainless steel and includes five internal thermistors 102d (referred to in one embodiment as $T_1$, $T_2$, $T_3$, $T_4$, and $T_5$, where $T_1$ is closest to the tip of the probe) that detect resistances at various locations along the length of the thermal probe 102. The thermal probe 102 is configured to include a thermal probe thermistor wire 102a and a thermal probe connector 102b to enable an operator to connect the thermal probe 102 to the thermal probe connector socket 26 on the connector box 24 such that resistances detected by the one or more thermistors 102d of the thermal probe 102 are communicated to the thermistor controller. In different embodiments, the thermal probe wire includes more than one thermistor wire such that a single thermal probe wire is configured to transmit resistances detected by each of a plurality of thermistors. In an embodiment illustrated by FIG. 3B, the thermal probe 102 includes a series of spaced-apart marks 102c that enable the operator to properly position the thermal probe 102 with respect to the laser probe 100, as discussed below.

Referring now to FIGS. 3 and 3C, the probe holders 50 and 52 in one embodiment are configured to be rotatably inserted in the probe holder attachments 16a and 16b. In one embodiment, each probe holder 50 and 52 includes an integrated bushing 50a or 52a which is rotatably insertable in a hole in each of the probe holder attachments 16a and 16b. In a different embodiment, the bushing is not integrated with the probe holder 50 or 52. In either embodiment, the bushing 50a or 52a includes a channel 50b or 52b into which that the laser probe 100 is insertable such that the bushing, the channel in the bushing, the hole in the probe holder attachments, and the laser probe 100 are co-axial when the probe holder 50 and 52 has been rotatably inserted into the probe holder attachment 16a or 16b. Probe holders 50 and 52 each further include thermal probe channels 50c and 52c to enable the operator to insert the thermal probe 102 at a known distance from the laser probe 100. In one embodiment, the spaced-apart marks 102c of the thermal probe 102 enable the operator to position the thermal probe 102 at a desired depth in the probe holders 50 and 52 with respect to the laser probe 100.

Figure 3E:
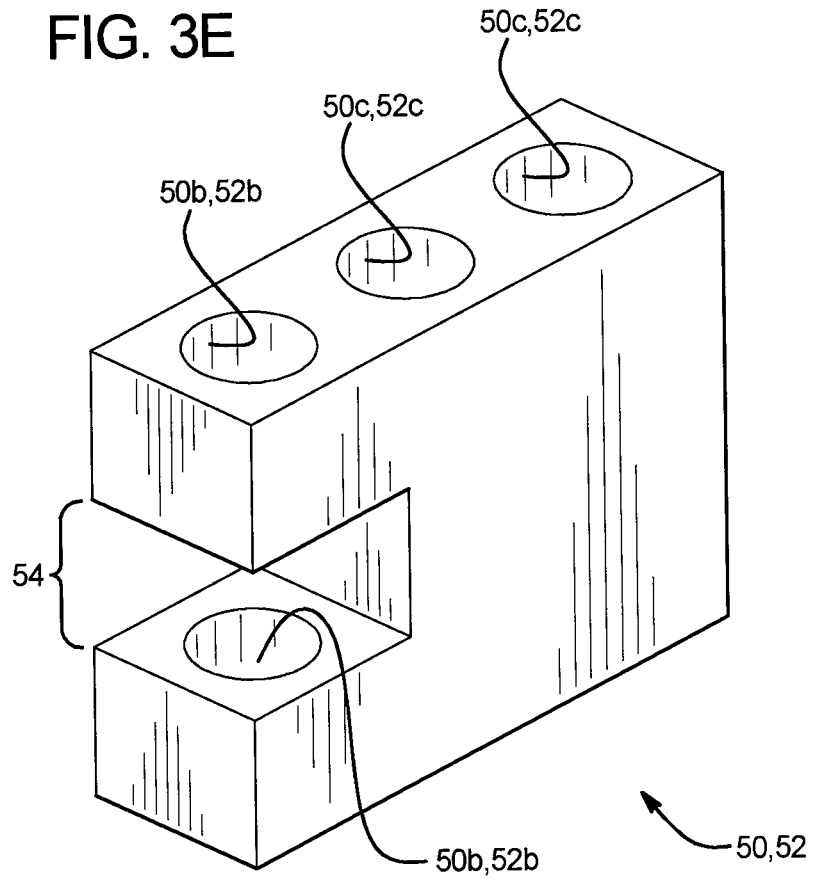
FIG. 3E is a perspective view of another embodiment of the probe holder included in the interstitial laser therapy kit disclosed herein.
Figure 3F:
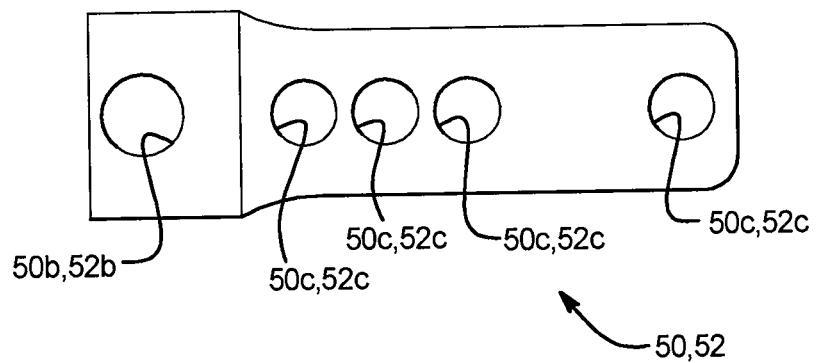
FIG. 3F is a perspective view of another embodiment of the probe holder included in the interstitial laser therapy kit disclosed herein.

In an alternative embodiment, illustrated in FIGS. 3D, 3E, and 3F, the probe holders 50 and 52 include two channels 50b or 52b that have the same diameter and are co-axial. The channels are separated by a space between the channels 54, into which the probe holder attachments 16a and 16b are inserted. The probe holders 50 and 52 are alignable with the probe holder attachments 16a and 16b such that a hole in the probe holder attachments 16a and 16b with the same diameter as the channels 50b and 52b is coaxial with the channels. The laser probe 100 is insertable through the channels such that the laser probe passes through the channels and through the hole in the probe holder attachment 16a or 16b. In this embodiment, the probe holder 50 or 52 pivots about the axis shared by the channels 50a and 50b, the hole in the probe holder attachments 16a and 16b, and the laser probe 100. In the embodiments illustrated in FIGS. 3D, 3E, and 3F, the probe holders 50 and 52 still include a plurality of thermal probe channels 50c and 52c to enable the operator to position the thermal probe 102 at a known distance from the laser probe 100. In different embodiments, the probe holders 50 and 52 include two or more thermal probe channels 50c and 52c, and the probe holder channels 50c and 52c are evenly or unevenly spaced.

Figure 3G:
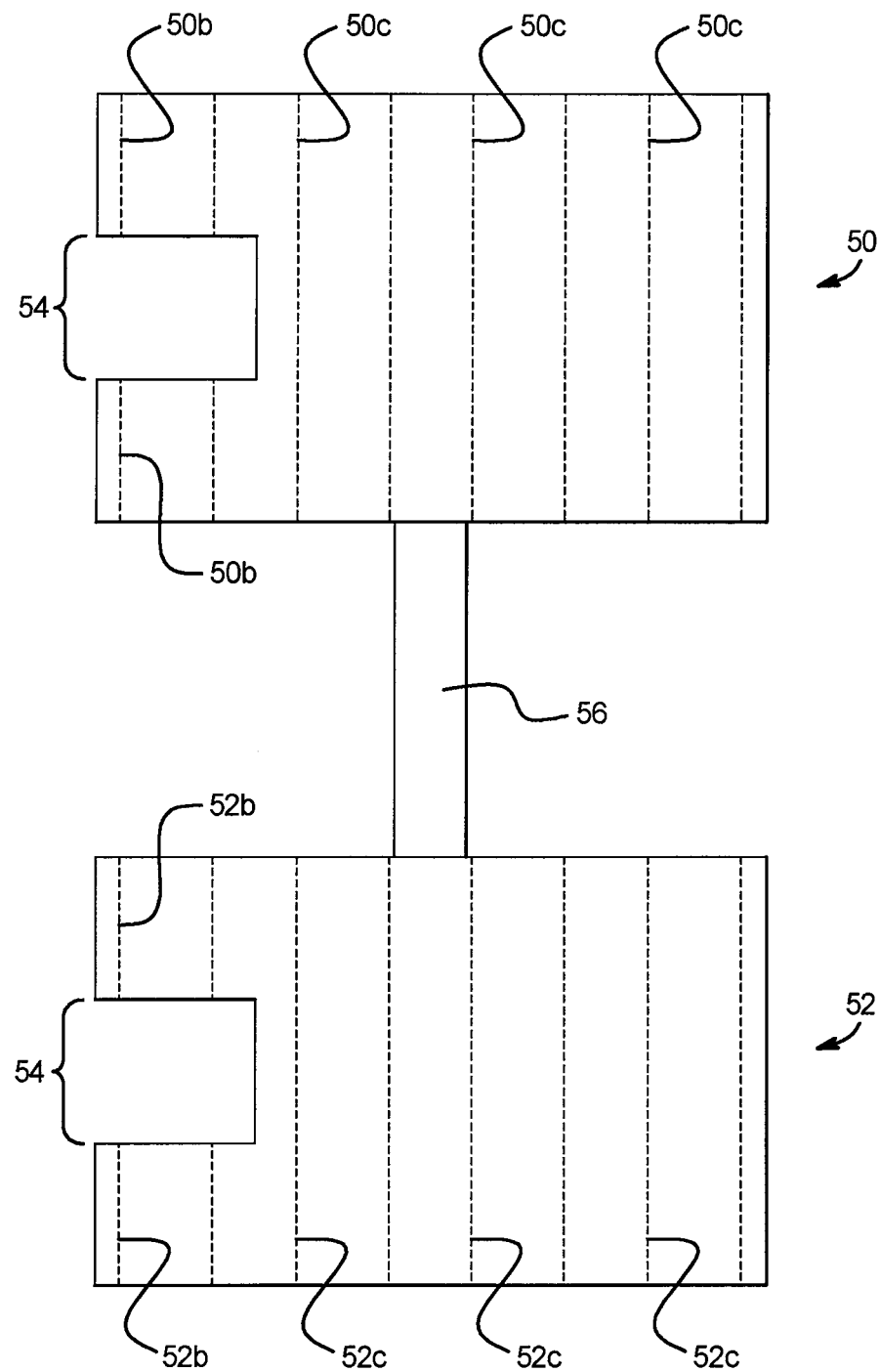
FIG. 3G is a perspective view of another embodiment of the probe holder included in the interstitial laser therapy kit disclosed herein.

In one embodiment, illustrated in FIG. 3G, the probe holders 50 and 52 include laser probe channels 50b and 52b and a plurality of thermal probe channels 50c and 52c. The probe holders 50 and 52 each also include a space in the laser probe channel 50b and 52b into which the probe holder attachments 16a and 16b are insertable. In this embodiment, the probe holders also include a connecting member 56 for connecting the probe holder 50 to the probe holder 52. It should be appreciated that in different embodiments the connecting member 56 is replaceable, to enable the probes 50 and 52 to be connected at different distances from each other, depending on the distance between the probe holder attachments 16a and 16b.

It should be appreciated that a further alternative embodiment, the interstitial laser therapy kit disclosed herein includes a single probe holder 50, as illustrated by FIG. 3H. In this embodiment, the probe holder 50 includes a laser probe channel 50b and a plurality of thermal probe channels 50c.

Further, the laser probe channel 50b includes two spaces 54 into which the probe holder attachments 16a and 16b are insertable. In this embodiment, the probe holder 50 is configured to be connectable with two probe holder attachments 16a and 16b, despite only being a single probe holder 50. In different embodiments, the single probe holder 50 includes a single space 54 and is configured to be connectable only to one of the probe holder attachments 16a or 16b.

Referring to FIG. 3, the optical fiber 116 in one embodiment includes a connector 116a that enables an operator to connect the optical fiber 116 to the optical fiber connector 30 on connector box 24. In one embodiment, the optical fiber 116 also includes a connector cover 116b that prevents the optical fiber 116 from becoming scratched and/or dirty when it is not connected to the connector box 24. It should be appreciated that because of the fragile nature of the optical fiber 116, the operator should inspect the optical fiber 116 prior to each interstitial laser treatment to ensure that the optical fiber 116 is in good condition and that there are no kinks or tears (a kink is defined as any bend that has a defined or obvious inflection point). The operator should also inspect the optical fiber connector 116a at the end of the optical fiber 116 for wear, damage, dirt, or other material or conditions which may obstruct the transmission of laser energy.

In one embodiment, illustrated in FIG. 3, the syringe 118 is a 60 cc syringe capable of dispensing saline solution, as discussed below. The syringe 118 includes a connector 118a that is threadably connectable with one end of the saline tube 114. The syringe 118 also includes a plunger 118b. The saline tube 114 includes two ends, one end of which is threadably connectable with the syringe 118, and the other end of which is threadably connectable with a port 104b of the hemostasis valve.

In an embodiment of the hemostasis valve illustrated in FIG. 3, the hemostasis valve is a y-shaped connector with three ports 104a, 104b, and 104c. Port 104a is configured to be connectable to the laser probe 100 such that when connected, the hemostasis valve 104 and the laser probe 100 share the same axis. Port 104b is configured to be connectable with an end of the saline tube 114. Port 104c is configured to accept the optical fiber 116 to enable the optical fiber 116 to be inserted in the hemostasis valve 104 and into the laser probe 100. In an embodiment, ports 104a and 104b for connection to the laser probe 100 and the saline tube 114, respectively, include connectors for threadably connecting the saline tube 114 to the hemostasis valve 104 and the hemostasis valve 104 to the laser probe 100. In one such embodiment, these connectors are configured to be hand-tightened by an operator prior to an interstitial laser treatment. In different embodiments, the hemostasis valve and the saline tube in different embodiments are constructed of an appropriate polymer suitable for transferring saline solution into a patient's body.

FIG. 4 illustrates an example layout of items contained in one embodiment of the interstitial laser therapy kit 300 as disclosed herein. In one embodiment, the interstitial laser therapy kit includes a laser probe 100, a thermal probe 102, an optical fiber 116, and two probe holders 50 and 52. In the illustrated embodiment, the interstitial laser therapy kit 300 also includes a rigid support structure 400 on which the laser probe 100, the thermal probe 102, the optical fiber 116, and the probe holders 50 and 52 are mounted as illustrated. In different embodiments, this support structure 400 may be constructed of plastic, cardboard, metal, or any other suitably rigid backing material.

In different embodiments, the items in the kit may include one or more sheaths 60a, 60b, and 60c made of plastic or another suitable material to protect the items during transportation and before use to perform interstitial laser therapy. In the illustrated embodiment, the laser probe 100 is protected by a plastic sheath 60a, the thermal probe is protected by a plastic sheath 60b, and the optical fiber is protected by a plastic sheath 60c. As further illustrated in FIG. 4, the probe holders 50 and 52 are contained in a plastic bag which is positioned on the support structure inside the container. It should be appreciated that in these embodiments, the support structure 400, the sheaths 60a, 60b, and 60c, and the plastic bag 62 prevent the items in the kit 300 from being damaged during transport and prevent the items from moving while in the container. In different embodiments, one or more of the The interstitial laser therapy kit 300 in various embodiments also includes a container (not shown). In one embodiment, the container includes a plastic bag, in which each of the above items illustrated in FIG. 4 is positioned before sterilization. In one such embodiment, the bag including the single-use items contained in the kit 300 and the support structure 400 is sterilized using known gamma radiation sterilization techniques. In different embodiments, the bag including the single-use items contained in the kit 300 is sterilized by chemical diffusion sterilization, such as ethylene oxide treatment, or by other suitable sterilization techniques. Once sterilized, the items in the kit 300 remain sterile until they are used to perform an interstitial laser treatment. The kit 300 in some embodiments is also marked so as to include kit identifiers such as a lot number, a serial number, and a control number of the kit 300. In different embodiments any suitable kit identifier may be included with the kit 300. As will be discussed below, this marking enables the microprocessor included in the computer 110 to track kits and ensure that certain items are not reused.

In alternative embodiments, the containers in which the items of the kit 300 are positioned are one of a latex bag, a plastic box, a metal box, or another container suitable to maintain the sterility of the items positioned within the container. In the above embodiments, the apparatus disclosed also includes instructions that instruct the operator to dispose of all the single-use items in the container when one of the items in the container is used to perform an interstitial laser treatment as disclosed herein. In alternative embodiments, these instructions are printed on the container in which the items in the kit 300 are positioned.

In alternative embodiments, two or more interstitial laser therapy kits of sterile, single-use items are required to successfully perform an interstitial laser treatment using the disclosed interstitial laser therapy apparatus. The first kit 300, illustrated in FIG. 4, includes a container in which the following sterile, single-use items are positioned:
  (i) one laser probe 100;
  (ii) one thermal probe 102;
  (iii) two probe holders 50 and 52; and
  (iv) one laser fiber 116.

The first kit preferably also includes one or more kit identifiers such as a lot number, a serial number, and/or a control number to uniquely identify the kit. In one embodiment, the numbers are printed directly on one or more of the items in the kit, including the container in which the single-use items are positioned. In a different embodiment, the kit identifiers are included within the kit by printing them on the support structure 400 or other suitable material.

The second kit includes at least one container in which one or more of the following sterile, single-use items are positioned:

(i) 1 vl Bupivacaine, 0.5% 50 mL (also known as marcaine);
(ii) 1 vl Lidocaine, 1% 10 ml;
(iii) 1 Syringe 1 cc TB 27×½ Safetyglide (initial injection of lidocaine);
(iv) 1 Syringe 5 cc L/L (additional injection of lidocaine if needed);
(v) 1 Syringe 20 cc F-L, green (marcaine);
(vi) 1 Syringe 60 cc F-L 118, white (saline);
(vii) 1 Needle 22×1½ regular beveled (additional injection of lidocaine if needed);
(viii) 2 Needles 18×1½ Safetyglide (saline syringe, marcaine injection);
(ix) 1 Saline tubing 114, 72" Male/Female Luer;
(x) 1 bt Saline irrigation, 100 ml;
(xi) 1 Accessplus Large Bore Hemostasis valve 104;
(xii) 1 Scalpel, #11 blade;
(xiii) 4 Gauze 4×4 12-ply;
(xiv) 1 Towel, 17×19", white;
(xv) 1 Biohazard bag, red 17×18; and
(xvi) 1 Twist tie.

In different embodiments, the second kit does not include kit identifiers, and the control system does not need to track the use of the single-use items in the second sterile kit. However, in the event a kit container is torn, opened, or the kit is of questionable sterility, the single-use nature of the kit enables the operator to discard the entire package and begin the interstitial laser treatment with another kit.

It should be appreciated that in different embodiments, the items in the interstitial laser therapy kit(s) are not disposable after a single use. In these embodiments, the operator returns the items in the kit(s) to the provider of the kit(s) to enable the items in the kit(s) to be re-sterilized and re-processed. In certain of these embodiments, the provider re-sterilizes the items, re-packages them in a container such as a non-resealable plastic bag, and provides a new unique kit identifier. It should be appreciated that regardless of whether the kit(s) are recyclable and/or reusable, the operator should not perform a second interstitial laser treatment without ensuring that the kits are properly sterilized and processed.

In one embodiment, in addition to the individual items contained in the kit(s) discussed above, the operator should have the following items available to ensure a successful interstitial laser treatment: (i) monitoring equipment for the patient's oxygen, blood pressure, and pulse; (ii) an oxygen cylinder or other oxygen supply; (iii) medication for resuscitation in case of cardiac failure; and (iv) a suction pump.

Performing Interstitial Laser Therapy Using the Apparatus and the Kit(s)

Figure 5:
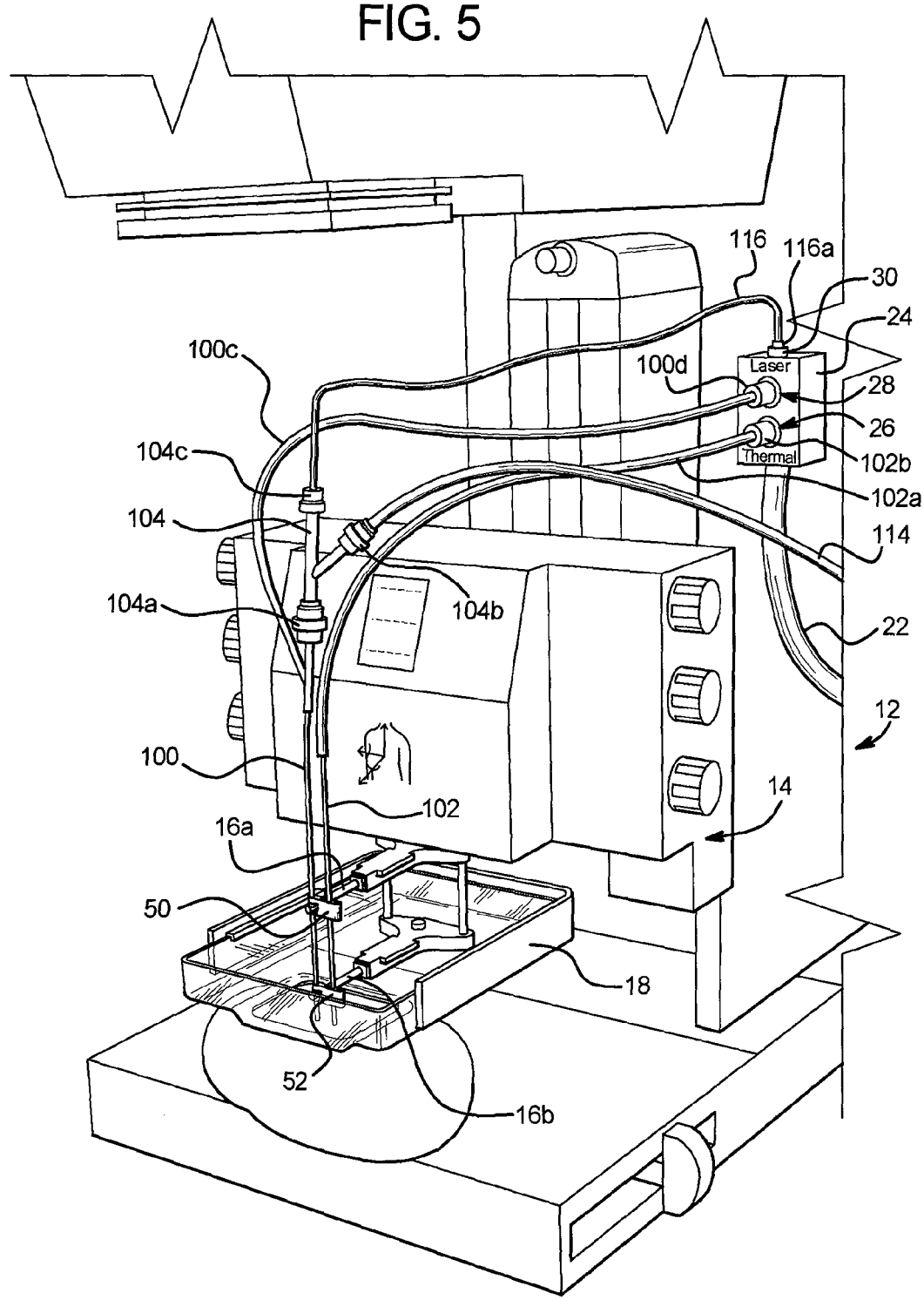
FIG. 5 is a fragmentary perspective view of one embodiment of the items in the interstitial laser therapy kit(s) disclosed herein positioned for use in conjunction with the mammography unit, the stereotactic device, and the interstitial laser therapy apparatus disclosed herein.

Referring now to FIG. 5, prior to performing an interstitial laser treatment, the operator obtains an unopened kit 300 as discussed above. In different embodiments, the operator obtains two or more different kits, each containing one or more of the sterilized items disclosed above. The operator also ensures that an interstitial laser therapy apparatus including the cart 20 and the umbilical assembly (including the umbilical cord 22 and the connector box 24) is available, and that a platform 12 including probe holder attachments 16a and 16b for performing the interstitial laser treatment is also available. In one embodiment, the umbilical assembly enables the operator to perform interstitial laser treatments with electrical and optical components of the interstitial laser therapy apparatus located nearby. In one embodiment, the operator places the wheeled cart 20 near the platform 12 such that the connector box 24 can be placed on or attached to the platform 12 while the umbilical cable 22 remains attached to the cart 20. In one embodiment, the operator affixes the connector box 24 to a Velcro patch or other suitable connecting material included on the platform 12.

The keyboard 208 and the mouse 206 enable the operator to enter the kit identifier such as the control number, serial number, and lot number associated with the kit 300 of single-use items into the control system, executed by a microprocessor contained in the computer 110. Prior to connecting any of the items to the interstitial laser therapy apparatus, the control system informs the operator whether or not the kit 300 is acceptable to use with the interstitial laser therapy apparatus to perform treatments.

In one embodiment, umbilical cable 22 is connected to an umbilical bracket (not shown) on the cart 20 prior to performing treatments. In a further embodiment, a thermistor wires cable connector is aligned with its female receptacle mounted on the cart wall. When properly aligned, the female receptacle enables the outer casing of the cable connector to be turned clockwise to screw the umbilical cable 22 onto the cart receptacle and fasten the it to the cart 20. After the thermistor wires cable is adequately connected to the cart 20, the operator removes the cap from the male end of the fiber optic cable included in the umbilical cable 22 and inserts the cable into the female fiber optic receptacle, also mounted on the cart 20 wall. These connections enable the connector box 24 to send and receive necessary electrical signals and optical energy to and from the components contained in the cart 20.

In one embodiment, the optical connector 30 on the connector box 24 includes a protective metal cap (not shown) that must be removed to enable the apparatus to be used to perform interstitial laser treatments. Leaving the protective metal cap on the optical connector 30 enables the enables the end of the umbilical optical fiber (not shown) to be kept clean and free of scratches, and to protect against accidental laser light emission.

In one embodiment, the operator removes the laser probe 100, the thermal probe 102, the optical fiber 116, and the probe holders 50 and 52 from the support structure 400 of the kit 300 and the hemostasis valve 104, the syringe 118, the saline tube 114 from the second kit of disposable items. The operator in one embodiment rotatably inserts the integrated bushing 50a and 52a of each of the probe holders 50 and 52 into one a hole in one of the probe holder attachments 16a and 16b. The operator then inserts the laser probe 100 into the holes 50b and 52b in the integrated bushings 50a and 52a or the probe holders 50 and 52 which enable such that the integrated bushing 50a and 52a, the holes in the probe holder attachments 16a and 16b, and the laser probe are co-axially aligned. The operator selects a desired channel 50c and 52c in the probe holders 50 and 52 in which to insert the thermal probe 102 based on the desired distance of the thermal probe 102 from the laser probe 100. The operator inserts the thermal probe 102 into the channels in the probe holders 50, 52. In different embodiments, the operator additionally adjusts the relative positioning of the probes 100 and 102 using the spaced-apart marks 102c that are included on the thermal probe 102 as a guide.

In different embodiments, the operator inserts the laser probe 100 into the tumor and the thermal probe 102 into the tissue adjacent to the tumor. The operator in one embodiment positions the patient with respect to the stereotactic imaging device 14 and inserts the laser probe 100 into the probe holders 50 and 52, through the probe holder attachments 16a and 16b, and into the center of the tumor in a substantially continuous motion. In this embodiment, the stylet 100b is positioned in the cannula 100a while the laser probe 100 is inserted into the tumor. The operator then inserts the thermal probe 102 in channels in the probe holders 50 and 52 and into the tissue adjacent to the tumor at a desired distance from the center of the tumor, again in a substantially continuous motion.

In another embodiment, the operator first inserts the laser probe 100 into the probe holders 50 and 52 and through the probe holder attachments 16a and 16b, but not immediately into the tumor. The operator similarly inserts the thermal probe 102 into the probe holders 50 and 52, but not into the tissue adjacent to the tumor. In this embodiment, the patient is positioned under the stereotactic imaging device 14 after the laser probe 100 and/or the thermal probe 102 are positioned in the probe holders 50 and 52. Once the patient is positioned with respect to the probes 100 and 102, the probes are inserted into the tumor and the tissue adjacent to the tumor such that the tip of the laser probe 100 is in the center of the tumor and the thermal probe 102 is a known distance away from the center of the tumor. It should be appreciated that in different embodiments, the operator inserts a biopsy needle in the probe holder attachments 16a and 16b prior to rotatably inserting the probe holders 50 and 52. In these embodiments, inserting the biopsy needle first creates a hole in the tissue which enables the laser probe 100 to be inserted into the previously-created hole. In the various embodiments discussed above, when the patient is positioned with respect to the stereotactic imaging device 14, it should be appreciated that the compression plates 18 enable the tissue surrounding the tumor (i.e., the breast) to be placed under compression. Appropriate apparatus such as a compression plate 18 of the stereotactic imaging device 14 ensure the tissue remains substantially stationary during insertion of the probes 100 and 102, and during treatment.

In one embodiment, the operator connects the laser probe connector 100d to the appropriate socket 28 in the connector box 24. The operator also connects the thermal probe connector 102b to the appropriate socket 26 in the connector box 24. Once the appropriate connections between the probes, the umbilical assembly, and the cart have been made, the operator initiates the calibration and testing functionality of the software installed on the computer 110 to ensure that the thermistors included on the laser probe 100 and the thermal probe 102 are functioning properly. The details of the software calibration procedure are disclosed below.

Once the laser probe 100 has been properly positioned in the tumor, the operator removes the stylet 100b from the cannula 100a. So removing the stylet 100b in one embodiment enables the operator to connect the hemostasis valve port 104a directly to the cannula 100a of the laser probe 100. The operator connects the hemostasis valve 104 to the laser probe 100 using the connector 104a on the hemostasis valve 104. In one embodiment, the hemostasis valve 104 is threadably connectable to the laser probe 100, and the operator screws the connector 104a onto the end of the laser probe 100 by hand until the connection is tight.

In one embodiment, the operator removes the cap from the optical connector 30 on the connector box 24 and the cap 116b from the optical fiber 116. The operator threadably connects the optical fiber 116 to the optical connector 30 using the included connectors. In this embodiment, the operator leaves the protective cap (not shown) on the other end of the optical fiber. The operator then causes the microprocessor to initiate the laser calibration process to ensure the laser source and all the connected optical cables are functioning properly. In different embodiments, the calibration is performed before the optical fiber 116 is threadably connected to the optical connector 30.

In one embodiment, the operator removes the cap from the end of the optical fiber without the connector 116a and inserts that end into the optical fiber port 104c on the hemostasis valve 104. This enables the optical fiber to be positioned within the laser probe 100 such that the tip of the optical fiber 116 is at the center of the tumor. It should be appreciated that in some embodiments, the optical fiber 116 is not inserted in the laser probe 100 until after it has been connected to the optical connector 30 of the connector box 24. In different embodiments, the operator does not insert the optical fiber 116 in the laser probe 100 until after the laser source and all connected optical fibers have been calibrated.

Figure 6:
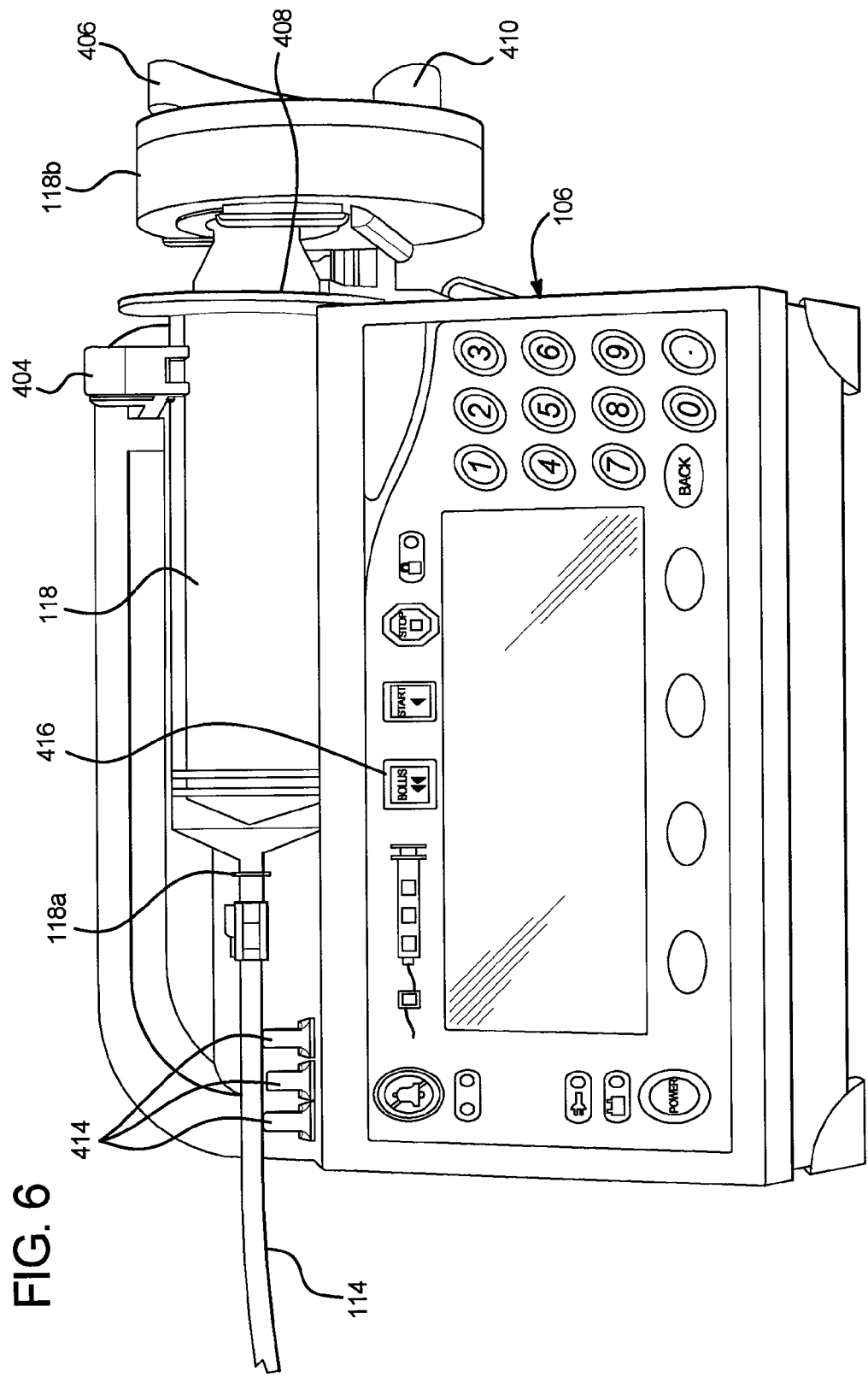
FIG. 6 is a fragmentary perspective view of one embodiment of the infusion pump of the interstitial laser therapy apparatus and the disposable syringe and syringe tube of the interstitial laser therapy kit(s) disclosed herein.

Referring to FIGS. 3, 5, and 6, an infusion pump 106 of the interstitial laser therapy apparatus supplies a constant rate of a solution containing 0.9% sodium chloride (i.e., standard saline). In the embodiment illustrated in FIG. 6, the infusion pump is the MEDFUSION™ 3500 infusion pump loaded with a 60 cc syringe 118. In one embodiment, the operator turns on the infusion pump 106 and specifies a delivery mode. The options for the specified delivery mode in one embodiment include volume/time, micrograms/hour, micrograms/minute, mg/hr, mg/minute, milliunits/hour, milliunits/minute, and/or units/hour. The operator inputs the type of syringe used into the infusion pump 106.

Using standard protocol, the operator in one embodiment prepares the syringe 118 by filling it with a 0.9% sodium chloride (i.e., standard saline) solution and attaching the saline tube 114 to the tip of the syringe 118a. The operator lifts and swivels the barrel clamp 404 and squeezes the plunger release lever 406 on the syringe plunger driver 408. The operator then pulls gently to extend the plunger driver 408 as far as possible. The operator then loads the syringe 118 onto the pump 106, making sure the flange of the syringe barrel is pressed or rolled into the flange clip 410. Squeezing the plunger release lever 406 on the end of the syringe plunger driver 408, the operator slips the end of the syringe plunger 118b into place. The operator then releases the lever 406 and makes sure that the syringe plunger 118b is adequately secured to the plunger driver 408. If so, the operator lowers the barrel clamp 404 onto the barrel of the syringe 118. The operator should thread the tubing 114 through the tubing holders 414.

After the syringe 118 is properly loaded, the operator in one embodiment specifies the infusion rate of the infusion pump 106. This is done by entering the rate into the infusion pump 106 and confirming the rate by pressing the enter key.

In one embodiment, prior to using the infusion pump 106/syringe 118 combination, the operator primes the system. To prime the system, the operator presses and holds the BOLUS button 416 while observing for fluid movement at the patient end of the system (i.e., saline emerging from the other end of the saline tube). Once the operator observes this fluid movement, the system is primed. Priming the system removes the mechanical slack in the pump and syringe, and significantly reduces the start-up time of the interstitial laser treatment.

In one embodiment, once the system is primed, the operator connects the saline tube 114 to the appropriate port 104b on the hemostasis valve. In this embodiment the saline tube 114 includes a connector threadably attachable to the hemostasis valve 104, so the operator hand-tightens the connector on the hemostasis valve 104. In one embodiment, after the saline tube 114 is connected to the hemostasis valve 104, the items contained in the kit 300 are appropriately configured with the stereotactic imaging device 14 and the interstitial laser therapy apparatus to enable interstitial laser treatment.

Indications for Treatment

In various embodiments, the interstitial laser therapy apparatus and kit(s) disclosed are intended to treat a benign fibroadenoma which is a tumor with a diameter of up to 2.0 cm; for performing general surgical procedures including incision, excision, and ablation of various soft tissues of interest; and for treating coagulative necrosis and performing interstitial laser coagulation of soft tissue.

In one embodiment, a prospective female patient detects a lump the her breast either by palpation or by mammography. In this embodiment, a physician makes a definitive diagnosis by ultrasound or by a stereotactic guided-needle core biopsy. If the lump is diagnosed as a fibroadenoma, the patient and/or the physician may elect to keep the lump under surveillance. However, if the lump does not begin to decrease in size or if it starts to become larger after an amount of time, or if the patient particularly desires that the lump be removed for fear of malignancy or for cosmetic reasons, the interstitial laser therapy apparatus and kit(s) enable minimally invasive, effective treatment of the fibroadenoma.

In various embodiments, patients are selected based in part on the following inclusion criteria: (i) the patients are females age 15 and older; (ii) the breast tumors are detected by physical examination or by imaging techniques such as mammogram or ultrasound (the tumor should be well defined on a mammogram or ultrasound prior to resorting to interstitial laser therapy); (iii) the physician makes a definitive histological diagnosis of that the treated tissue is benign (i.e., the tumor is diagnosed as a fibroadenoma); (iv) the tumor does not exceed 2.0 cm in diameter and is located at least 0.5 cm from the skin; and (v) the patient has a single or multiple fibroadenomas.

The following exclusion criteria can be applied to determine that a patient should not undergo interstitial laser treatment: (i) the patient is pregnant or lactating; (ii) the patient has been diagnosed with uncorrectable coagulopathy; (iii) the tumor or tissue cannot be clearly visualized by mammography or ultrasound; (iv) the tumor or tissue has equivocal histology (i.e., cystosarcoma, phylloides, atypia, or in-situ carcinoma); (v) the patient has significant concomitant diseases that could interfere with data analysis; and (vi) the patient has been diagnosed with physical or psychological disorders within the past five years that may be life-threatening.

The Interstitial Laser Therapy Control System

In one embodiment, an interstitial laser therapy control system for controlling and monitoring an interstitial laser treatment includes the microprocessor included in computer 110 which is operable to execute instructions stored on a memory device such as a hard disk connected to the computer 110. In this embodiment, the microprocessor is configured to enable the operator to manage patient records in a patient database stored on a hard disk or other memory device connected to the computer 110. The microprocessor is configured to operate with the thermistor controller to receive data indicating temperatures detected by the thermistors of the thermal probe and thermistors of laser probe. In different embodiments, the microprocessor is also configured to receive data from the thermistor controller indicating whether each thermistor on the laser probe and each thermistor on the thermal probe is functioning properly. The microprocessor monitors, displays, stores, and makes determinations based on the temperatures detected by the thermistors, as discussed in more detail below. The microprocessor is further configured to communicate with the laser source to control the amount of interstitial laser energy applied to the tumor. In some embodiments, to be discussed in more detail below, the microprocessor is configured send and receive signals from the laser source, which enables the microprocessor to make determinations to more accurately control an interstitial laser treatment.

The control system also includes various input devices such as a keyboard 208 and a mouse 206, and at least one display 112 for enabling an operator to input commands and data and to visually monitor the progress of an interstitial laser treatment. In different embodiments, the control system further includes a touch screen controller configured to be operable with the display 112 to enable an operator to provide input to the control system by touching the display 112.

In some embodiments, the control system includes at least three electro-mechanical buttons or switches, including a master power switch, a shutter switch, and an emergency shutoff switch. These electro-mechanical switches enable an operator to quickly and certainly stop the application of laser energy to tissue during interstitial laser treatment without regard for whether the microprocessor is responsive or functional.

Initiating the Hardware and Starting the Control System

Referring to FIG. 2, in one embodiment, the interstitial laser therapy apparatus includes a master power switch 200 and a backlit LED that glows red when the electrical and optical components of the interstitial laser therapy apparatus are receiving power. The backlit LED enables the operator to verify that the that the master power switch 200 is actuated by visually inspecting whether it is in the "on" position and whether the backlit indicator is glowing. In different embodiment, the master power switch 200 must be actuated and the backlit LED must be glowing prior to performing an interstitial laser treatment. In one embodiment, the electro-mechanical master power switch 200 is included in the control system and enables the operator to quickly and certainly prevent electricity from flowing to the electrical components. In this embodiment, actuating the master power switch 200 causes all the components included in the interstitial laser therapy apparatus to shut down, despite the presence of a UPS. In different embodiments, the UPS included in the interstitial laser therapy apparatus prevents the electrical components from shutting down in the event power in the procedure room is lost. In these embodiments, actuating the master power switch 200 similarly does not enable the operator to immediately prevent laser energy from being provided to the tumor, even if the operator actuates it to the "off" position.

After the master power switch 200 has been actuated such that it is in the "on" position, the computer power switch (not shown) enables the operator to turn on the computer 100. In one embodiment, to access the computer power switch the operator inserts the appropriate key into the lock 220, turns the key clockwise, and pulls. Actuating the computer power switch causes the microprocessor of the computer 110 to load an operating system, which in one embodiment is WINDOWS XP™ with at least Service Pack 2 installed. In this embodiment, the microprocessor operates with the keyboard to enable the operator to log into the computer 110 using a dedicated account created for use by physicians and physicians' assistants. In other embodiments, different user accounts exist to enable, for example, administrator or technical support personnel access.

Updating the Patient Database

Figure 7:
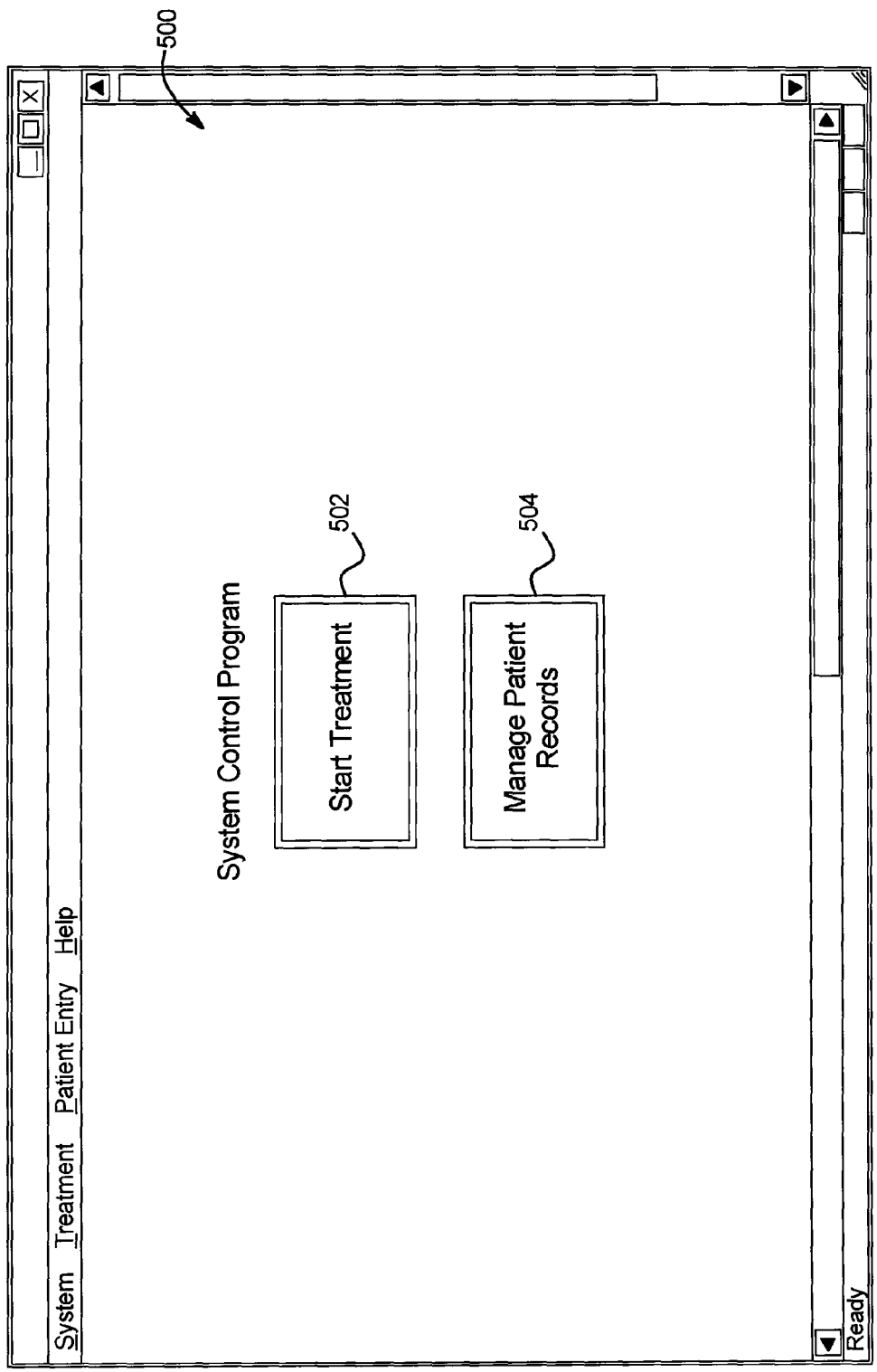
FIG. 7 is a screen shot of an example home screen window for performing interstitial laser therapy displayed by a Graphical User Interface (GUI) generated by an interstitial laser therapy control system.

FIG. 7 illustrates a screen shot of an example GUI generated and caused to be displayed by the control system. It should be appreciated that with respect to the GUI provided by the interstitial laser therapy control system, the term "select" refers to selecting an item displayed by the control system using the mouse 206, the keyboard 208, or another suitable input device such as a touch screen. In the embodiment illustrated in FIG. 7, when the operator has successfully logged in to the operating system of the computer 110, the control system generates Home Screen 500, which enables the operator to perform a plurality of tasks. In one embodiment, the Home Screen 500 enables the operator to select a Start Treatment button 502 to begin interstitial laser treatment, and enables the operator to select a Manage Patient Records button 504 to manage the records in the patient database stored one or more storage devices on computer 110.

Figure 8:
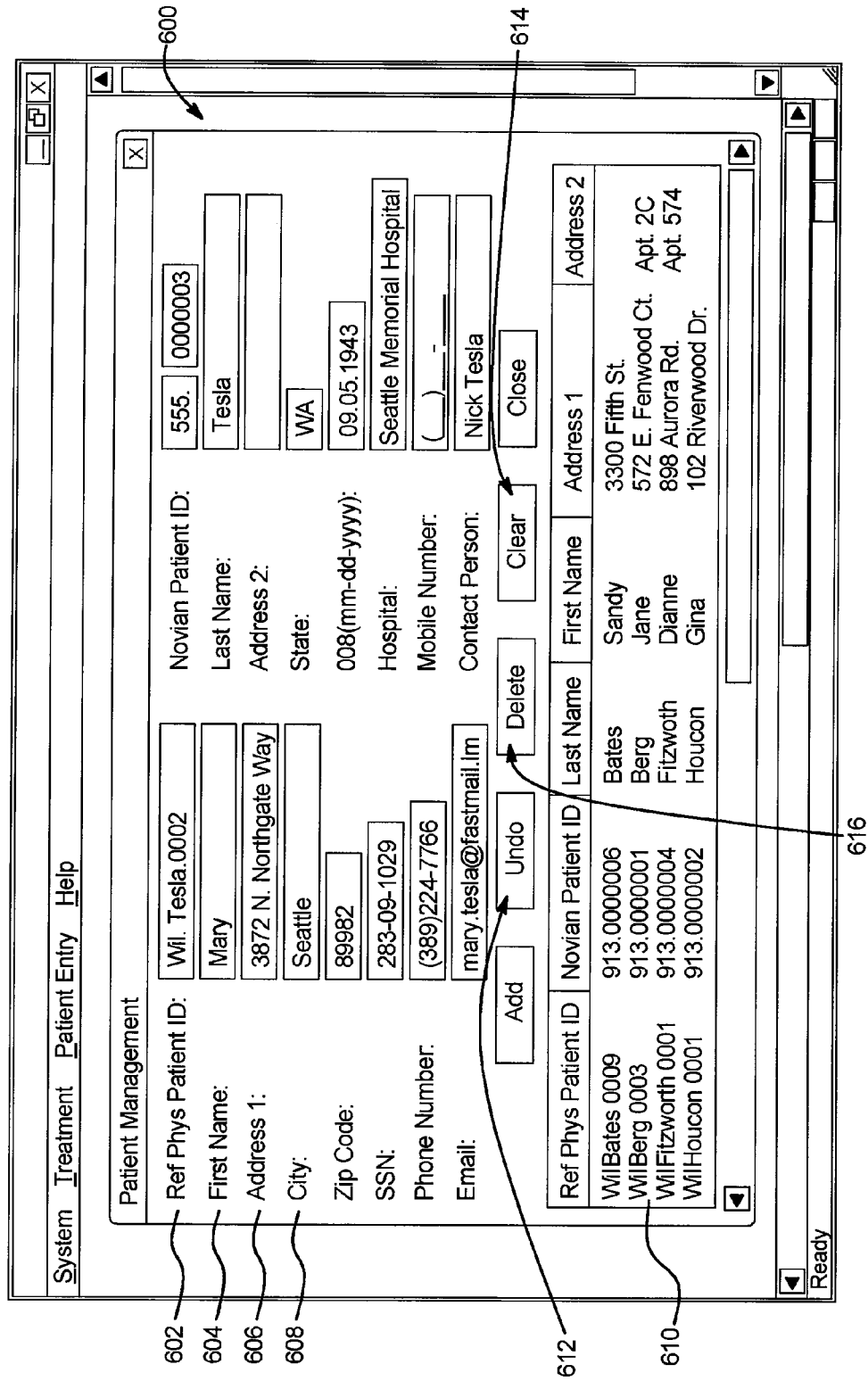
FIG. 8 is a screen shot of an example patient management screen which enables the operator to add, edit, or delete patient information according to the methods disclosed herein, displayed by the control system.

In one embodiment, a patient must be included in the patient database for the control system to enable the operator to initiate an interstitial laser treatment. Thus, in one embodiment, selecting the Manage Patient Records button causes the control system to generate a Patient Management Screen 600, as illustrated in FIG. 8. The Patient Management Screen 600 enables the operator to enter details about an existing patient in a plurality of editable fields (e.g. Ref Phys Patient ID 602, First Name 604, Address 1 606, or City 608) by selecting the appropriate row from a list of patients 610 managed by the control system. In one embodiment, the control system limits the data that can be entered to the types and number of characters for each of the data field as provided in Table 2 below, with certain data fields being required as indicated to create a valid patient record.

TABLE 2

| Field Name | Valid Input | Length | Required |
| --- | --- | --- | --- |
| Ref Phys Patient ID | All Characters | 50 Maximum | Yes |
| Operator Patient ID | Numbers | 6 Maximum | Yes |
| First Name | All Characters | 50 Maximum | Yes |
| Last Name | All Characters | 50 Maximum | Yes |
| Address 1 | All Characters | 50 Maximum | Yes |
| Address 2 | All Characters | 50 Maximum | No |
| City | All Characters | 50 Maximum | Yes |
| State | All Characters | 50 Maximum | Yes |
| Zip Code | Numbers | 5 or 9 | Yes |
| Date of Birth | Numbers (mmddyyyy) | 8 | Yes |
| Social Security Number | Numbers | 9 | Yes |
| Hospital | All Characters | 50 Maximum | No |
| Phone Number | Numbers | 10 | No |
| Cell Phone Number | Numbers | 10 | No |
| Email Address | Letters, Numbers, '.', '-', '_', '@' | 50 Maximum | No |
| Contact Person | All Characters | 50 Maximum | No |

In the embodiment illustrated in the Table 2, the control system requires an operator to populate a Referring Physician Patient ID field (labeled "Ref Phys Patient ID"). This field contains a physician-designated patient identifier. In one embodiment, the Referring Physician Patient ID field associates the patient with both the operator performing the interstitial laser treatment and the physician that referred the patient for treatment. In one embodiment, Operator Patient ID field stores a local patient identifier for each patient. In this embodiment, the Operator Patient ID includes two parts which together form a 6-digit number. The first portion of the Operator Patient ID indicates a three-digit location code indicating where the interstitial laser treatment occurred. The second portion of the Operator Patient ID identifies the patient by a unique patient identifier. It should be appreciated that in alternate embodiments, the control system accepts any suitable format of input for the Referring Physician Patient ID and Operator Patient ID fields sufficient to uniquely identify the patient according to the referring physician's record-keeping system and according to the operator's record-keeping system.

In one embodiment, the control system enables the operator to select an Undo button 612 to restore the data in a recently changed field to the data contained in that field at the time the database record was last stored. In this embodiment, selecting the Clear button 614 enables the operator to cancel all changes and reset the control system so as to display the Patient Management window 600 of the GUI. Selecting the Delete button 616 causes the control system to mark the patient record as inactive. When a record is marked as inactive, it is no longer visible in the GUI but remains stored in a database record maintained by the control system on a storage device in the personal computer. In this embodiment, patient data, once entered, is never lost.

Configuring the Control System and Calibrating the Hardware

After the interstitial laser therapy apparatus has been appropriately combined with the interstitial laser therapy kit as disclosed, and after a patient record about the patient to be treated has been created, the control system in one embodiment enables an operator to perform an interstitial laser treatment. The operator initiates the treatment sequence by selecting the Start Treatment button 502 on the GUI Home Screen 500, illustrated in FIG. 7. When the operator selects the Start Treatment button 502, the control system generates a signal which is sent to the laser source 108 to turn on the laser source 108, though the signal commands the laser source 108 to not initially emit laser energy. In one embodiment, a red LED 218 above the laser startup key glows to indicate that the laser source 108 has been turned on. It should be appreciated that in the embodiment illustrated in FIG. 2, the laser startup key 210 enables the control system to turn on the laser source 108— that is, the laser startup key 210 must be inserted and properly turned, and the red emergency stop button 204 on top of the cart 20 must be raised to its "on" position, for electricity to flow to the laser source 108.

The control system in one embodiment displays a screen that enables the operator to select a patient for treatment (not shown). In one embodiment, the control system provides the operator a list of patients having records stored in the database, and enables the operator to select one of the patients. In this embodiment, if the operator does not select a patient (i.e., the operator tries to perform an interstitial laser treatment on a patient not in the database), the control system prevents the operator from performing interstitial laser treatment.

Figure 9:
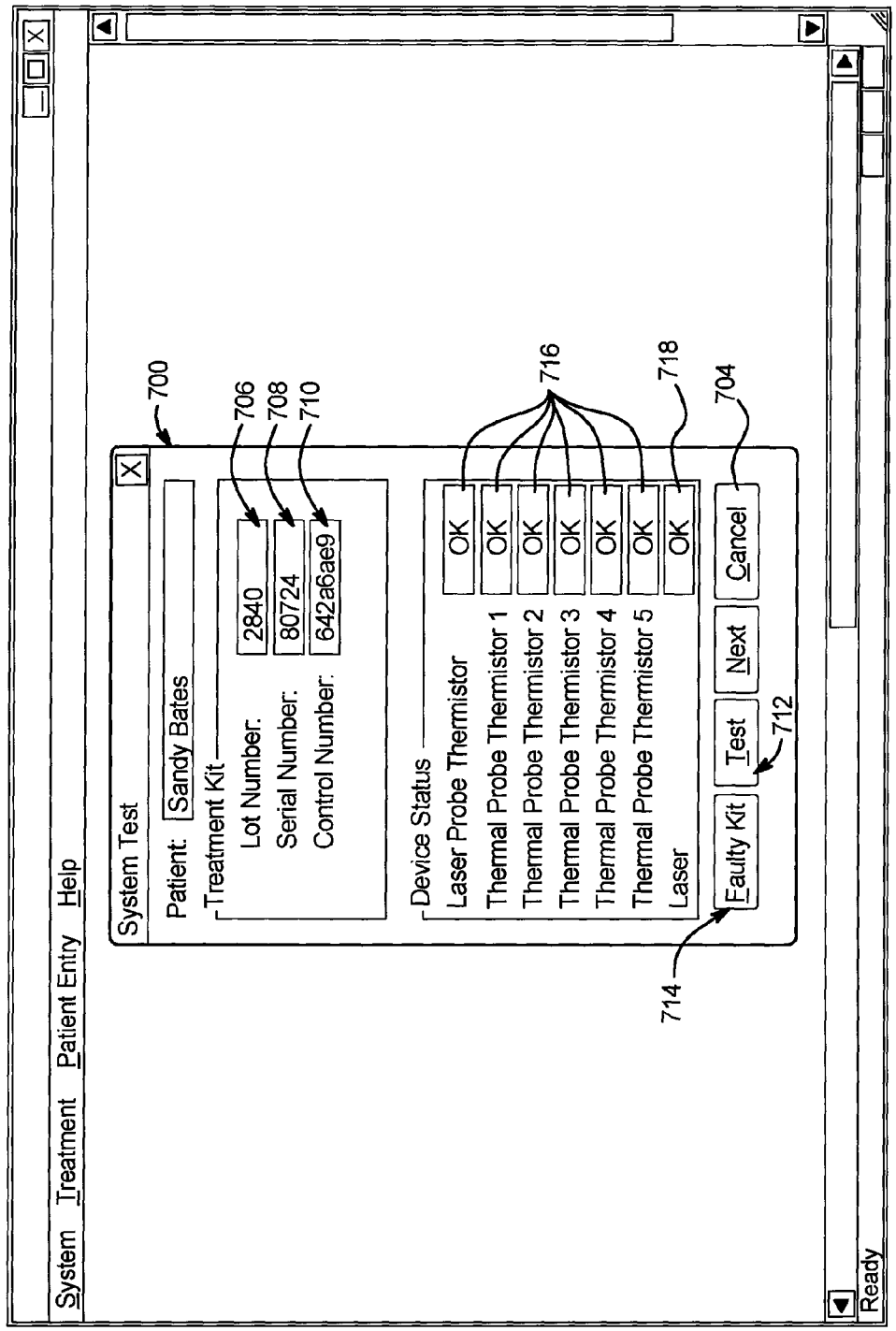
FIG. 9 is a screen shot of an example system test screen displayed by the control system, which indicates that the interstitial laser therapy kit being used to perform an interstitial laser treatment is valid, and which indicates that the laser probe, the thermal probe, and the laser source are functioning properly.

As discussed above, in one embodiment each interstitial laser therapy kit 300 may be used only once. In one embodiment, each kit 300 includes at least one kit identifier including control numbers, serial numbers, and/or lot numbers printed on the plastic bag in which the single-use items are contained. To verify that the kit 300 being used is valid, the control system generates and displays a System Test window 700 as illustrated in FIG. 9. The System Test window enables the operator to enter the lot number 706, the serial number 708, and the control number 710 associated with the kit 300.

In one embodiment, after the operator has entered the appropriate information identifying the kit 300, the control system enables the operator to select a Test button 712. The control system then verifies that the kit 300 being used in conjunction with the interstitial laser therapy apparatus has not been used before. In different embodiments, if the microprocessor detects that the kit has already been used, the control system displays a popup window instructing the operator to dispose of the items in the kit 300. In one such embodiment, the microprocessor determines whether the kit identifier indicates a valid kit based on data stored on a memory device of the computer 110 about past used kit identifiers. In a different embodiment, the kit identifier is generated by an algorithm, and the microprocessor determines whether the kit identifier is valid by applying the algorithm in reverse to the provided kit identifier. In still another embodiment, the microprocessor is configured to communicate with a server (not shown) or another computer 110 by way of the Internet or other suitable network. In this embodiment, the microprocessor included in the computer 110 communicates the kit identifier entered to the server or other computer 110 by way of the Internet or other suitable network, and the server or other computer 110 determines whether the valid kit identifier has been previously used on the on the server or other computer 110. The server then communicates with the microprocessor to indicate whether the kit is valid. It should be appreciated that in this embodiment, the control system prevents multiple uses of an interstitial laser therapy kit in two different locations even though the algorithm discussed above may indicate that the kit identifier is valid in both locations.

Referring still to FIG. 9, in one embodiment, selecting the Test button 712 also causes the control system to begin internal testing and validation of the probes and laser. In one embodiment, internal testing and validation includes the following activities: (i) verifying that the physical connections between the thermistor controller the thermistors of both probes 100 and 102 are continuous and provide a good communication path; (ii) verifying that the thermistor of the laser probe 100 and each thermistor of the thermal probe 102 are functioning properly; and (iii) verifying that the laser source 108 is calibrated and functioning properly. In one embodiment, the seven status fields 716 and 718 (i.e., one status field for each of the six thermistors and one status field for the laser) indicate that the associated device is functioning properly. As displayed in System Test screen 700, the control system indicates that the Device Status is OK by displaying an appropriate message.

If the status field associated with any of the six thermistors 716 indicates that the thermistor failed validation, the control system in one embodiment indicates the failure by displaying an appropriate message. In one embodiment, the message additionally instructs the operator to verify that the probes are plugged in to the proper sockets 26 and 28 of the connector box 24 and that the connectors 100*d*, 102*b* are adequately tightened. In some embodiments, the control system instructs the operator to verify that the umbilical cable 22 is correctly connected to the cart 20. In one embodiment, the control system enables the operator to re-run the various status tests by re-selecting a Test button 712 displayed in the System Test window 700. This restarts internal testing and validation. If the control system is unable to suggest an action that successfully resolves the indicated failures, the control system in one embodiment instructs the operator to select the Faulty Kit button 714 in the System Test window, select a new interstitial laser therapy kit, and enter the new lot number 706, serial number 708, and control number 710. It should be appreciated that the data contained in the lot number field 706, the serial number field 708, and the control number field 710 represent one embodiment of the kit identifier included in the kit 300 as discussed above.

If the laser status field 718 does not indicate a value of OK, the control system in one embodiment instructs the operator to verify that the red LED 218 above the key on the front of the laser source 108 is illuminated, indicating the laser source 108 is powered on and that the red emergency shutoff button 204 on top of the cart 20 is in the "on" position. In one embodiment, the control system enables the operator to select the Test button 712 again to perform internal testing and validation. If the control system still unsuccessfully validates and calibrates the laser, the control system prevents the operator from using the interstitial laser therapy apparatus to perform an interstitial laser treatment.

In one embodiment, the control system enables the operator to cancel treatment at any time by selecting a Cancel button 704. If the operator selects the Cancel button 704 after the internal tests have started but before the treatment is begun, the control system enables the operator to indicate that the kit 300 is adequate for reuse. If the operator indicates the kit 300 is acceptable for reuse, the control system does not store a record that the kit identifiers associated with the kit have already been used, so future attempts to use the kit identifiers will be successful.

Figure 10:
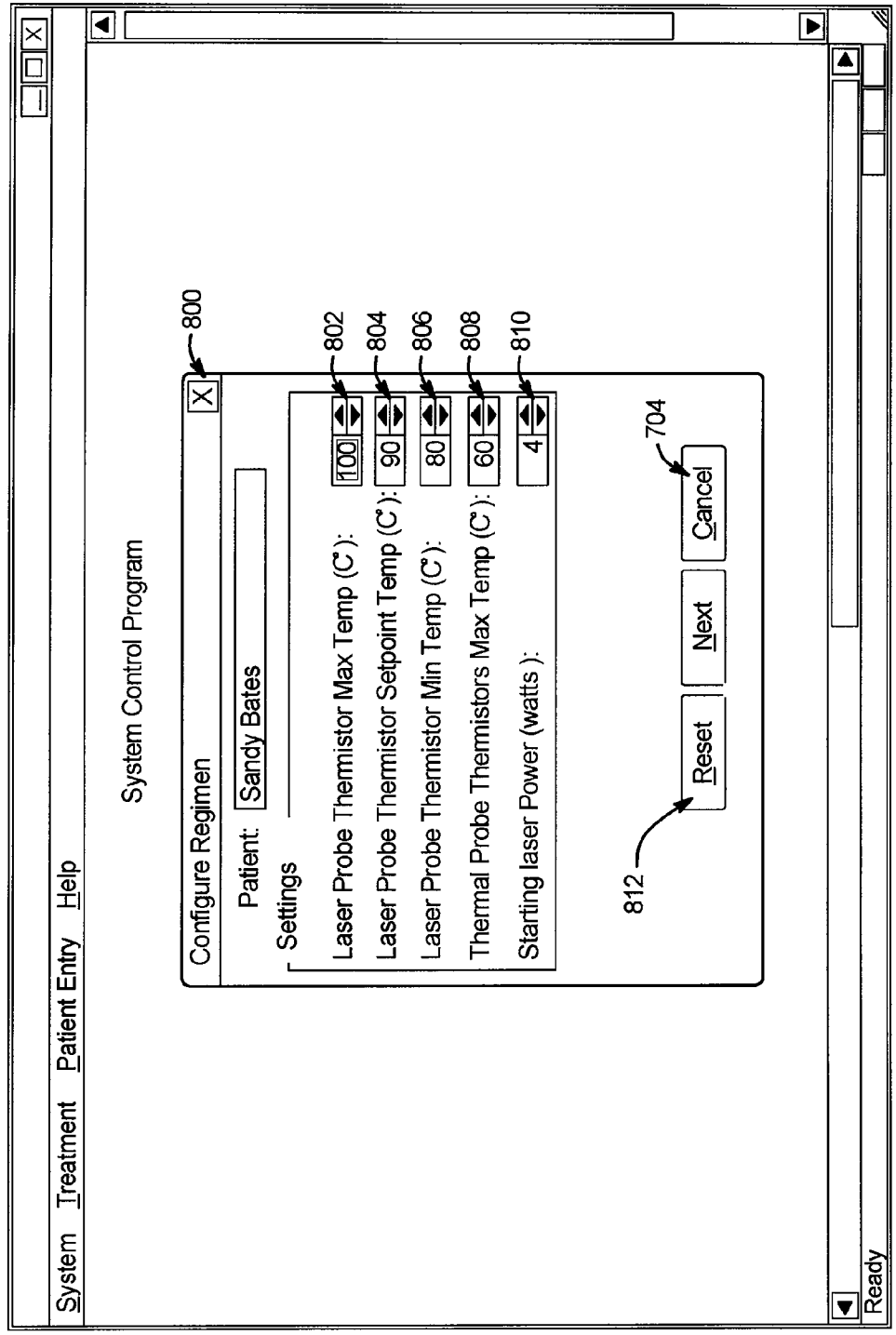
FIG. 10 is a screen shot of an example configure regimen screen displayed by the control system which illustrates the configurable parameters that the control system enables the operator to change prior to each interstitial laser treatment.

Referring to FIG. 10, once validation of the items in the kit is successful, the control system in one embodiment displays a Configure Regimen window 800 which enables the operator to change various parameters 802, 804, 806, 808, and 810 to be applied during the interstitial laser treatment. The definable parameters used in one embodiment by the control system to perform an interstitial laser treatment, a description of the parameter, the range of acceptable values, and a suggested default value are indicated in Table 3. It should be appreciated that the suggested default values included in Table 3 represent suggestions; in different embodiments operators choose values that are approximately equal to the suggested default values depending on the details of the treatment being performed.

TABLE 3

| Parameter | Definition | Valid Range Of Values | Suggested Default Value |
| --- | --- | --- | --- |
| Laser Probe Thermistor Max Temp 802 | The Celsius temperature of the thermistor of the laser probe, which, if reached, automatically terminates the treatment. Reaching this temperature is undesirable and does not imply successful treatment. | 0-110° C. | Approximately 100° C. |
| Laser Probe Thermistor Setpoint Temp 804 | The optimal treatment Celsius temperature of the thermistor of the laser probe. | 0-100° C. Must be less than or equal to Laser Probe Thermistor Max Temp. | Approximately 90° C. |

TABLE 3-continued

| Parameter | Definition | Valid Range Of Values | Suggested Default Value |
|---|---|---|---|
| Laser Probe Thermistor Min Temp 806 | The minimum Celsius temperature of the thermistor of the laser probe that insures adequate heating of the tumor. | 0-100° C. Must be less than or equal to Laser Probe Thermistor Setpoint Temp. | Approximately 80° C. |
| Thermal Probe Thermistor Max Temp 808 | The Celsius temperature that all five thermistors of the thermal probe must reach to automatically terminate treatment. Reaching this temperature implies successful treatment. | 0-100° C. Must be less than or equal to Laser Probe Thermistor Setpoint Temp. | Approximately 60° C. |
| Starting Laser Power 810 | The initial power setting of the laser, in watts. | 1-8 W. | 4 W |

In one embodiment, the control system uses additional system parameters defined by a system administrator and not modifiable by the operator. In one embodiment, a Thermal Probe Thermistor Warning Threshold parameter defines the temperature at which a bar indicating the temperature of a thermistor of the thermal probe 102 changes from a normal color to warning color (i.e., from green to yellow), as a percentage of Thermal Probe Thermistor Max Temperature. The Thermistor Treatment Ready parameter defines the minimum temperature that all thermistors must reach before the control system enables the operator to select a Start Treatment button. The Maximum Bad Thermal Probe Thermistor Limit parameter defines the maximum number of thermal probe thermistors that must be faulty before the control system automatically terminates treatment.

Figure 11:
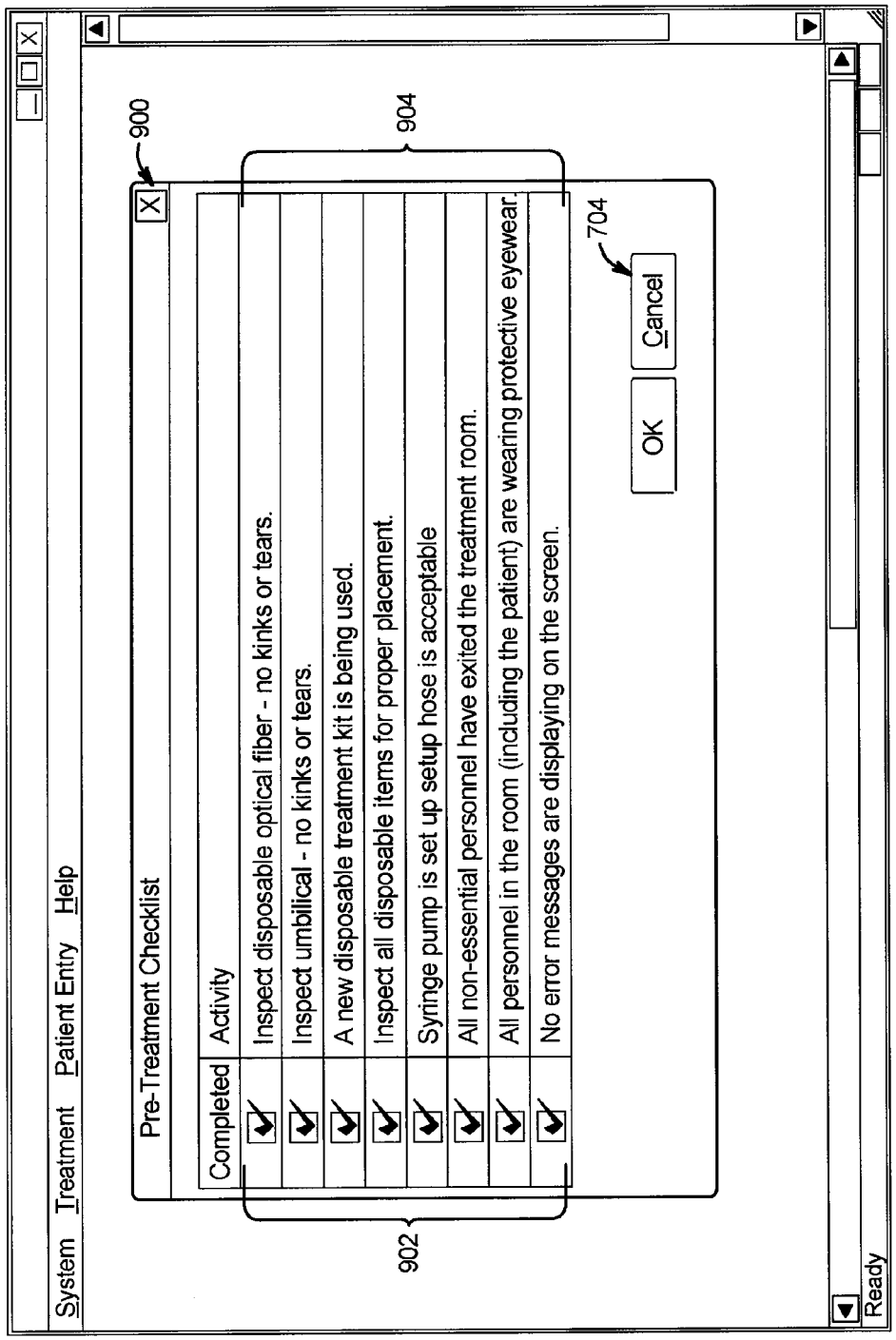
FIG. 11 is a screen shot of an example pre-treatment checklist screen displayed by the control system, which illustrates that the operator has performed all the pre-treatment activities required to perform an interstitial laser treatment.

Referring to FIG. 11, after the operator has inputted the required default values, the control system ensures that the appropriate pre-treatment tasks have been performing by displaying a Pre-Treatment Checklist window 900. The control system enables the operator to place a check mark in a box 902 when each pre-treatment checklist item 904 has been completed. In one embodiment, the control system does enable the laser source 108 to emit laser energy until the operator has performed each pre-treatment checklist item 904 and placed a check mark in the corresponding box 902.

Prepare the Patient

Once the control system has indicated that the interstitial laser therapy apparatus and kit(s) are functioning properly, the operator measures and records the dimensions of the tumor using the patient's most recent diagnostic mammograms and ultrasound images. The operator determines the shortest skin-to-target route that provides optimal visualization of the tumor while avoiding any intervening vessels from the same mammograms and images. It should be appreciated that in different embodiments, blood vessels and/or other tissue features act as heat sinks. Thus, when a blood vessel is located near a tumor to be treated, the blood vessel in different embodiments transfers heat away from the tissue. In these embodiments, if the thermal probe is placed near the blood vessel, the temperatures detected by the thermistors in the thermal probe are inaccurate because the heat energy applied to the tumor is not all dissipating in the tissue adjacent to the tumor. Thus, in one embodiment, the shortest skin-to-target route should take into account the location of intervening vessels to enable accurate temperature readings.

Based on the determined points of entry, the patient in one embodiment is positioned on a stereotactic table and the breast to be treated is immobilized in the compression plates 18. The breast is immobilized such that the target tumor is in the center of the operating window of the compression plates 18. Once the patient is appropriately positioned, the operator sterilizes the skin with alcohol and anesthetizes the skin with appropriate anesthesia (e.g. 1% lidocaine, included in the single-use items kit 300). Sufficient anesthesia is applied to the area around the tumor to fully encompass the treatment zone.

In one embodiment, the operator uses the stereotactic table to take stereotactic images. From these images, the operator determines coordinates of the center of the tumor and a point immediately adjacent to the tumor. In some embodiments, the operator performs one or more core biopsies for future reference and/or to create a path for insertion of the laser probe 100. Before inserting the probes into the tumor, a metal clip marker (not shown) in one embodiment is inserted into the breast immediately adjacent to the tumor for future reference.

In one embodiment, the operator rotatably inserts the probe holders 50 and 52 into the probe holder attachments 16a and 16b and inserts the laser probe 100 into the appropriate channels in the probe holders. Once the cannula 100a and stylet 100b have been appropriately inserted in the tumor, the operator removes the stylet 100b from the cannula 100a and replaces it with a hemostasis valve 104 and an optical fiber 116. The hemostasis valve 104 is connected to the laser probe 100 by finger-tightening the laser probe connector 104a. The operator connects the optical fiber 116 to the optical connector 30 on the connector box 24 after removing the protective cap from the optical fiber 116. The operator then inserts the optical fiber 116 into the optical fiber port 104c on the hemostasis valve 104 such that the tip of the optical fiber is inside the laser probe 100. In different embodiments, the tip of the optical fiber extends in the laser probe 100 until it is even with the end of the laser probe 100 inserted in the tumor mass. It should be appreciated that if the tip of the optical fiber 116 extends beyond the end of the laser probe, the interstitial laser treatment may be less effective because laser energy does not dissipate as efficiently as if the optical fiber 116 is properly aligned. In different embodiments, therefore, the optical fiber is configured to extend beyond the tip of the laser probe 100 and to efficiently radiate heat energy in the tumor mass. The operator also connects the saline tube 114 to the saline tube connector 104b on the hemostasis valve 104. During treatment, the tip of the optical fiber 116 is irrigated with normal saline solution provided through the saline tube 114 at a rate of between 1 and 2 cc per minute provided by the infusion pump 106. In one embodiment, the saline is para-axially infused along the optical fiber 116 and into the tumor.

The thermal probe 102 in one embodiment is inserted through the probe holders 50 and 52 and into the breast astride and parallel to the laser probe 100 such that the distance from the laser probe 100 is known. In one embodiment, the thermal probe 102 is inserted through a thermal probe channel 50c or 52c in each of two probe holders 50 and 52 such that the thermal probe's 102 distance from the laser probe 100 is easily ascertainable. The probe holders enable the operator to determine the distance between the probes based on the discretion of the operator and the analysis of the desired zone of ablation. In one embodiment, the holes in the probe holders 50 and 52 enable the thermal probe 102 to be positioned 5 millimeters, 7.5 millimeters, or 11 millimeters from the center of the laser probe 100.

In one embodiment, the operator generates a second set of stereotactic images to confirm appropriate positioning of probes 100 and 102 with respect to the tumor and with respect to each other. In one embodiment, after the probes 100 and 102 are appropriately positioned, the operator injects additional anesthetic into the area around the tumor 1 to ensure field anesthesia during interstitial laser treatment. In one embodiment, the additional anesthetic is 30-40 cc of 0.5% bupivacaine HCl (MARCAINE®), provided in the interstitial laser therapy kit 300.

The operator monitors the patient's vital signs and ensures comfort on the table before commanding the control system to begin interstitial laser treatment. Oxygenation is monitored with a pulse oxymeter throughout the treatment. The patient's blood pressure and pulse are also checked periodically. In one embodiment, a coolant fluid spray (preferably ethylene chloride) is available to cool the skin around the entry point of the laser probe 100 if any backflow of heated saline solution occurs.]

Monitoring Treatment Using the Control System

In one embodiment, the control system causes the display of various indications on the display 112 connected to the microprocessor during treatment that enable the operator to monitor an interstitial laser treatment and determine whether and when to stop treatment. The control system monitors the thermistor temperatures detected by the thermistor controller to automatically determines whether additional laser energy, less laser energy, or no laser energy (i.e., that treatment should be stopped) should be applied.

It should be appreciated that in the various figures described below, if a button provided in the GUI of the control system is outlined by two solid lines, the button is selectable by the operator using an input device such as a mouse 206 or a keyboard 208. If the button is outlined by a single solid line, the button is not selectable. Referring now to FIGS. 12, 13, 14, and 15, the control system displays a treatment window 1000 that displays the laser power being utilized 1002, the delivered energy 1004, the elapsed time of treatment 1006, and various parameters defined previously by the operator 1008. In one embodiment, the displayed parameters 1008 include the Laser Probe Maximum Temperature, the Laser Probe Setpoint Temperature, the Laser Probe Minimum Temperature, and the Thermal Probe Maximum Temperature. Additionally, the control system displays a thermistor temperature chart 1001 including the temperature detected by each thermistor of each probe. In one embodiment, this information is displayed as a bar graph with six bars, wherein one bar represents the temperature detected by each of $T_L$ (1010), $T_1$ (1012), $T_2$ (1014), $T_3$ (1016), $T_4$ (1018), and $T_5$ (1020). The control system receives real-time data from the thermistor controller and updates each bar as data is received, enabling the operator to quickly determine the temperatures detected by each thermistor.

In different embodiments, the control system displays a Start Treatment button 1050 and a Stop Treatment button 1052. In one embodiment, not shown, the Start Treatment and Stop Treatment buttons are not selectable before the temperature readings indicated for each of the thermistors has reached an appropriate minimum temperature. In one embodiment, illustrated by FIG. 12, the control system enables the operator to select the Start Treatment button 1050 of the treatment screen 1000 after each thermistor indicates a detected temperature at or near body temperature. In different embodiments, the temperature at or near body temperature is between 32° C. and 39° C. In one such embodiment, the temperature to enable treatment to begin is approximately 35° C. The control system ensures that treatment cannot be started before the thermistors detect such a temperature as a safety mechanism, as it is dangerous to emit laser energy when the probes are at room temperature (i.e., the probes have not yet been inserted, so any laser energy emitted would not be directed into the tumor).

Figure 12:
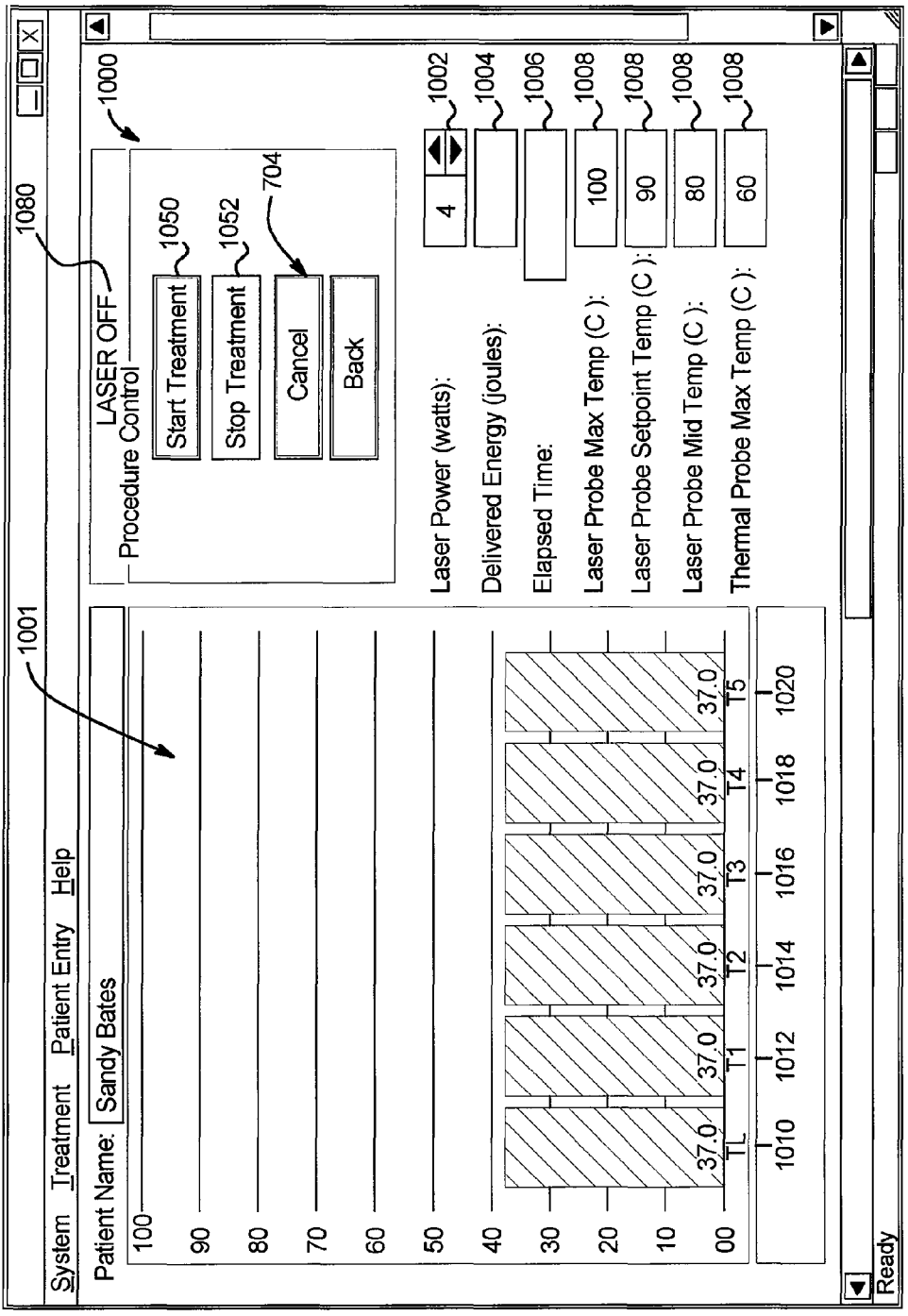
FIG. 12 is a screen shot of an example interstitial laser treatment screen displayed by the control system which illustrates that the thermistors inserted in the tumor mass or in tissue adjacent to the tumor mass must detect a temperature near the temperature of the human body before the control system enables the operator to begin interstitial laser treatment.

FIG. 12 illustrates that the temperature detected by each of the thermistors $T_L$, $T_1$, $T_2$, $T_3$, $T_4$, and $T_5$ is 37° C., as indicated by bars 1010, 1012, 1014, 1016, 1018, and 1020. Therefore, the control system enables the operator to select the Start Treatment button 1050 and emits an audible beep to indicate that interstitial laser therapy may be started. In different embodiments, the control system enables an operator to begin an interstitial laser treatment even if one or more thermistors of either the laser probe 100 or the thermal probe 102 does not measure a resistance indicating a temperature at or near body temperature. In these embodiments, the control system does not provide a temperature-based mechanism to determine whether the probes are inserted in a tumor mass and tissue adjacent to the tumor mass before generating laser energy—the operator in these embodiments determines whether the probes are appropriately placed before beginning treatment. Before the treatment has begun, and at any time during treatment when the laser source 108 is not emitting laser energy, the control system displays a LASER OFF message in status box 1080. In one such embodiment, the status box 1080 continuously displays messages indicating the current status of the laser.

The laser source begins emitting laser energy when an operator selects the Start Treatment button 1050. After the Start Treatment button has been selected, the control system in one embodiment displays a popup window directing the operator to start the infusion pump 106 (not shown). The operator indicates the infusion pump is running by selecting an OK button displayed by the control system. Once the control system has determined that the infusion pump 106 is running, it sends a signal to the laser source 108 to begin treatment. In different embodiments, the control system is additionally configured to communicate with the infusion pump 106 to determine whether saline solution is being delivered to the laser probe 100. In these embodiments, the control system does not generate and display a popup window asking the operator whether the infusion pump 106 is running.

In one embodiment, not shown, the status bar 1080 displays a message of LASER INITIALIZING prior to the laser source 108 emitting laser energy. In this embodiment, the control system sends a command to the laser source 108 to begin emitting laser energy based on an operator selecting the Start Treatment button described above, and during initialization the laser source 108 emits a plurality of audible beeps over the course of a few seconds (as mandated by FDA regulations).

Figure 13:
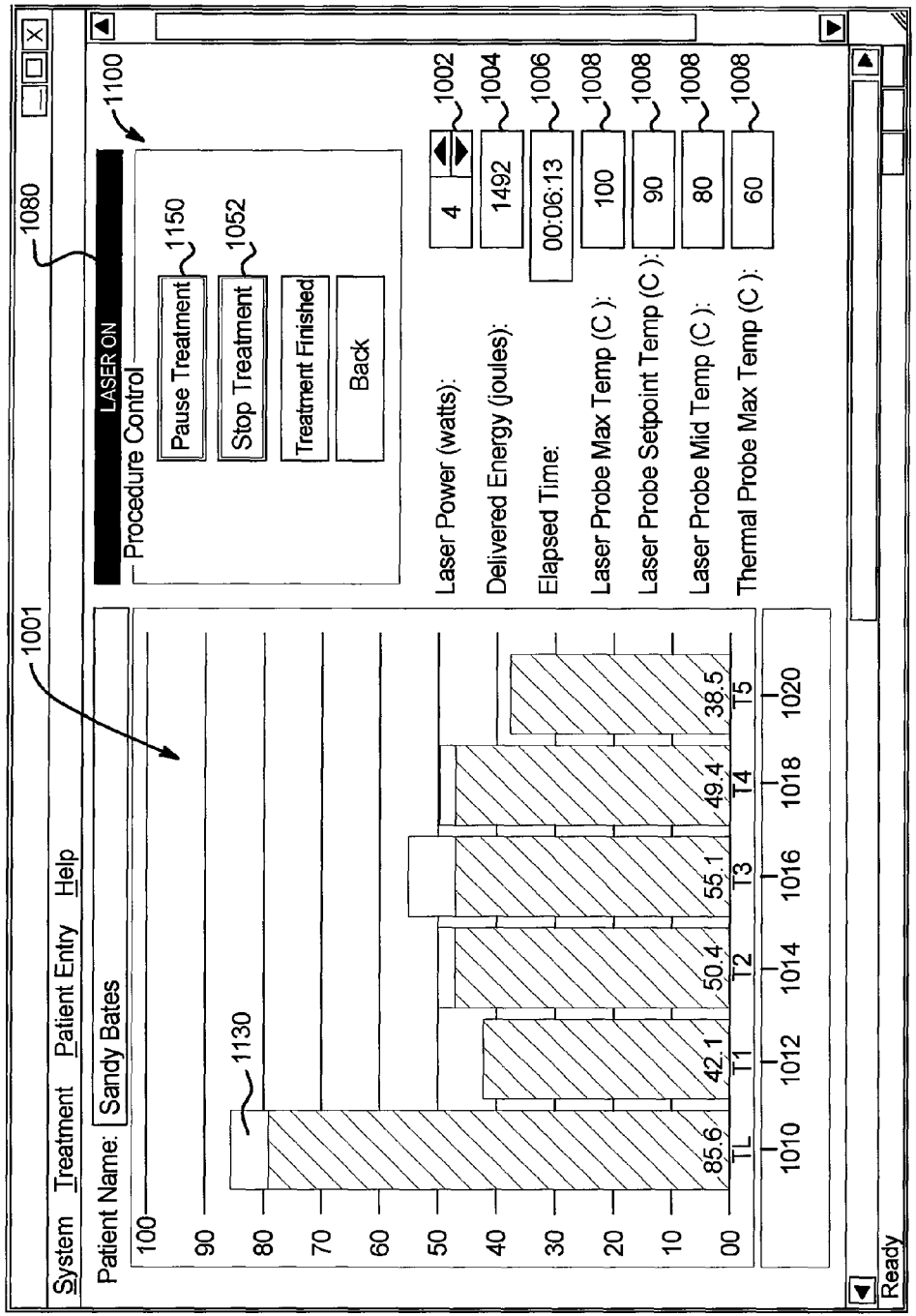
FIG. 13 is a screen shot of an example interstitial laser treatment screen displayed by the control system, which illustrates that at least one of the thermal probe thermistors is nearing the maximum allowed thermal probe temperature and that the laser probe thermistor is detecting optimum interstitial laser treatment temperatures.

In one embodiment, illustrated in FIG. 13, after an interstitial laser treatment has begun, the control system displays a treatment window 1100 including a Pause Treatment button 1150 where the Start Treatment button 1050 had been, enabling the operator to pause treatment by selecting the button. In one embodiment, the control system displays a red flashing LASER ON message in the status bar 1080 and the laser source 108 begins emitting laser energy. During treatment, the control system monitors the temperatures detected by the various thermistors of the laser probe 100 and the thermal probe 102 displays the temperatures as bars 1010, 1012, 1014, 1016, 1018, and 1020 in a thermistor temperature chart 1001. In one embodiment, the control system enables the operator to select the Stop Treatment button 1052 during application of laser energy to stop treatment altogether. In different embodiments, selecting the Stop Treatment button 1152 during treatment causes the control system to cease applying laser energy and to prevent treatment from being resumed. In one such embodiment, selecting the Stop Treatment button 1152 also causes the microprocessor to store an indication on the memory device that the interstitial laser therapy kit used to perform the treatment is no longer valid for use, and to store an indication that the treatment was not completed successfully.

Referring still to FIG. 13, in one embodiment, while the laser source 108 is emitting laser energy (and the status bar 1080 displays a flashing LASER ON message), the laser source and/or the control system emits an audible beep approximately every 10 seconds. In some embodiments, during application of laser energy, the control system continuously updates the bars 1010, 1012, 1014, 1016, 1018, and 1020 on the thermistor temperature chart 1001, representing the temperature readings indicated by $T_L$, $T_1$, $T_2$, $T_3$, $T_4$, and $T_5$, respectively. In different embodiments, the control system populates and continuously updates the values displayed in the Elapsed Time indicator 1006 and the Delivered Energy indicator 1004. In one embodiment, the control system records an entry in the database every second during treatment, wherein each record indicates Laser Power 1002, Elapsed Time 1006, Delivered Energy 1004, and each of the six temperature readings 1010, 1012, 1014, 1016, 1018, and 1020.

In one embodiment, over the course of a successful interstitial laser treatment, the control system displays temperatures for thermistors $T_1$-$T_5$ in the general shape of a bell curve as illustrated by the thermistor temperature chart 1001 of FIG. 13. In one embodiment, the thermistor $T_3$ indicates the highest temperature of the thermal probe thermistors. In such an embodiment, thermistor $T_3$ indicates the highest temperature of the thermal probe thermistors because it is positioned closest to the center of the tumor, and therefore closest to the site where the laser energy is being delivered.

In different embodiments, the control system displays the thermistor temperature of one or more thermistors as a different color when the thermistor temperature exceeds certain temperatures. In one embodiment, the thermistor temperatures are indicated as green bars (represented by low-left to high-right cross-hatching) at relatively low temperatures. In this embodiment, the thermistor temperatures are indicated as yellow bars (represented by bars with no cross-hatching) at optimal treatment temperatures. Further, in this embodiment, the thermistor temperatures are indicated as red bars (represented by bars with high-left to low-right cross-hatching) when detected temperatures exceed optimal temperatures.

In an example embodiment, when the temperature registered by the thermistor $T_L$ at the tip of the laser registers a temperature greater than the Laser Probe Min Temp parameter but less than the Laser Probe Max Temp parameter (defined as noted above), the control system displays the temperature as yellow bar 1130. The yellow bar in this embodiment indicates that the laser probe 100 is operating within an optimal treatment temperature range. In a further embodiment, if the temperature detected by $T_L$ at the tip of the laser probe 100 exceeds the predefined Laser Probe Setpoint Temp parameter, the control system displays the temperature as a red bar (not shown), indicating that the operator should consider cessation of treatment. If the temperature detected ever exceeds the Laser Probe Max Temp parameter, the control system automatically sends a signal to the laser source 108 causing it to cease emitting laser energy. In this embodiment, the control system continues monitoring the temperatures detected by each of the thermistors to enable the operator to determine when the probes may be safely removed from the skin of the patient. It should be appreciated that in different embodiments, the operator may resume treatment after the temperature detected by the laser probe thermistor exceeds the Laser Probe Max Temp if the operator selects a Resume Treatment button after the thermistor temperatures indicate temperatures within the treatment ranges defined by the parameters 1008.

Figure 14:
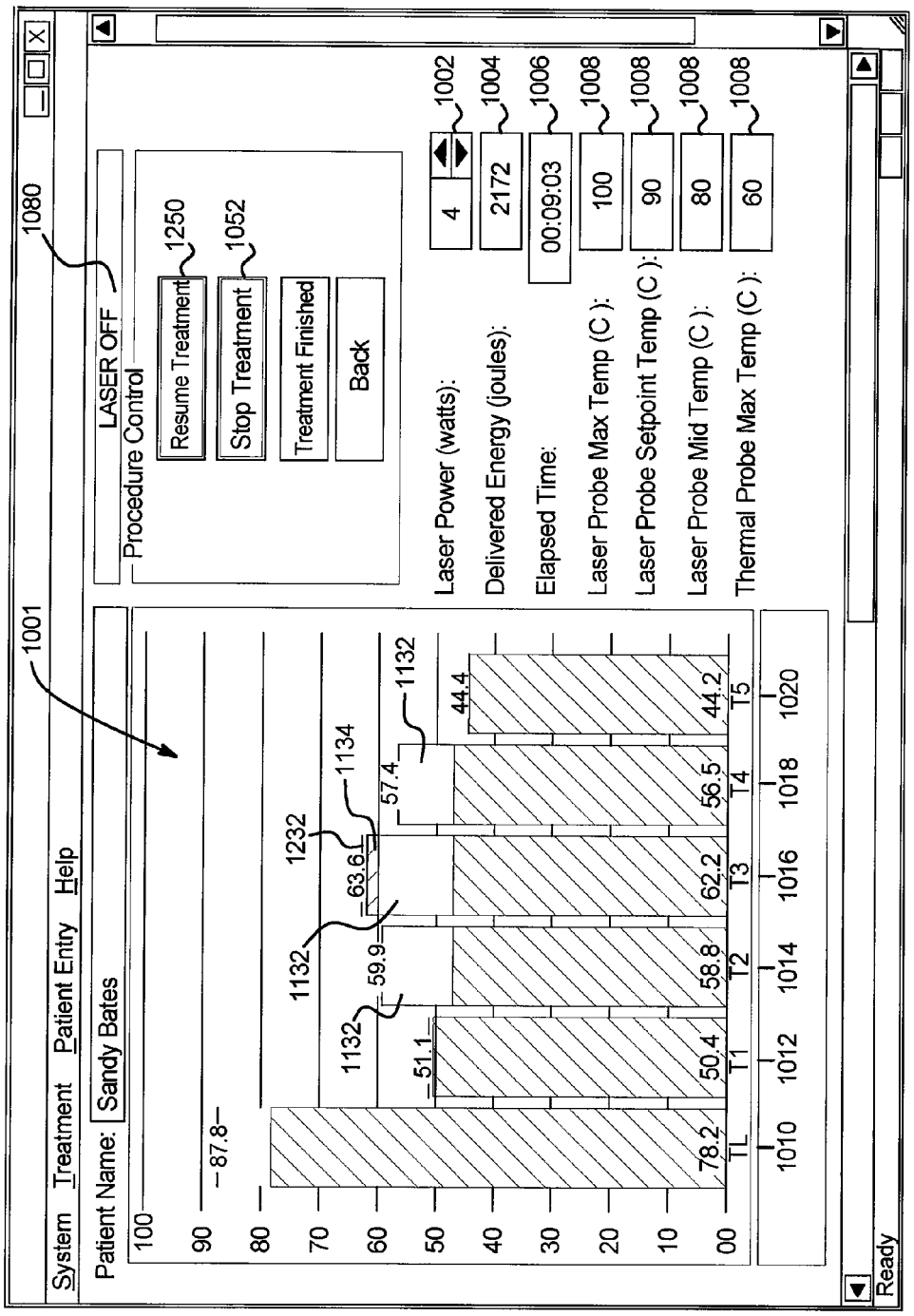
FIG. 14 is a screen shot of an example interstitial laser treatment screen displayed by the control system, which illustrates that each of the thermistors in the thermal probe has exceeded the predefined thermal probe maximum temperature, and that the interstitial laser treatment is complete.

Referring to FIG. 14, when the temperature detected by one of the thermal probe thermistors $T_1$-$T_5$ reaches 80% of a predefined Thermal Probe Max Temp, the control system in one embodiment displays a yellow bar 1132 representing the detected temperatures, indicating that the maximum acceptable temperature is being approached. In one embodiment, if the temperature detected by any of the thermal probe thermistors reaches 100% of the predefined Thermal Probe Max Temp, the control system displays a red bar 1134 indicating that the optimal tissue treatment temperature has been reached, and that can consider terminating treatment. It should be appreciated that the control system in one embodiment does not automatically stop treatment if one or more, but not all, of the thermal probe thermistors detect a temperature exceeding the Thermal Probe Max Temp.

Figure 15:
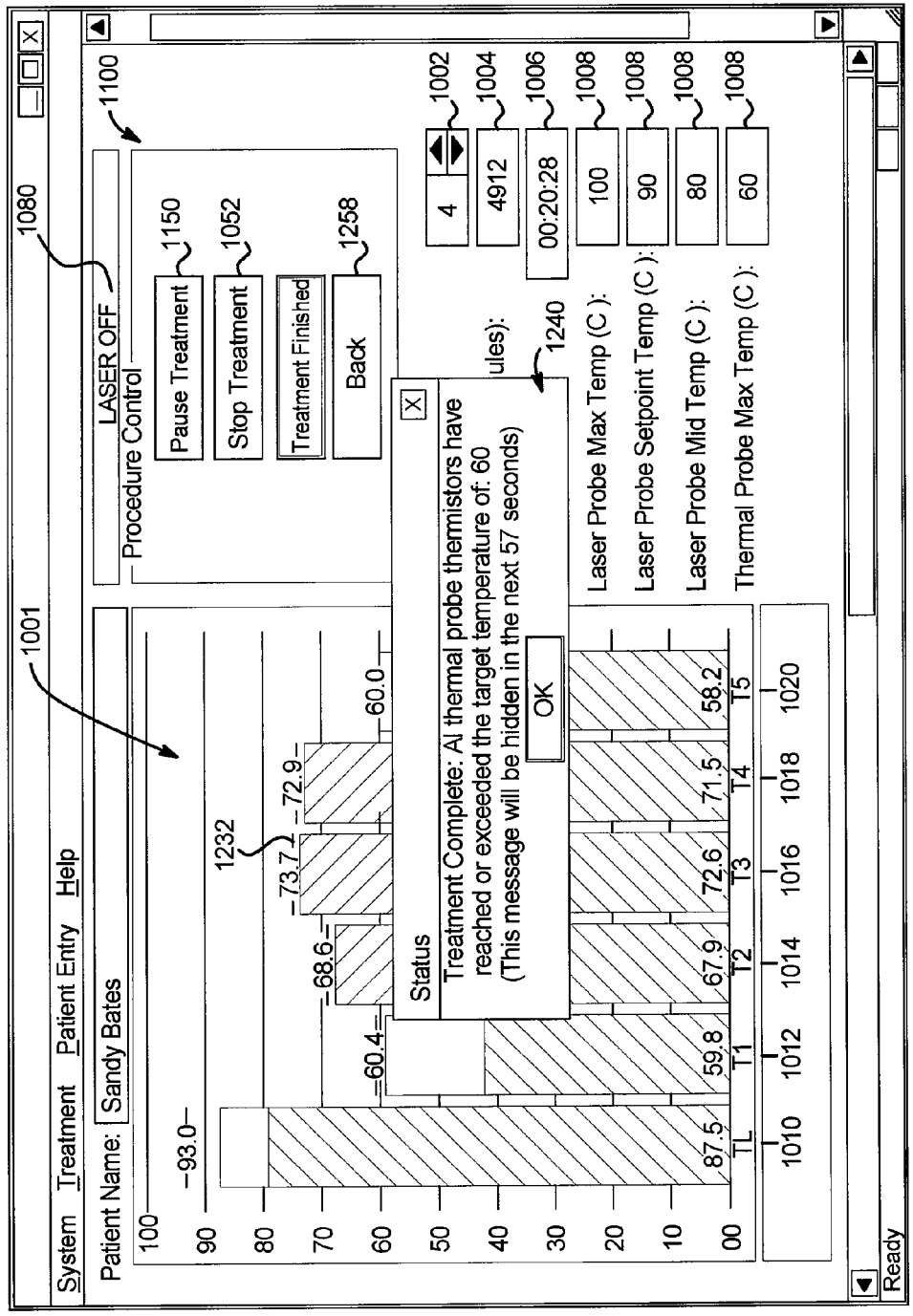
FIG. 15 is a screen shot of an example interstitial laser treatment screen displayed by the control system, which illustrates that one of the thermal probe thermistors has exceeded the predefined thermal probe maximum temperature, and that the interstitial laser therapy control system has disabled the laser source.

Referring now to FIG. 15, in one embodiment, the control system typically determines that a treatment is successful after a tumor with a diameter of 2.0 cm has been treated for between 15 and 30 minutes (e.g. 00:20:28, illustrated by elapsed time 1006). During a successful treatment, the temperature at the tip of the laser probe 100, indicated by $T_L$ 1012, typically reaches a maximum of between 50° C. and 60° C. before the temperatures in the surrounding tissue, detected by the thermistors of the thermal probe 102 ($T_1$-$T_5$) begin to rise. In one embodiment, the control system is configured to adjust the laser power and the saline infusion rate (e.g., by instructing the operator to change the rate on the infusion pump 106) to maintain a temperature at the tip of the laser probe 100 between 80° C. and 105° C. during treatment. In different embodiments, the control system enables the operator to determine any changes that need to be made to the amount of laser energy or the saline infusion rate to be applied. In this embodiment, the control system enables the operator to change the laser power by clicking an up or down arrow button of the Laser Power meter 1002.

In one embodiment, the control system determines that an interstitial laser treatment is successful and terminates treatment when the thermistors of the thermal probe, inserted in the tissue adjacent to the tumor mass, indicate a temperature of approximately 60° C. or more. Referring to FIG. 15, the line illustrated by numeral 1232 indicates the maximum temperature detected by the thermistor $T_3$ and represented by the bar 1016. As further illustrated in FIG. 15, each thermistor of the thermal probe $T_1$-$T_5$ indicates a temperature equal to or in excess of 60° C. Based on these detected temperatures, the control system in the illustrated embodiment that treatment is complete. The control system in one embodiment sends a signal to the laser source 108 to cause the laser source 108 stop providing laser energy. It should be appreciated that in some embodiments, when tumors with diameters smaller than 2.0 cm are being treated, the control system determines that treatment is complete when fewer than all of the thermistors of the thermal probe detect a temperature of approximately 60° C.

When the control system determines that treatment is complete based on the detected temperatures, it sends a signal to the laser source 108 to stop generating laser energy and thus terminates treatment. In one embodiment, illustrated in FIG. 15, the control system displays the Pause Treatment 1150 and Stop Treatment 1052 buttons as grayed out, and thus as unselectable. The control system also changes the message displayed in the status field 1080 to a static, non-flashing LASER OFF message. The control system in different embodiments displays a popup window 1240 informing the operator that all the thermal probe thermistors reached their maximum, predefined target temperatures. A digital temperature and marker line 1232 are displayed in one embodiment of the thermistor temperature display screen 1001 indicating the maximum temperature achieved by each thermistor during treatment. In this embodiment, the control system stops updating the Elapsed Time counter 1006 and Delivered Energy counter 1004.

Figure 16:
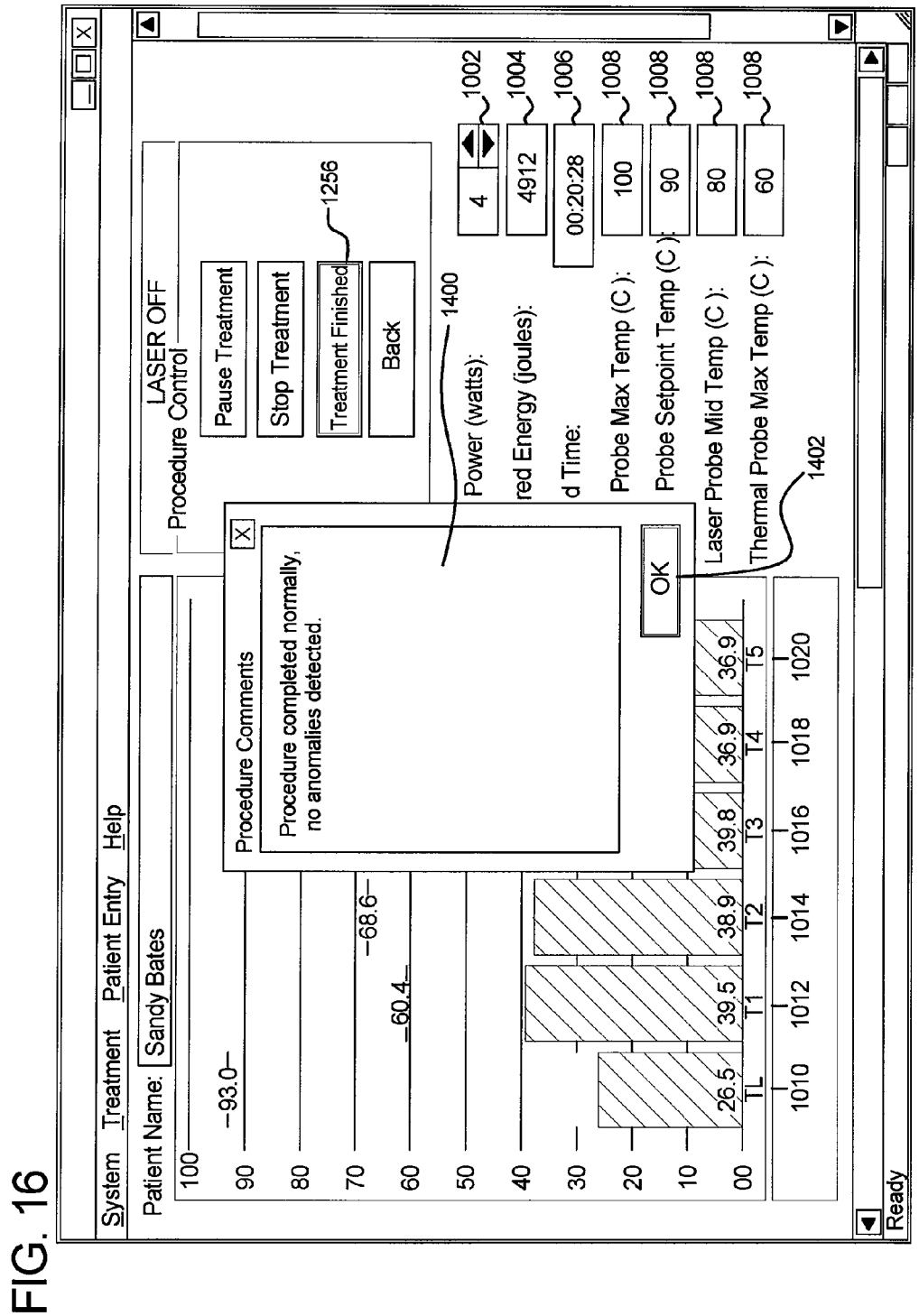
FIG. 16 is a screen shot of an example interstitial laser treatment screen displayed by the control system, which illustrates that at the completion of an interstitial laser treatment, the interstitial laser therapy control system enables the operator to enter comments about the treatment.

Referring now to FIG. 16, after treatment has been terminated, a cool-down period begins in one embodiment. During the cool-down period, the control system continues to display bars 1010, 1012, 1014, 1016, 1018, and 1020 representing the laser probe and thermal probe thermistor temperatures, enabling the control system and the operator to confirm that the treatment area is cooling down. The control system in different embodiments continues to store these temperature readings in the appropriate database record. The control system enables the operator to select a Treatment Finished button 1256 in one embodiment to stop storing data about detected thermistor temperatures, elapsed time, and laser power.

Pausing or Halting Treatment Using the Control System

The control system in different embodiments enables treatment to be paused temporarily or stopped permanently if the operator determines that such an action is necessary.

In one embodiment, if thermistor controller communicates that a thermistor, its associated wiring, or the thermistor controller fails during treatment, the control system displays a popup window indicating to the operator which thermistor or thermistors has or have the problem (not shown). Regardless of the detected failure, the control system continues to track the temperatures detected by the operational thermistors. In different embodiments, the thermistor controller detects the failure of the thermistor based on an incorrect or missing signal indicating a determined resistance. IN one such embodiment, the microprocessor detects the failure of one of the thermistors as a failure by the thermistor controller to provide a thermistor temperature as part of a thermistor temperature data set. For example, if the thermistor controller is monitoring thermistors $T_L$ and $T_1$-$T_5$, and the thermistor temperature data set contains only temperature $T_L$ and $T_1$-$T_4$, the thermistor temperature data set indicates to the microprocessor that thermistor $T_5$ has failed or is not functioning properly.

In one embodiment, if a thermistor of the thermal probe 102 fails during treatment, the control system determines whether to automatically terminate treatment by comparing the number of failed thermistors to the value stored in the Maximum Bad Thermal Probe Thermistor Limit parameter. If the number of bad thermistors equals or exceeds the stored value of the parameter, the control system automatically causes a signal to be sent to the laser source 108 to stop emitting laser energy, thereby terminating treatment. If the number of detected bad thermistors is less than the stored value of this parameter, the control system enables the operator to terminate treatment if necessary. In another embodiment, if the failed thermistor is on the laser probe 100 (i.e., if $T_L$ fails), the control system pauses treatment by sending a signal to cause the laser source 108 to stop emitting laser energy. In this embodiment, the control system keeps monitoring temperatures detected by the remaining functional thermistors. The control system also enables the operator to determine whether to continue treatment. If the operator decides to terminate treatment, and the control system provides the operator with a number of alternative ways to halt treatment, discussed below. In one embodiment, the control system does not pause treatment if the laser probe thermistor does not determine a thermistor temperature. Rather, the control system displays a message indicating the failed thermistor and allows the laser source 108 to continue emitting laser energy. In this embodiment, if the operator determines that treatment needs to be stopped, the operator actuates a button depending on the appropriate stoppage mechanism, discussed below.

As illustrated in FIG. 13, if the operator determines that treatment needs to be paused but not altogether terminated, the control system enables the operator to a select Pause Treatment button 1150. If the operator selects the Pause Treatment button 1150, the control system continues to monitor thermistor temperatures and update the thermistor temperature bars 1010, 1012, 1014, 1016, 1018, and 1020, illustrated in FIG. 14, and the infusion pump continues to generate a steady flow of saline or other solution, but the control system causes a command to be sent to the laser source 108 to cease generating laser energy. FIG. 14 illustrates that if the interstitial laser treatment has been paused, the control system generates and displays a digital temperature and marker line (e.g. 1232) at each bar's maximum temperature, indicating the temperature detected by each thermistor immediately before the operator paused the treatment. The control system also stops incrementing the elapsed time counter 1006 and delivered energy counter 1004. When the operator pauses treatment, the control system causes the Pause Treatment button 1150 to change to a Resume Treatment button 1250, and changes the message displayed in the status field 1080 to a non-flashing LASER OFF message. In a further embodiment, illustrated in FIG. 14, the control system enables the operator to change the laser power displayed in the laser power meter 1002 after the operator has paused treatment. If the operator so changes the laser power, the control system sends a message to the laser source 108 that causes the laser source to emit laser energy according to the changed laser power value.

Referring still to FIG. 14, the control system enables the operator to select the Resume Treatment button 1250 when the operator determines that it is safe to resume treatment. In one embodiment, the control system displays a popup window asking the operator to confirm that the infusion pump is running. When the operator selects the OK button, the control system sends a signal to the laser source 108 commanding it to begin generating laser energy, and the control system resumes the counters and any data monitoring and storage.

The control system in one embodiment (not shown) automatically pauses treatment if the laser probe thermistor ($T_L$) detects a temperature in excess of the predefined Laser Probe Max Temp parameter. If the control system detects this high temperature at the laser probe thermistor, it sends a signal to the laser source 108 commanding it to stop generating laser energy. Additionally, the control system displays a popup window and emits an audible beep to notify the operator that the maximum temperature has been exceeded and that treatment has been paused. If the control system causes treatment to be paused as in the above embodiment, the control system also enables the operator to resume treatment by selecting the Resume Treatment button 1250 after the laser probe thermistor temperature ($T_L$) has been reduced to an acceptable value.

In one embodiment, illustrated in FIGS. 13 and 14, the control system displays a Stop Treatment button 1052 which the operator may select at any time. If the operator selects the Stop Treatment button 1052, the control system sends a signal to the laser source 108 commanding it to stop emitting laser energy. Thus, the control system enables the operator to prevent laser energy from being applied to the tumor immediately upon selecting the Stop Treatment button 1052. As discussed above, the control system does not cease monitoring thermistor temperatures if the operator stops the treatment. The control system continues to record temperatures detected by each thermistor to enable the operator to determine when the tissue has cooled to enable the probes to be safely removed. Unlike the embodiment in which the operator selects the Pause Treatment button, the control system does not enable the operator to resume treatment after selecting the Stop Treatment button, and the data stored in the database indicates that the treatment was unsuccessful.

As discussed with reference to FIG. 2, the interstitial laser therapy apparatus includes an electro-mechanical shutter switch 202 mounted in one embodiment between the keyboard 208 and the monitor 112. It is an electro-mechanical switch—that is, the operator can actuate the switch regardless of what the control system is doing. The shutter switch 202 impacts treatment identically to the software Pause Treatment button 1150 displayed by the control system. However, rather than the control system sending a software-generated electrical signal to the laser source 108, an electrical signal is sent directly from the actuated electro-mechanical shutter switch 202 to the laser source 108. In one embodiment, upon receiving the signal from the electro-mechanical shutter switch 202, the laser source 108 closes a shutter to prevent emission of laser energy. Additionally, the laser source 108 in different embodiments sends a signal to the microprocessor indicating that the shutter of the laser source 108 is closed. In different embodiments, this causes the control system to behave as if the operator had selected the Pause Treatment button 1150. In one embodiment, this means that the control system continues monitoring the temperatures recorded by the various thermistors, but stops increasing the Elapsed Time counter 1006 and the Delivered Energy counter 1004. Additionally, actuating the shutter switch 202 causes the control system to display a Resume Treatment button 1250 instead of the Pause Treatment button 1150. In one embodiment, selecting the Resume Treatment button 1250 enables the operator to resume treatment causing the microprocessor to send a message to cause the laser source 108 to open the shutter. It should be appreciated that pausing treatment using the electro-mechanical shutter switch 202 as opposed to selecting the Pause Treatment button 1150 enables the operator to ensure that a signal is sent to close the shutter by actuation of an electro-mechanical device rather than relying on the microprocessor to send an appropriate signal. Additionally, if the software is unresponsive, the reporting may be improper, but the electro-mechanical shutter switch 202 enables the operator to be sure that a signal is sent to the laser source 108 to cease applying laser energy.

The interstitial laser therapy apparatus also includes an electro-mechanical emergency shutoff button 204, in one embodiment prominently located at the top of the cart 20. The electro-mechanical emergency shutoff button 204 in one embodiment activates control system's emergency stop function. If an operator is unable to stop the laser source 108 from generating energy by pausing the treatment by selecting the Pause Treatment button 1150 or by actuating the electro-mechanical shutter switch 202, actuating the emergency shutoff button 204 provides an electro-mechanical stop-gap. In one embodiment, actuating the emergency shutoff button 204 prevents any electricity from being supplied to the laser source 108. This is in contrast to the Pause Treatment button 1150 and/or the electro-mechanical shutter switch 202, which merely instruct the laser to cease emitting laser energy or send a signal to close a shutter. Preferably, the operator only actuates the electro-mechanical emergency shutoff button 204 in the event the laser source 108 becomes unresponsive to either commands from the microprocessor, becomes unresponsive to the shutter switch 202, or if some other condition occurs that requires immediate termination the power supplied to the laser source 108 that cannot be remedied by actuating the electro-mechanical shutter switch 202.

In one embodiment, the microprocessor regularly sends heartbeat signals to the laser source 108 to determine whether it is functioning. Thus, In one embodiment, if the operator actuates the electro-mechanical emergency shutoff button 204 to cut off power to the laser source 108, the microprocessor will not receive an adequate response to one of its heartbeat signals, thus indicating the laser source 108 is non-responsive. In this embodiment, the control system displays a popup window indicating a communications failure between the computer 110 and the laser source 108. In a further embodiment, the computer 110 emits an audible tone after about five seconds of the power to the laser source 108 being turned off. In different embodiments, the laser source 108 also monitors the connection with the microprocessor. If the laser source 108 determines that communication with the microprocessor has been lost or has failed, the laser source in one embodiment stops emitting laser energy. In this embodiment, the microprocessor detects the failure of communication and displays an appropriate message to the operator indicating that communication has failed. In different embodiments, the message displayed to the operator indicates that the communications link has been lost and that the laser source 108 should be off. In one such embodiment, the operator should double-check the laser source 108 to ensure that it is not emitting laser energy. The control system in various embodiments continues to monitor the temperatures detected by the various thermistors to enable the operator to determine the success of the treatment and when and whether it is safe to remove the probes from the tumor and tissue adjacent to the tumor.

Dealing with Trouble that Arises During Treatment

If during interstitial laser treatment performed with the interstitial laser therapy apparatus and kit(s) a malfunction of the infusion pump 106, syringe 118, or saline tube 114 occurs, the operator should select the Pause Treatment button 1150 displayed by the control system. The operator should replace the faulty item or items, re-prime the syringe 118, and select the Resume Treatment button 1250.

If the communication link between the computer 110 and the laser source 108 is lost and cannot be restored within a few seconds, the control system in one embodiment automatically shuts off power to the laser source 108. In a further embodiment, the computer 110 emits an audible alarm, and the control system updates the laser status bar 1080 to display the message COMMUNICATION FAILURE and displays a popup window informing the operator of the communication failure and instructing the operator to monitor the temperature bars and, if needed, turn off the laser source 108 by actuating the emergency stop button 204. It should be appreciated that in one embodiment, discussed above, the communication link between the microprocessor and the laser source 108 is lost because the operator actuates the emergency shut-off button 204 to cut off power to the laser source 108. In this embodiment, the control system verifies that power to the laser source 108 is off.

If a malfunction occurs with the laser source 108 during treatment, the laser source 108 ceases applying laser energy and sends a signal to the microprocessor to notify the control system of the problem. The control system then displays a popup window and the computer 110 emits an audible beep to alert the operator of the problem with the laser source 108. The control system in one embodiment continues to monitor the thermistor temperatures and continues to display them on the GUI. The displayed temperature bars enable the operator to monitor the thermistor temperatures to ensure the tissue cools down as expected. If the thermistors do not indicate that the temperature is dropping, or if temperatures continue to rise, the emergency stop button 204 enables the operator to cut power to the laser source 108.

Table 4 below represents a summary of certain problems and the appropriate corrective actions. The corrective actions are listed in order of increasing severity from left to right. If Table 4 contains an 'x' the corrective action indicated is sufficient to rectify the noted problem. It should be appreciated that in some embodiments, a column to the right of the leftmost 'x' in a given row represents an unreasonably aggressive reaction to the specific problem. For instance, for an infusion pump problem, pressing the Pause Treatment button 1150 would be appropriate, but pressing the red emergency stop button 204 is too aggressive in one embodiment.

TABLE 4

| Problem Event | Pause Treatment Button 1150 | Yellow Shutter Switch 202 | Stop Treatment Button 1152 | Emergency Stop Button 204 | Power Switch 200 |
|---|---|---|---|---|---|
| Infusion pump problem | X | X | X | X | X |
| Tumor temperature too high | X | X | X | X | X |
| Unintended laser exposure | X | X | X | X | X |
| Fiber optic cable break | | | X | X | X |
| Thermistor fault requiring termination | | | X | X | X |
| Laser fault | | | X | X | X |
| Laser/software communication fault | | | X | X | X |
| Shutter switch failure | | | X | X | X |
| Computer hardware fault | | | | X | X |
| Software fault | | | | X | X |
| Laser fails to turn off via red emergency stop button | | | | | X |
| Laser fails to turn off via key lock | | | | | X |
| Electrical shock | | | | | X |

Finishing Treatment

In one embodiment, when the laser source 108 has been turned off, the tissue begins to cool. The method for safely removing the probes is applicable no matter the means by which the laser was turned off—that is, it applies whether the control system ended treatment, the control system enabled the operator to stop treatment by selecting the Stop Treatment button 1152, the control system enabled the operator to stop treatment by actuating the electro-mechanical shutter switch 202, the control system enabled the operator to stop treatment by actuating the electro-mechanical emergency shutoff button 204, or treatment ended for another reason.

In one embodiment, even after the laser source 108 stops generating laser energy, the infusion pump 106 continues to pump saline solution into through the laser probe 100. Since the saline solution is at room temperature, continued circulation of saline solution gradually cools the tissue. The control system continues to track and display the temperatures detected by the various thermistors, as illustrated in FIG. 16, enabling the operator to determine when safe tissue temperatures have been reached such that the probes may be removed. When the tissue temperatures are low enough, the control system enables the operator in one embodiment to select the Treatment Finished button 1256, and the control system stops collecting data. The control system displays a popup window instructing the operator to stop the infusion pump 106. In different embodiments, the microprocessor is configured to co-act with the infusion pump 106, so when treatment is finished the microprocessor sends an appropriate signal to the infusion pump 106 to turn it off.

In one embodiment, illustrated by FIG. 16 the control system displays a popup window 1400 enabling the operator to enter comments about the treatment using the keyboard 208 or mouse 206. When the operator indicates the comments are complete by selecting the OK button 1402, the control system associates the comments with the treated patient and stores them on the memory device.

In different embodiments, once the tissue has sufficiently cooled, the operator extracts the probes 100 and 102 from the tissue. The instructions included with the interstitial laser therapy kit(s) in different embodiments require that the probes 100 and 102 be discarded in a sharps container or other approved receptacle. The instructions similarly describe that all other single-use items in the kit(s) should be similarly discarded. In one embodiment, the instructions indicate that none of these items may be reused or sterilized with the intent to reuse. As noted above, in different embodiments, the items included in the kit 300 are not disposable but are designed to be returned to the provider or another entity for sterilization, testing, and re-packaging.

In one embodiment, the stereotactic imaging device enables the operator to take necessary post-procedure stereotactic images prior to the patient leaving the treatment table. The compression plates 18 enable the operator to decompresses the breast and remove any monitoring devices. The medical material included in the kit(s) in different embodiments enable the operator to apply a sterile bandage and to place an ice pack on the breast.

In one embodiment, the operator turns off the infusion pump 106 by pressing its POWER button. Additionally, the operator turns off the laser source 108 by turning its keyswitch 210 counter-clockwise and ensuring that the laser power LED 218 is no longer backlit. The operator shuts down the computer 110 from the WINDOWS XP™ desktop by selecting Start, Shut Down, and OK on the Shut Down Windows screen.

It should be appreciated that the present disclosure is not limited to interstitial last energy therapy, and particularly, interstitial laser therapy for the destruction of a breast tumor. The present disclosure may apply to a variety of different non-surgical treatments for the destruction of a variety of different tumor masses.

It should be understood that modifications and variations may be effected without departing from the scope of the novel concepts of the present disclosure, and it should be understood that this application is to be limited only by the scope of the appended claims.

The invention is claimed as follows:

1. An interstitial laser therapy system comprising:
an interstitial laser therapy kit including:
(a) a laser probe including a laser probe thermistor;
(b) a thermal probe including a thermal probe thermistor;
(c) an optical fiber;
(d) a plurality of separate probe holders, each said probe holder configured to hold both the laser probe and the thermal probe, for a single interstitial laser therapy treatment using an interstitial laser therapy apparatus, each said probe holder defining a plurality of spaced apart laser probe receiving channels and at least one thermal probe receiving channel;
(e) a non-resealable container, wherein the laser probe, the thermal probe, the optical fiber, and the probe holders are in the non-resealable container; and
(f) a unique kit identifier on or in the non-resealable container and configured to specifically identify said interstitial laser therapy kit including said laser probe, said thermal probe, said optical fiber, and said probe holders; and
a controller configured to receive the unique kit identifier to: (i) enable use of said laser probe, said thermal probe, said optical fiber, and said probe holders with the interstitial laser therapy apparatus for said interstitial laser therapy treatment a single time, wherein said interstitial laser therapy is controlled by the controller, and (ii) prevent said interstitial laser therapy kit from being used for a subsequent interstitial laser therapy treatment with said interstitial laser therapy apparatus.

2. The interstitial laser therapy system of claim 1, wherein the laser probe includes a cannula and a stylet insertable in the cannula.

3. The interstitial laser therapy system of claim 2, wherein the cannula includes a trocar.

4. The interstitial laser therapy system of claim 1, wherein the laser probe includes a thermistor wire connected to the laser probe thermistor and a laser probe connector connected to the thermistor wire and connectable to a connector box.

5. The interstitial laser therapy system of claim 1, wherein the thermal probe includes a plurality of thermistors, a plurality of thermistor wires each connected to a different one of the plurality of thermistors, and a thermal probe connector connected to the plurality of thermistor wires and connectable to a connector box.

6. The interstitial laser therapy system of claim 1, wherein the thermal probe includes a plurality of spaced apart positioning marks.

7. The interstitial laser therapy system of claim 6, wherein at least one of the probe holders includes a section configured to be rotatably insertable in a probe holder attachment connectable to an imaging unit.

8. The interstitial laser therapy system of claim 1, wherein at least one of the probe holders includes a section configured to be rotatably insertable in a probe holder attachment connectable to an imaging unit.

9. The interstitial laser therapy system of claim 1, wherein the unique kit identifier is printed on a label affixed to the non-resealable container.

10. The interstitial laser therapy system of claim 1, wherein the kit includes a kit identifier sheet including the unique kit identifier in the non-resealable container.

11. The interstitial laser therapy system of claim 1, wherein the unique kit identifier is on the non-resealable container.

12. The interstitial laser therapy system of claim 1, wherein the laser probe, the thermal probe, the optical fiber, and the probe holders are mounted on a support structure in the non-resealable container.

13. The interstitial laser therapy system of claim 1, which includes a plurality of sheaths, wherein the laser probe is protected by a first one of the sheaths, the thermal probe is protected by a second one of the sheaths, and the optical fiber is protected by a third one of the sheaths.

14. The interstitial laser therapy system of claim 1 which includes an instruction sheet in the non-resealable container, the instruction sheet having printed instructions to dispose of the laser probe, the thermal probe, the optical fiber, and the probe holders.

15. An interstitial laser therapy system comprising:
an interstitial laser therapy kit including:
(a) a laser probe including a cannula and a stylet removably insertable in the cannula;
(b) a thermal probe including a plurality of thermistors;
(c) an optical fiber;
(d) a plurality of probe holders, each said probe holder configured to hold the thermal probe relative to the laser probe for a single interstitial laser therapy treatment using an interstitial laser therapy apparatus, each said probe holder defining a plurality of laser probe receiving channels and at least one thermal probe receiving channel;
(e) a non-resealable container, wherein the laser probe, the thermal probe, the optical fiber, and the probe holders are in the non-resealable container; and
(f) a unique kit identifier on or in the non-resealable container and configured to specifically identify said interstitial laser therapy kit including said laser probe, said thermal probe, said optical fiber, and said probe holders; and a controller configured to receive the unique kit identifier to: (i) enable use of said laser probe, said thermal probe, said optical fiber, and said probe holders with the interstitial laser therapy apparatus for said interstitial laser therapy treatment a single time, wherein said interstitial laser therapy is controlled by the controller, and (ii) prevent said interstitial laser therapy kit from being used for a subsequent interstitial laser therapy treatment with said interstitial laser therapy apparatus.

16. The interstitial laser therapy system of claim 15, wherein:
 (i) the laser probe includes a thermistor, a thermistor wire connected to the laser probe thermistor, and a laser probe connector connected to the thermistor wire and connectable to a connector box;
 (ii) the thermal probe includes a plurality of thermistors, a plurality of thermistor wires each connected to a different one of the plurality of thermistors, a thermal probe connector connected to the plurality of thermistor wires and connectable to the connector box;
 (iii) the unique kit identifier is printed on a label affixed to the non-resealable container;
 (iv) the laser probe is protected by a first sheath, the thermal probe is protected by a second sheath, and the optical fiber is protected by a third sheath; and
 (v) the laser probe, the thermal probe, the optical fiber, and the probe holders are removably mounted on a support structure in the non-resealable container.

17. An interstitial laser therapy system comprising:
an interstitial laser therapy kit including:
 (a) a laser probe, a thermal probe, and at least one probe holder, each said probe holder including a section configured to be rotatably attachable to a probe holder attachment connectable to an imaging unit, each said probe holder configured to hold the thermal probe relative to the laser probe for a single interstitial laser therapy treatment using an interstitial laser therapy apparatus, each said probe holder defining a plurality of laser probe receiving channels and at least one thermal probe receiving channel;
 (b) said laser probe including a laser probe thermistor, the laser probe insertable through each probe holder;
 (c) said thermal probe including a plurality of thermal probe thermistors, the thermal probe insertable through each probe holder;
 (d) an optical fiber insertable in the laser probe;
 (e) a support structure on which each probe holder, the laser probe, the thermal probe, and the optical fiber are removably mounted;
 (e) a container, wherein the support structure, each probe holder, the laser probe, the thermal probe, and the optical fiber are in the container; and
 (f) a unique kit identifier on or in the container and configured to specifically identify said interstitial laser therapy kit including said at least one probe holder, said laser probe, said thermal probe, and said optical fiber; and
a controller configured to receive the unique kit identifier to: (i) enable use of said at least one probe holder, said laser probe, said thermal probe, and said optical fiber with the interstitial laser therapy apparatus for said interstitial laser therapy a single time, wherein said interstitial laser therapy treatment is controlled by the controller, and (ii) prevent said interstitial laser therapy kit from being used for a subsequent interstitial laser therapy treatment with said interstitial laser therapy apparatus.

18. The interstitial laser therapy system of claim 17, wherein the container is a non-resealable plastic bag.

19. The interstitial laser therapy system of claim 18, wherein the unique kit identifier is on the non-resealable plastic bag.

20. An interstitial laser therapy system comprising:
an interstitial laser therapy kit including:
 (a) at least one probe holder, each said probe holder including a plurality of laser probe channels, at least one thermal probe channel, and a bushing rotatably insertable in a probe holder attachment;
 (b) a laser probe cannula insertable through any one of the laser probe channels in each probe holder such that the laser probe does not contact the probe holder attachment when the laser probe cannula is inserted in said laser probe channel for a single interstitial laser therapy treatment using an interstitial laser therapy apparatus;
 (c) a stylet insertable in the laser probe cannula;
 (d) a thermal probe insertable through the at least one thermal probe channel in each probe holder;
 (e) an optical fiber insertable in the laser probe cannula;
 (f) a non-resealable bag, wherein each probe holder, the laser probe cannula, the stylet, the thermal probe, and the optical fiber are in the non-resealable bag; and
 (g) a unique kit identifier on or in the bag and configured to specifically identify said interstitial laser therapy kit including said at least one probe holder, said laser probe cannula, said stylet, said thermal probe, and said optical fiber; and
a controller configured to receive the unique kit identifier to: (i) enable use of said at least one probe holder, said laser probe cannula, said stylet, said thermal probe, and said optical fiber with the interstitial laser therapy apparatus for said interstitial laser therapy treatment a single time, wherein said interstitial laser therapy is controlled by the controller, and (ii) prevent said interstitial laser therapy kit from being used for a subsequent interstitial laser therapy treatment with said interstitial laser therapy apparatus.

21. The interstitial laser therapy system of claim 20, wherein the thermal probe includes at least one positioning mark.

22. The interstitial laser therapy system of claim 20, wherein the unique kit identifier is printed on a label affixed to the non-resealable bag.

23. The interstitial laser therapy system of claim 20, wherein the unique kit identifier is in the non-resealable bag.

24. An interstitial laser therapy system comprising:
an interstitial laser therapy kit including:
 (a) at least one probe holder, each said probe holder defining a plurality of laser probe receiving channels and at least one thermal probe receiving channel;
 (b) a laser probe cannula including a thermistor, the laser probe cannula insertable in each probe holder for interstitial laser therapy;
 (c) a stylet insertable in the laser probe cannula;
 (d) a thermal probe including a plurality of thermistors, the thermal probe insertable in each probe holder for a single interstitial laser therapy treatment using an interstitial laser therapy apparatus;
 (e) an optical fiber insertable in the laser probe cannula;
 (f) a hemostasis valve connectable to the laser probe cannula;
 (g) a saline tube connectable to the hemostasis valve;
 (h) a saline syringe connectable to the saline tube;

(i) at least one container containing each probe holder, the laser probe cannula, the stylet, the thermal probe, the optical fiber, the hemostasis valve, the saline tube, and the saline syringe; and (j) a unique kit identifier on or in the at least one container and configured to specifically identify said interstitial laser therapy kit including each probe holder, the laser probe cannula, the stylet, the thermal probe, the optical fiber, the hemostasis valve, the saline tube, and the saline syringe; and a controller configured to receive the unique kit identifier to: (i) enable use of each probe holder, the laser probe cannula, the stylet, the thermal probe, the optical fiber, the hemostasis valve, the saline tube, and the saline syringe with the interstitial laser therapy apparatus a single time, wherein said interstitial laser therapy treatment is controlled by the controller, and (ii) prevent said interstitial laser therapy kit from being used for a subsequent interstitial laser therapy treatment with said interstitial laser therapy apparatus.

25. The interstitial laser therapy system of claim 24, wherein each probe holder, the laser probe cannula, the stylet, the thermal probe, and the optical fiber are contained in a first one of the containers.

26. The interstitial laser therapy system of claim 25, wherein the hemostasis valve, the saline tube, and the saline syringe are contained in a second one of the containers.

27. The interstitial laser therapy system of claim 25, wherein the unique kit identifier is on or in the first one of the containers.

28. The interstitial laser therapy system of claim 25, wherein the first one of the containers is a non-resealable plastic bag.

29. The interstitial laser therapy system of claim 28, which includes a support structure on which each probe holder, the laser probe cannula, the stylet, the thermal probe, and the optical fiber are positioned in the nonresealable plastic bag.

30. The interstitial laser therapy system of claim 25, wherein the first one of the containers includes an instruction sheet for disposing of each probe holder, the laser probe cannula, the stylet, the thermal probe, and the optical fiber after opening the first one of the containers.

31. An interstitial laser therapy system comprising:
an interstitial laser therapy kit including:
(a) a laser probe including a cannula and a stylet;
(b) a thermal probe;
(c) an optical fiber;
(d) at least one probe holder configured to hold both the laser probe and the thermal probe for a single interstitial laser therapy treatment using an interstitial laser therapy apparatus, each said probe holder defining a plurality of laser probe receiving channels and at least one thermal probe receiving channel spaced apart from said laser probe receiving channels;
(e) a hemostasis valve;
(f) a saline tube;
(g) a saline syringe;
(h) a support structure;
(i) at least two non-resealable bags, wherein the laser probe, the thermal probe, the optical fiber, and each probe holder are positioned on the support structure in a first one of the non-resealable bags and wherein the hemostasis valve, the saline tube, and the saline syringe are in at least one other of the non-resealable bags; and
(j) a unique kit identifier on or in the first one of the non-resealable bags and configured to specifically identify said interstitial laser therapy kit including said laser probe including the cannula and the stylet, said thermal probe, said optical fiber, said at least one probe holder, said hemostasis valve, said saline tube, and said saline syringe; and a controller configured to receive the unique kit identifier to: (i) enable use of said laser probe including the cannula and the stylet, said thermal probe, said optical fiber, said at least one probe holder, said hemostasis valve, said saline tube, and said saline syringe with the interstitial laser therapy apparatus a single time, wherein said interstitial laser therapy treatment is controlled by the controller, and (ii) prevent said interstitial laser therapy kit from being used for a subsequent interstitial laser therapy treatment with said interstitial laser therapy apparatus.

32. The interstitial laser therapy system of claim 1, wherein the interstitial laser therapy kit includes a hemostasis valve connectable to the laser probe.

33. The interstitial laser therapy system of claim 15, wherein the interstitial laser therapy kit includes a hemostasis valve connectable to the laser probe.

34. The interstitial laser therapy system of claim 15, wherein each of the plurality of probe holders includes a section configured to co-act with a probe holder attachment connectable to an imaging unit.

35. The interstitial laser therapy system of claim 17, wherein the interstitial laser therapy kit includes a hemostasis valve connectable to the laser probe.

36. The interstitial laser therapy system of claim 17, wherein each probe holder includes a section configured to be rotatably insertable in the probe holder attachment connectable to the imaging unit.

37. The interstitial laser therapy system of claim 20, which wherein the interstitial laser therapy kit includes a hemostasis valve connectable to the laser probe cannula.

38. An interstitial laser therapy system comprising:
an interstitial laser therapy kit including:
(a) a laser probe including:
(i) a cannula, said cannula including a laser probe thermistor and a thermistor wire connected to the laser probe thermistor, and
(ii) a stylet insertable in the cannula;
(b) a laser probe connector connected to the thermistor wire and connectable to a connector box;
(c) a thermal probe including:
(i) a plurality of spaced apart thermistors, and
(ii) a plurality of thermistor wires each connected to a different one of the plurality of thermistors;
(d) a thermal probe connector connected to the plurality of thermistor wires and connectable to the connector box;
(e) an optical fiber;
(f) a plurality of protectors for the laser probe, the thermal probe, and the optical fiber;
(g) at least one probe holder, each said probe holder configured to hold both the laser probe and the thermal probe for a single interstitial laser therapy treatment using an interstitial laser therapy apparatus, each said probe holder defining a plurality of laser probe receiving channels and at least one thermal probe receiving channel;
(h) at least one non-resealable container, wherein the laser probe, the laser probe connector, the thermal probe, the thermal probe connector, the optical fiber, the protectors, and the at least one probe holder are in the at least one non-resealable container;

(i) a support structure in the at least one non-resealable container; and
(j) a unique kit identifier on or in the at least one non-resealable container and configured to specifically identify said interstitial laser therapy kit including said laser probe, said laser probe connector, said thermal probe, said thermal probe connector, said optical fiber, said protectors, and said at least one probe holder; and a controller configured to receive the unique kit identifier to: (i) enable use of said laser probe, said laser probe connector, said thermal probe, said thermal probe connector, said optical fiber, and said at least one probe holder with the interstitial laser therapy apparatus for said interstitial laser therapy treatment a single time, wherein said interstitial laser therapy is controlled by the controller, and (ii) prevent said interstitial laser therapy kit from being used for a subsequent interstitial laser therapy treatment with said interstitial laser therapy apparatus.

39. The interstitial laser therapy system of claim 38, wherein the interstitial laser therapy kit includes a hemostasis valve connectable to the cannula of the laser probe, a saline tube connectable to the hemostasis valve, and a saline syringe connectable to the saline tube.

40. The interstitial laser therapy system of claim 38, wherein the protectors for the laser probe, the thermal probe, and the optical fiber includes a plurality of sheaths, wherein the laser probe is protected by a first one of the sheaths, the thermal probe is protected by a second one of the sheaths, and the optical fiber is protected by a third one of the sheaths.

41. An interstitial laser therapy system comprising:
an interstitial laser therapy kit including:
(a) a laser probe including a laser probe thermistor;
(b) a thermal probe including a thermal probe thermistor;
(c) an optical fiber;
(d) at least one probe holder, each said probe holder configured to hold both the laser probe and the thermal probe for a single interstitial laser therapy treatment using an interstitial laser therapy apparatus, each said probe holder defining a plurality of laser probe receiving channels and at least one thermal probe receiving channel;
(e) a non-resealable container, wherein the laser probe, the thermal probe, the optical fiber, and the at least one probe holder are in the non-resealable container; and
(f) a unique kit identifier on or in the non-resealable container and configured to specifically identify said interstitial laser therapy kit including said laser probe, said thermal probe, said optical fiber, and said at least one probe holder; and a controller configured to receive the unique kit identifier to: (i) enable use of said laser probe, said thermal probe, said optical fiber, and said at least one probe holder with the interstitial laser therapy apparatus for said interstitial laser therapy treatment a single time, wherein said interstitial laser therapy is controlled by the controller, and (ii) prevent said interstitial laser therapy kit from being used for a subsequent interstitial laser therapy treatment with said interstitial laser therapy apparatus.

* * * * *

UNITED STATES PATENT AND TRADEMARK OFFICE
CERTIFICATE OF CORRECTION

| | | |
|---|---|---|
| PATENT NO. | : 8,979,829 B2 | Page 1 of 1 |
| APPLICATION NO. | : 12/025157 | |
| DATED | : March 17, 2015 | |
| INVENTOR(S) | : Tomasello et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1979 days.

Signed and Sealed this
Eighth Day of September, 2015

Michelle K. Lee
*Director of the United States Patent and Trademark Office*